United States Patent
Larsen et al.

(10) Patent No.: US 10,023,564 B2
(45) Date of Patent: Jul. 17, 2018

(54) G PROTEIN-COUPLED RECEPTOR KINASE 2 INHIBITORS AND METHODS FOR USE OF THE SAME

(71) Applicant: THE REGENTS OF THE UNIVERSITY OF MICHIGAN, Ann Arbor, MI (US)

(72) Inventors: Scott D. Larsen, South Lyon, MI (US); Kristoff Homan, Newton, MA (US); Helen Waldschmidt, Ann Arbor, MI (US); John J. G. Tesmer, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1 day.

(21) Appl. No.: 15/501,888

(22) PCT Filed: Aug. 10, 2015

(86) PCT No.: PCT/US2015/044468
§ 371 (c)(1),
(2) Date: Feb. 6, 2017

(87) PCT Pub. No.: WO2016/023028
PCT Pub. Date: Feb. 11, 2016

(65) Prior Publication Data
US 2017/0240538 A1    Aug. 24, 2017

Related U.S. Application Data

(60) Provisional application No. 62/034,906, filed on Aug. 8, 2014.

(51) Int. Cl.
*C07D 413/14* (2006.01)
*C07D 401/14* (2006.01)
*C07D 403/12* (2006.01)
*C07D 403/14* (2006.01)
*C07D 405/14* (2006.01)

(52) U.S. Cl.
CPC ......... *C07D 413/14* (2013.01); *C07D 401/14* (2013.01); *C07D 403/12* (2013.01); *C07D 403/14* (2013.01); *C07D 405/14* (2013.01)

(58) Field of Classification Search
CPC ... C07D 403/14; C07D 403/12; C07D 401/14
See application file for complete search history.

(56) References Cited

U.S. PATENT DOCUMENTS

| 7,348,305 | B2 | 3/2008 | Kern et al. |
| 7,560,467 | B2 * | 7/2009 | Drewry ................ C07D 401/14 514/274 |
| 2007/0099944 | A1 | 5/2007 | Drewry |
| 2010/0048479 | A1 | 2/2010 | Lymperopoulos et al. |

FOREIGN PATENT DOCUMENTS

| WO | WO-2003/051877 A1 | 6/2003 |
| WO | WO-2004/112719 A2 | 12/2004 |
| WO | WO-2007/034846 A1 | 3/2007 |

OTHER PUBLICATIONS

Bell et al., Optimization of novel nipecotic bis(amide) inhibitors of the Rho/MKL1/SRF transcriptional pathway as potential anti-metastasis agents, Bioorg. Med. Chem. Lett., 23(13):3826-32 (2013).
Benovic et al., Beta-adrenergic receptor kinase: primary structure delineates a multigene family, Science, 246(4927):235-40 (1989).
Benovic et al., Inhibition of the beta-adrenergic receptor kinase by polyanions, J. Biol. Chem., 264(12):6707-10 (1989).
Boguth et al., Molecular basis for activation of G protein-coupled receptor kinases, EMBO J., 29(19):3249-59 (2010).
Báez-Santos et al., X-ray structural and biological evaluation of a series of potent and highly selective inhibitors of human coronavirus papain-like proteases, J. Med. Chem., 57(6):2393-412 (2014).
Cai et al., A potent and orally active antagonist (SM-406/AT-406) of multiple inhibitor of apoptosis proteins (IAPs) in clinical development for cancer treatment, J. Med. Chem., 54(8):2714-26 (2011).
Claing et al., Endocytosis of G protein-coupled receptors: roles of G protein-coupled receptor kinases and beta-arrestin proteins, Prog. Neurobiol., 66(2):61-79 (2002).
Diviani et al., Effect of different G protein-coupled receptor kinases on phosphorylation and desensitization of the alpha1B-adrenergic receptor, J. Biol.. Chem., 271(9):5049-58 (1996).
Eschenhagen, Beta-adrenergic signaling in heart failure-adapt or die, Nat. Med., 14(5):485-7 (2008).

(Continued)

*Primary Examiner* — Alexander R Pagano
*Assistant Examiner* — Ebenezer Sackey
(74) *Attorney, Agent, or Firm* — Marshall, Gerstein & Borun LLP

(57) ABSTRACT

Disclosed herein are novel GRK2 inhibitors and methods for their use in treating or preventing heart disease, such as cardiac failure, cardiac hypertrophy, and hypertension. In particular, disclosed herein are compounds of Formula (I) and pharmaceutically acceptable salt thereof: wherein the substituents are as described.

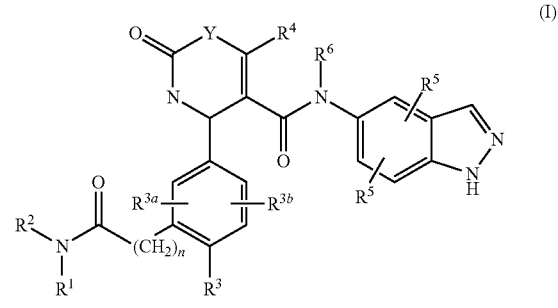

20 Claims, 1 Drawing Sheet

(56) References Cited

OTHER PUBLICATIONS

Evelyn et al., Design, synthesis and prostate cancer cell-based studies of analogs of the Rho/MKL1 transcriptional pathway inhibitor, CCG-1423, Bioorg. Med. Chem. Lett., 20(2):665-7 (2010).
Fang et al., Population pharmacokinetics of humanized monoclonal antibody HuCC49deltaCH2 and murine antibody CC49 in colorectal cancer patients, J. Clin. Pharmacol., 47(2):227-37 (2007).
Fang et al., Predictive physiologically based pharmacokinetic model for antibody-directed enzyme prodrug therapy, Drug Metab. Dispos., 36(6):1153-65 (2008).
Gold et al., Determining the absolute requirement of G protein-coupled receptor kinase 5 for pathological cardiac hypertrophy: short communication, Circ. Res., 111(8):1048-53 (2012).
Goodman et al., Development of dihydropyridone indazole amides as selective Rho-kinase inhibitors, J. Med. Chem., 50(1):6-9 (2007).
Gurevich et al., G protein-coupled receptor kinases: more than just kinases and not only for GPCRs, Pharmacol. Ther., 133(1):40-69 (2012).
Gurevich et al., The structural basis of arrestin-mediated regulation of G-protein-coupled receptors, Pharmcol. Ther., 110(3):465-502 (2006).
Haak et al., Targeting the myofibroblast genetic switch: inhibitors of myocardin-related transcription factor/serum response factor-regulated gene transcription prevent fibrosis in a murine model of skin injury, J. Pharmacol. Exp. Ther., 349(3):480-6 (2014).
Hata et al., Genetic manipulation of myocardial beta-adrenergic receptor activation and desensitization, J. Mol. Cell Cardiol., 37(1):11-21 (2004).
Hausdorff et al., Two kinases mediate agonist-dependent phosphorylation and desensitization of the beta 2-adrenergic receptor, Symp. Soc. Exp. Biol., 44:225-49 (1990).
Heidenreich et al., Forecasting the future of cardiovascular disease in the United States: a policy statement from the American Heart Association, Circulation, 123(8):933-44 (2011).
Homan et al., Structural and functional analysis of g protein-coupled receptor kinase inhibition by paroxetine and a rationally designed analog, Mol. Pharmacol., 85(2):237-48 (2014).
Iino et al., Rational design and evaluation of new lead compound structures for selective betaARK1 inhibitors, J. Med. Chem., 45(11):2150-9 (2002).
International Preliminary Report on Patentability, International Application No. PCT/US2015/044468, dated Feb. 14, 2017.
International Search Report and Written Opinion, International Application No. PCT/US15/44468, dated Apr. 1, 2016.
Koch et al., Cardiac function in mice overexpressing the beta-adrenergic receptor kinase or a beta ARK inhibitor, Science, 268(5215):1350-3 (1995).
Koch et al., The binding site for the beta gamma subunits of heterotrimeric G proteins on the beta-adrenergic receptor kinase, J. Biol. Chem., 268(11):8256-60 (1993).
Kulanthaivel et al., Balanol: a novel and potent inhibitor of protein kinase C from the fungus *Verticillium balanoides*, J. Am. Chem. Soc., 115(14):6452-3 (1993).
Larsen et al., 7-Oxo-4,7-dihydrothieno[3,2-b]pyridine-6-carboxamides: synthesis and biological activity of a new class of highly potent inhibitors of human cytomegalovirus DNA polymerase, Bioorg. Med. Chem. Lett., 17(14):3840-4 (2007).
Larsen et al., Modification of the N-terminus of peptidomimetic protein tyrosine phosphatase 1B (PTP1B) inhibitors: identification of analogues with cellular activity, Bioorg. Med. Chem. Lett., 13(5):971-5 (2003).
Larsen et al., Property-based design of a glucosylceramide synthase inhibitor that reduces glucosylceramide in the brain, J. Lipid Res., 53(2):282-91 (2012).
Larsen et al., Synthesis and biological activity of a novel class of small molecular weight peptidomimetic competitive inhibitors of protein tyrosine phosphatase 1B, J. Med. Chem., 45(3):598-622 (2002).
Lefkowitz et al., Role of phosphorylation in desensitization of the beta-adrenoceptor, Trends Pharmacol. Sci., 11(5):190-4 (1990).
Lipinski et al., Experimental and computational approaches to estimate solubility and permeability in drug discovery and development settings, Adv. Drug Deliv. Rev., 46(1-3):3-26 (2001).
Lodowski et al., Keeping G proteins at bay: a complex between G protein-coupled receptor kinase 2 and Gbetagamma, Science, 300(5623):1256-62 (2003).
Loomis et al., Sangivamycin, a nucleoside analogue, is a potent inhibitor of protein kinase C, J. Biol. Chem., 263(4):1682-92 (1988).
Lymperopoulos et al., Reduction of sympathetic activity via adrenal-targeted GRK2 gene deletion attenuates heart failure progression and improves cardiac function after myocardial infarction, J. Biol. Chem., 285(21):16378-86 (2010).
Lymperopoulos, Beta-arrestin biased agonism/antagonism at cardiovascular seven transmembrane-spanning receptors, Curr. Pharm. Des., 18(2):192-8 (2012).
Ma et al., Novel inhibitors of *Staphylococcus aureus* virulence gene expression and biofilm formation, PLoS One, 7(10):e47255 (2012).
Mushegian et al., The origin and evolution of G protein-coupled receptor kinases, PLoS One, 7(3):e33806 (2012).
Palczewski et al., Nucleoside inhibitors of rhodopsin kinase, Biochemistry, 29(26):6276-82 (1990).
Palczewski et al., Rhodopsin kinase: substrate specificity and factors that influence activity, Biochemistry, 27(7):2306-13 (1988).
Pfefferkorn et al., Substituted pyrazoles as hepatoselective HMG-CoA reductase inhibitors: discovery of (3R,5R)-7-[2-(4-fluorophenyl)-4-isopropyl-5-(4-methyl-benzylcarbamoyl)-2H-pyrazol-3-yl]-3,5-dihydroxyheptanoic acid (PF-3052334) as a candidate for the treatment of hypercholesterolemia, J. Med. Chem., 51(1):31-45 (2008).
Pitcher et al., G protein-coupled receptor kinases, Annu. Rev. Biochem., 67:653-92 (1998).
Raake et al., AAV6.βARKct cardiac gene therapy ameliorates cardiac function and normalizes the catecholaminergic axis in a clinically relevant large animal heart failure model, Eur. Heart J., 34(19):1437-47 (2013).
Raake et al., G protein-coupled receptor kinase 2 ablation in cardiac myocytes before or after myocardial infarction prevents heart failure, Circ. Res., 103(4):413-22 (2008).
Reiter et al., Molecular mechanism of β-arrestin-biased agonism at seven-transmembrane receptors, Annu. Rev. Pharmacol. Toxicol., 52:179-97 (2012).
Rengo et al., Myocardial adeno-associated virus serotype 6-betaARKct gene therapy improves cardiac function and normalizes the neurohormonal axis in chronic heart failure, Circulation, 119(1):89-98 (2009).
Rockman et al., Expression of a beta-adrenergic receptor kinase 1 inhibitor prevents the development of myocardial failure in gene-targeted mice, Proc. Natl. Acad. Sci. USA, 95(12):7000-5 (1998).
Sarver et al., Thermodynamic and structure guided design of statin based inhibitors of 3-hydroxy-3-methylglutaryl coenzyme A reductase, J. Med. Chem., 51(13):3804-13 (2008).
Sehon et al., Potent, selective and orally bioavailable dihydropyrimidine inhibitors of Rho kinase (ROCK1) as potential therapeutic agents for cardiovascular diseases, J. Med. Chem., 51(21):6631-4 (2008).
Setyawan et al., Inhibition of protein kinases by balanol: specificity within the serine/threonine protein kinase subfamily, Mol. Pharmacol., 56(2):370-6 (1999).
Shah et al., In vivo ventricular gene delivery of a beta-adrenergic receptor kinase inhibitor to the failing heart reverses cardiac dysfunction, Circulation, 103(9):1311-6 (2001).
Shou et al., A novel approach to perform metabolite screening during the quantitative LC-MS/MS analyses of in vitro metabolic stability samples using a hybrid triple-quadrupole linear ion trap mass spectrometer, J. Mass. Spectrom., 40(10):1347-56 (2005).
Sindac et al., Novel inhibitors of neurotropic alphavirus replication that improve host survival in a mouse model of acute viral encephalitis, J. Med. Chem., 55(7):3535-45 (2012).
Sindac et al., Optimization of novel indole-2-carboxamide inhibitors of neurotropic alphavirus replication, J. Med. Chem., 56(22):9222-41 (2013).

(56) References Cited

OTHER PUBLICATIONS

Sun et al., Inhibitor of streptokinase gene expression improves survival after group A *Streptococcus* infection in mice, Proc. Natl. Acad. Sci. USA, 109(9):3469-74 (2012).

Tesmer et al., Structure of human G protein-coupled receptor kinase 2 in complex with the kinase inhibitor balanol, J. Med. Chem., 53(4):1867-70 (2010).

Thal et al., Molecular mechanism of selectivity among G protein-coupled receptor kinase 2 inhibitors, Mol. Pharmacol., 80(2):294-303 (2011).

Thal et al., Paroxetine is a direct inhibitor of g protein-coupled receptor kinase 2 and increases myocardial contractility, ACS Chem. Biol., 7(11):1830-9 (2012).

Ungerer et al., Altered expression of beta-adrenergic receptor kinase and beta 1-adrenergic receptors in the failing human heart, Circulation, 87(2):454-63 (1993).

Ungerer et al., Expression of beta-arrestins and beta-adrenergic receptor kinases in the failing human heart, Circ. Res., 74(2):206-13 (1994).

Vinge et al., Substrate specificities of g protein-coupled receptor kinase-2 and -3 at cardiac myocyte receptors provide basis for distinct roles in regulation of myocardial function, Mol. Pharmacol., 72(3):582-91 (2007).

White et al., Preservation of myocardial beta-adrenergic receptor signaling delays the development of heart failure after myocardial infarction, Proc. Natl. Acad. Sci. USA, 97(10):5428-33 (2000).

Winstel et al., Peptide inhibitors of G protein-coupled receptor kinases, Biochem. Pharmacol., 70(7):1001-8 (2005).

Yestrepsky et al., Novel inhibitors of bacterial virulence: development of 5,6-dihydrobenzo[h]quinazolin-4(3H)-ones for the inhibition of group A streptococcal streptokinase expression, Bioorg. Med. Chem., 21(7):1880-97 (2013).

Yu et al., Examination of the pharmacokinetics of active ingredients of ginger in humans, AAPS J., 13(3):417-26 (2011).

Zheng et al., In vitro metabolism of 17-(dimethylaminoethylamino)-17-demethoxygeldanamycin in human liver microsomes, Drug Metab. Dispos., 39(4):627-35 (2011).

\* cited by examiner

A)

B)

C)

D)

G PROTEIN-COUPLED RECEPTOR KINASE 2 INHIBITORS AND METHODS FOR USE OF THE SAME

CROSS-REFERENCE TO RELATED APPLICATION

The benefit under 35 U.S.C. § 119(e) of U.S. Provisional Patent Application Ser. No. 62/034,906 filed Aug. 8, 2014, is hereby claimed, and the disclosure thereof is hereby incorporated herein by reference

STATEMENT OF GOVERNMENT SUPPORT

This invention was made with government support under HL071818 and HL086865 awarded by the National Institutes of Health. The Government has certain rights in the invention.

BACKGROUND

Technical Field

The present disclosure relates to novel, small molecule inhibitors for G protein-coupled receptor kinase 2 ("GRK2"), and methods of using the small molecules to inhibit GRK2 for the treatment of heart disease and hypertension.

Description of Related Technology

Eukaryotic cells regulate the strength and duration of signaling cascades, and therefore, must rapidly adapt to changes in their extracellular environment. G protein-coupled receptors ("GPCRs") are the largest class of receptors in humans, and regulate nearly all aspects of eukaryotic cell physiology. GPCR activity is controlled via the phosphorylation of serine and threonine residues in GPCR cytoplasmic tails and loops by G protein-coupled receptor kinases (GRKs) (see Gurevich et al., Pharmacol Ther 133: 40-69 (2012); Pitcher et al. Annu Rev Biochem 67:653-692 (1998)). The phosphorylated GPCRs recruit arrestins (see Gurevich and Gurevich Pharmacol Ther 110:465-502 (2006)), which uncouple the GPCRs from G proteins, target the receptors to clathrin-coated pits for endocytosis, and serve as adaptors for other signaling pathways (see Claing et al., Prog Neurobiol 66:61-79 (2002); Lymperopoulos Curr Pharm Des 18:192-198 (2012); Reiter et al. Annu Rev Pharmacol Toxical 52:179-197 (2012)).

GRKs can be classified in one of three subfamilies based on gene structure and homology. The vertebrate-specific GRK1 subfamily includes GRK1 (rhodopsin kinase) and 7, which are expressed in the rod and cone cells of the retina. The GRK2 subfamily, which includes GRK2 and GRK3, are Gβγ-dependent and play important roles in the heart and olfactory neurons, respectively. In particular, GRK2 phosphorylates activated β-adrenergic receptors, thereby preventing overstimulation of cAMP-dependent signaling (see, e.g., Diviani et al. J Biol Chem 271:5049-5058 (1996); Hausdorff et al., Symp Soc Exp Biol 44:225-240 (1990); Lefkowitz et al., Trends Phamracol Sci 11:190-194 (1990)). The GRK4 subfamily includes GRK4, 5, and 6. GRK5 and 6 are ubiquitously expressed. GRK5 plays an important role in heart function, albeit distinct from GRK2. All GRKs specifically recognize and phosphorylate only activated GPCRs, and phosphorylate peptide substrates derived from the activated receptors with $K_M$ values up to three orders of magnitude higher than for the full length receptor (see Palczewski et al., Biochemistry 27:2306-2313 (1988)), indicating the existence of an allosteric docking site on GRKs.

GRK2 overexpression in the heart is a biomarker for heart failure, and leads to uncoupling of heart function from sympathetic control. In the failing heart, the loss of cardiac output promotes increased levels of circulating catecholamines, resulting in severe uncoupling of βARs and a loss of inotropic reserve (see Eschenhagen Nat Med 14:485-487 (2008)). This uncoupling coincides with a 2-3 fold increase in GRK2 activity accompanied by an increase in both protein and mRNA levels (see Ungerer Circulation 87:454-463 (1993); Ungerer Circ Res 74: 206-213 (1994)). Thus, in chronic heart failure, GRKs become overexpressed and are linked to disease progression. Studies in mice overexpressing GRK2 in the heart show attenuation of isoproterenol (Iso)-stimulated contractility, reduced cAMP levels, and impaired cardiac function (see Koch et al., Science 268:1350-1353 (1995)), likely through desensitization of cardiac $β_1$-adrenergic receptors (see Vinge et al. Mol Pharmacol 72:582-591 (2007)). Therefore, inhibition of GRK2 function could be beneficial during heart failure (see Hata et al., J Mol Cell Cardiol 37:11-21 (2004); Lymperopoulos et al., J Biol Chem 285:16378-16386 (2010)). For example, studies in animal models using the GRK2 inhibitory protein βARKct, or with cardiac-specific GRK2 gene deletion, have shown that inhibition of GRK2 or lowering expression improves heart failure outcome (see Raake et al., Eur Heart J, Jan. 19, 2012; Raake et al., Circ Res 103:413-422 (2008); Rengo et al., Circulation 119:89-98 (2009); Rockman et al., Proc Natl Acad Sci USA 95:7000-7005 (1998); Shah et al., Circulation 103:1311-1316 (2001); White et al., Proc Natl Acad Sci USA 97:5428-5433 (2000)).

Because GRK2 overexpression in the heart is a biomarker for heart failure, inhibitors of GRK2 have been developed for the treatment of cardiovascular disease. Polyanionic GRK2 inhibitors, such as heparin and dextran sulfate, however, are nonselective (see Benovic et al., J Biol Chem 264:6707-6710 (1989)). Although the natural product, balanol (FIG. 1A), was found to inhibit GRK2 in the low nanomolar range, is a non-selective inhibitor of the protein kinase A, G and C family (AGC kinases) (see Setyawan et al., Mol Pharmacol 56:370-376 (1999); Tesmer et al., J Med Chem 53:1867-1870 (2010)). Other inhibitors of GRKs have also been described, but these either have poor potency (see Iino et al., J Med Chem 45:2150-2159 (2002), low selectivity (see Winstel et al., Biochem Pharmacol 70:1001-1008 (2005)), or non-drug like properties (see Benovic et al., Science 246:235-240 (1989)). For example, a class of heterocyclic compounds, such as Takeda103 (FIG. 1B), which is selective for the GRK2/3 subfamily (see PCT publication No. WO 2007/034846, incorporated herein by reference in its entirety) have been shown to bind in the active site of the enzyme (see Thal et al., Mol Pharmacol 80:294-303 (2011)). Paroxetine also was found to selectively inhibit GRK2 (FIG. 1C), mediating beneficial responses in animal models, but only exhibits micromolar potency (e.g., ~20 µM) (see Thal et al., ACS Chem Biol 7:1830-1830 (2012)). A family of ROCK inhibitors (e.g., GSK180736A (FIG. 1D)) also act as GRK2 inhibitors (see Goodman et al., J Med Chem 50:6-9 (2007); Sehon et al., J Med Chem 51:6631-6634 (2008)).

Therefore, there is a need for GRK2 inhibitors that exhibit high potency, high selectivity, and good pharmacokinetic properties for the treatment and prevention of cardiac disease.

SUMMARY

One aspect of the disclosure provides a compound of Formula (I), or a pharmaceutically acceptable salt thereof:

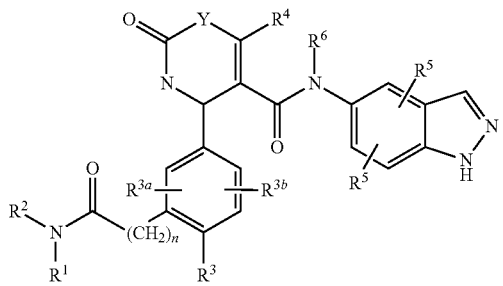

(I)

wherein:
n is 0, 1, or 2;
X and Y are each $N(R^7)$, or one of X and Y is $N(R^7)$ and the other is $CH_2$;
$R^1$ is H, $C_{1-8}$alkyl, $C_{2-8}$alkenyl, $C_{2-8}$alkynyl, $C_{3-8}$ cycloalkyl, $C_{3-8}$ cycloalkenyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;
$R^2$ is $C_{1-8}$alkyl, $C_{2-8}$alkenyl, $C_{3-8}$ cycloalkyl, $C_{3-8}$ cycloalkenyl, $C_{1-4}$ alkylene-cycloalkyl, $C_{0-4}$ alkylene-heterocycloalkyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;
or $R^1$ and $R^2$, together with the nitrogen atom to which they are attached, form a 3-8-membered heterocycloalkyl group;
$R^3$ is H, F, Cl, or $CH_3$;
$R^{3a}$ and $R^{3b}$ are each independently H, F, Cl, or $CH_3$;
$R^4$ is H, $CH_3$, $CF_3$, $CH_2CH_3$, or $CH_2CH_2CH_3$;
each $R^5$ independently is H or F;
$R^6$ is H or $C_{1-6}$ alkyl; and
each $R^7$ independently is H or $C_{1-6}$ alkyl.

In some embodiments, $R^1$ is H. In other embodiments, $R^1$ is $C_{1-8}$alkyl, $C_{2-8}$alkenyl, or $C_{2-8}$alkynyl (e.g., $CH_3$, $CH_2CH_2OH$, or $CH_2CCH$). In yet other embodiments, $R^1$ is $C_{3-8}$ cycloalkyl or $C_{3-8}$ cycloalkenyl. In various embodiments, $R^1$ is $C_{1-4}$ alkylene-aryl, or $C_{1-4}$ alkylene-heteroaryl. In some cases, $R^1$ is $C_{3-8}$ cycloalkylene-aryl or $C_{3-8}$ cycloalkylene-heteroaryl. The aryl can be, e.g., phenyl or naphthyl, and the heteroaryl can be, e.g., pyridyl or quinolinyl.

In some embodiments, $R^2$ is $C_{1-8}$ alkyl. In other embodiments, $R^2$ is $C_{1-4}$ alkyl (e.g., methyl, ethyl, isopropyl, or sec-butyl) or $C_{2-8}$ alkenyl. In yet other embodiments, $R^2$ is $C_{3-8}$ cycloalkyl or $C_{3-8}$ cycloalkenyl. For example, $R^2$ can include

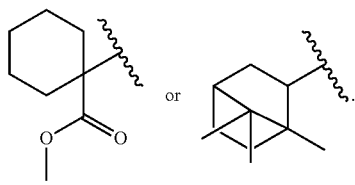 [SMILES: *C1(C(=O)OC)CCCCC1 ; *C1CC2CCC1(C)C2(C)C]

In various embodiments, $R^2$ is $C_{1-4}$ alkylene-cycloalkyl, $C_{0-4}$ alkylene-heterocycloalkyl, $C_{3-8}$ cycloalkylene-aryl or $C_{3-8}$ cycloalkylene-heteroaryl. For example, $R^2$ can include azepanyl, tetrahydropyranyl, morpholinyl, piperidinyl, oxadiazolyl, oxazolyl, pyrazolyl, furanyl, or imidazolyl) In some cases, $R^2$ is $C_{1-4}$ alkylene-aryl or $C_{1-4}$ alkylene-heteroaryl. For example, $R^2$ can comprise

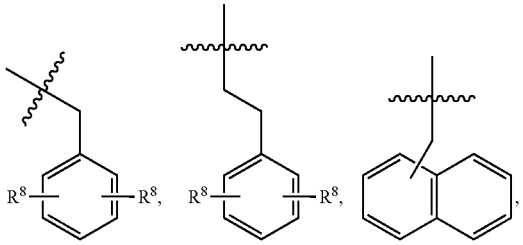

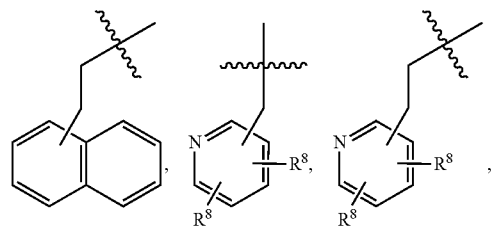

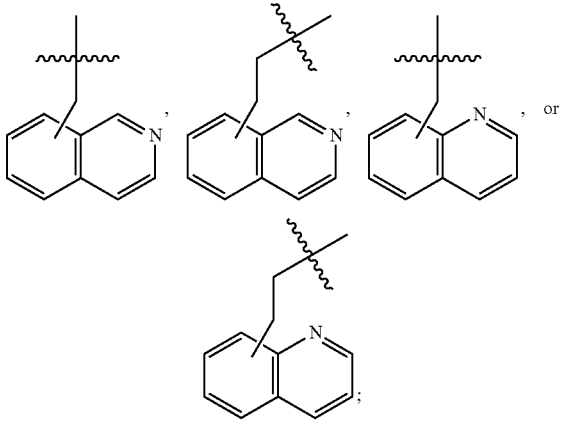

wherein each $R^8$ independently is H, halo, $C_{1-4}$ alkyl, or $C_{1-4}$ alkoxyl.

In some embodiments, each $R^8$ is H. In other embodiments, one $R^8$ is H and one $R^8$ is halo (e.g., F or Cl), $C_{1-4}$ alkyl (e.g., $CH_3$ or $CF_3$), or $C_{1-4}$ alkoxyl (e.g., $OCH_3$ or $OCF_3$). In other embodiments, each $R^8$ is halo (e.g., F or Cl), $C_{1-4}$ alkyl (e.g., $CH_3$ or $CF_3$), or $C_{1-4}$ alkoxyl (e.g., $OCH_3$ or $OCF_3$). In any of these embodiments, each $R^8$ can be ortho. In some embodiments, $R^1$ and $R^2$, together with the nitrogen atom to which they are attached, for a 3-8-membered heterocycloalkyl group, such as a morpholinyl group. For example, $R^2$ can comprise $CH_3$, isopropyl, sec-butyl,

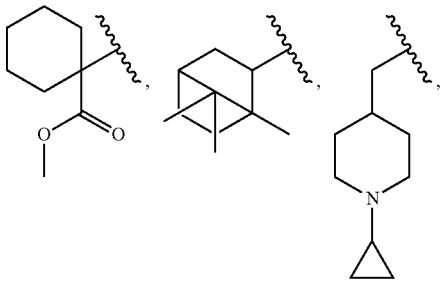

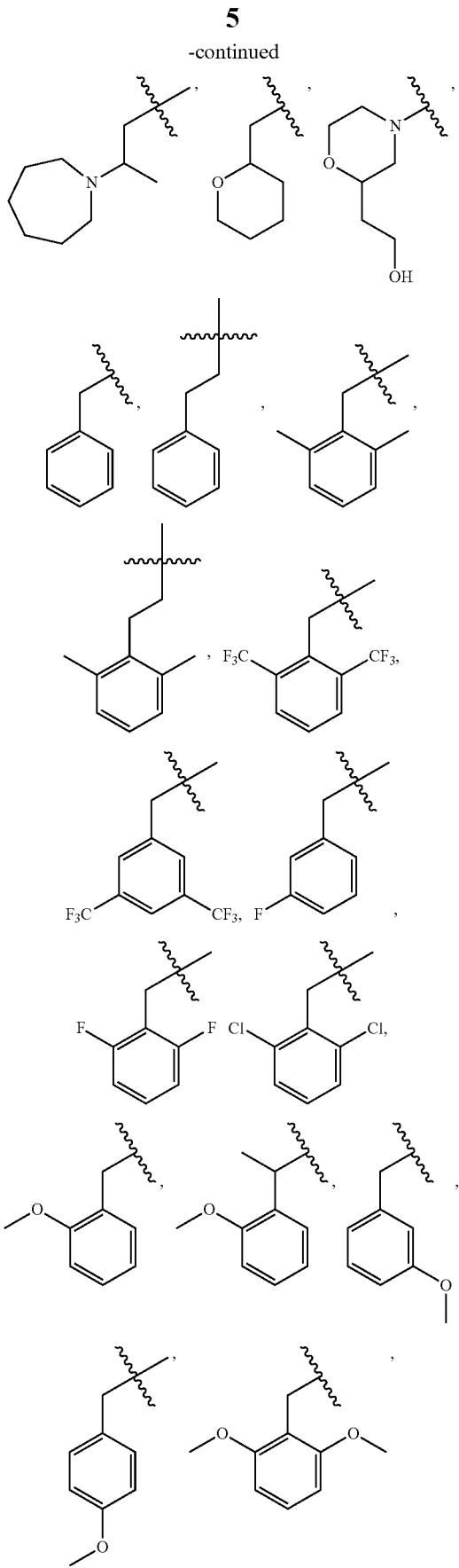

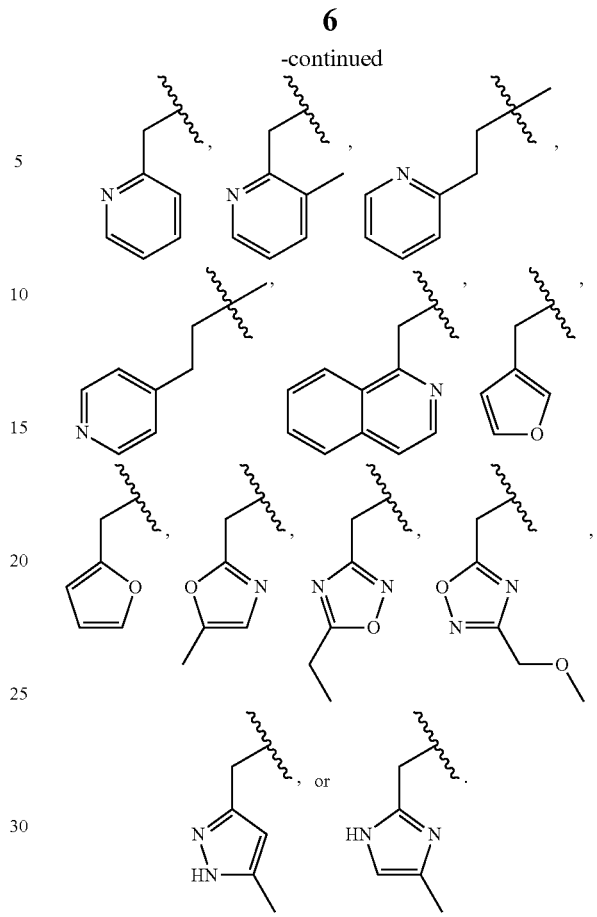

some embodiments, $R^3$ is H, Cl, or $CH_3$. In other embodiments, $R^3$ is F. In some cases, $R^{3a}$ and $R^{3b}$ are H. In other cases, $R^{3a}$ is H, and $R^{3b}$ is F, Cl, or $CH_3$. In various cases, each of $R^{3a}$ and $R^{3b}$ are F, Cl, or $CH_3$.

In some cases, $R^4$ is H, $CH_2CH_3$, or $CH_2CH_2CH_3$. In various cases, $R^4$ is $CH_3$ or $CF_3$.

In some embodiments, each $R^5$ is H. In other embodiments, each $R^5$ is F. In yet other embodiments, one $R^5$ is H and one $R^5$ is F.

In some cases, $R^6$ is H.

In some embodiments, X and Y are each $N(R^7)$. In other embodiments, X is $N(R^7)$ and Y is $CH_2$. In yet other embodiments, X is $CH_2$, and Y is $N(R^7)$. In any of these embodiments, $R^7$ can be H.

In some embodiments, n is 0. In other embodiments, n is 1. In yet other embodiments, n is 2.

For example, the compound of Formula (I) can comprise a structure selected from E01-E38.

Another aspect of the disclosure relates to a pharmaceutical formulation comprising the compound of Formula (I), or a pharmaceutically acceptable salt thereof, as defined herein, and a pharmaceutically acceptable excipient.

Yet another aspect of the invention relates to a method of inhibiting GRK2 in a cell, comprising contacting the cell with a compound Formula (I), or a pharmaceutically acceptable salt thereof, as defined herein, or a pharmaceutical formulation thereof, in an amount effective to inhibit GRK2. In some embodiments, the GRK2 is inhibited with at least 2.0-fold selectivity over GRK5. In some cases, the cell is a myocyte, such as a cardiomyocyte. The contacting can occur, for example, in vivo. In some embodiments, the contacting comprises administering to a subject in need thereof. The subject can suffer from a condition, such as heart disease (e.g., cardiac failure, cardiac hypertrophy, hypertension, or a combination thereof).

Still another aspect of the disclosure relates to a method of treating heart disease in a subject comprising administering to the subject a therapeutically effective amount of a pharmaceutical formulation comprising a compound of Formula (I), or a pharmaceutically acceptable salt thereof, as defined herein.

Further aspects and advantages will be apparent to those of ordinary skill in the art from a review of the following detailed description, taken in conjunction with the drawings. While the inhibitors and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION

Figure 1:
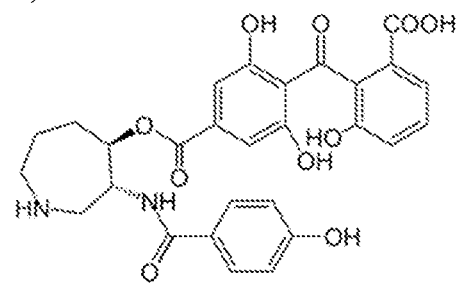
FIG. 1 depicts the chemical structures of the GRK inhibitors (A) balanol, (B) Takeda103, (C) paroxetine, and (D) GSK180736A.
Figure 1:
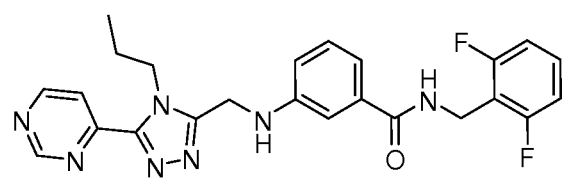
Figure 1:
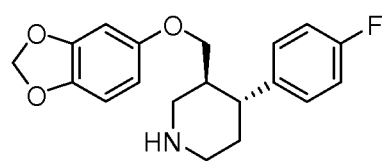
Figure 1:
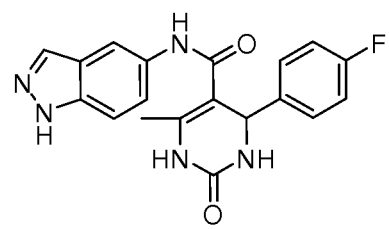

Disclosed herein are novel small molecule inhibitors of GRK2 that demonstrate superior potency and selectivity over other small molecule GRK2 inhibitors (e.g., about 150 times greater potency and about 1800-fold greater selectivity). The GRK2 inhibitors disclosed herein can be used to treat or prevent heart disease (e.g., cardiac failure, cardiac hypertrophy, hypertension), improving the quality of life for afflicted individuals.

The GRK2 inhibitors disclosed herein have a structure of Formula (I)

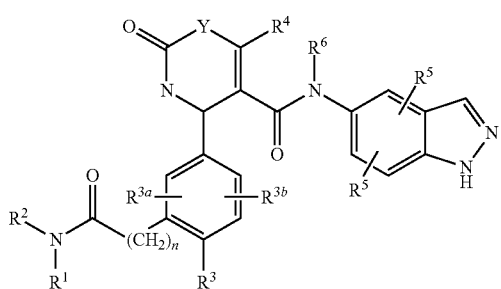

wherein the substituents are as described in detail below.

In various cases, the compounds of Formula (I) selectively inhibit GRK2 over GRK5. Without being bound by any particular theory, the hydrophobic pocket of GRK2 is either larger than GRK5, or can bind a ligand in a more closed conformation. Therefore, compounds having a substituted amide group (e.g., wherein at least one of $R^1$ and $R^2$ is other than hydrogen), such as compounds of Formula (I), favor GRK2 over GRK5. As used herein, a compound of Formula (I) is "selective" for GRK2 over GRK5 if it inhibits GRK2 to a greater extent compared to GRK5. In some cases, the compound of Formula (I) inhibits GRK2 at least 50% more than GRK5 (e.g., at least 1.5-fold), as measured in the assays as described in the Examples section below. In various cases, the selectivity for GRK2 over GRK5 is at least 2.0-fold, or at least 10-fold, or at least 20-fold, or at least 50-fold, or at least 100-fold, or at least 200-fold, or at least 300-fold, or at least 400-fold, or at least 500-fold, or at least 600-fold, or at least 700-fold, or at least 800-fold, or at least 900-fold, or at least 1000-fold, or at least 1100-fold, or at least 1200-fold, or at least 1300-fold, or at least 1400-fold, or at least 1500-fold, or at least 1600-fold, or at least 1700-fold, or at least 1800-fold, or at least 1900-fold, or at least 2000-fold. In some cases, the compounds of Formula (I) exhibit a selectivity of at least 700-fold, or at least 800-fold, or at least 900-fold, or at least 1000-fold, or at least 1100-fold, or at least 1200-fold, or at least 1300-fold, or at least 1400-fold, or at least 1500-fold, or at least 1600-fold, or at least 1700-fold, or at least 1800-fold, or at least 1900-fold, or at least 2000-fold.

In various cases, the compounds of Formula (I) inhibit GRK2 with an $IC_{50}$ up to about 15 μM. In some embodiments, the compounds of Formula (I) have an $IC_{50}$ value for GRK2 of less than about 10 μM, or less than about 5 μM, or less than about 1 μM, or less than about 0.5 μM, or less than about 0.4 μM, or less than about 0.3 μM, or less than about 0.2 μM, or less than about 0.1 μM, or less than about 0.05 μM. In various cases, the $IC_{50}$ value of the compound of Formula (I) is about 0.05 μM to about 15 μM, or about 0.05 μM to about 0.4 μM, or about 0.05 μM to about 0.1 μM.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. When the alkyl group is substituted, the substituent can occur on any carbon of the alkyl chain.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_2$-$C_7$ alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "alkylene" refers to an alkyl group having a substituent. For example, the term "alkylene-aryl" refers to an alkyl group substituted with an aryl group. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated, bridged, or fused to another cycloalkyl group, a heterocycloalkyl group, an aryl group and/or a heteroaryl group.

As used herein, the term "heterocycloalkyl" is defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylene-aryl, and alkylene-heteroaryl. The heterocycloalkyl groups described herein can be isolated, bridged, or fused to another heterocycloalkyl group, a cycloalkyl group, an aryl group and/or a heteroaryl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "alkoxy" or "alkoxyl" as used herein refers to a "—O-alkyl" group. The alkoxy or alkyoxl group can be unsubstituted or substituted.

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, ether, polyether, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds (e.g., a GRK2 inhibitor or combination of GRK2 inhibitors) that ameliorates, attenuates or eliminates one or more symptoms of a particular disease or condition (e.g., heart disease), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients or subjects are mammals (e.g., humans). The terms patient and subject includes males and females.

As used herein, the term "pharmaceutically acceptable" means that the referenced substance, such as a compound of the present invention, or a formulation containing the compound, or a particular excipient, are safe and suitable for administration to a patient or subject. The term "pharmaceutically acceptable carrier" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

Small Molecule GRK2 Inhibitors

Provided herein is a compound of Formula (I), or a pharmaceutically acceptable salt thereof:

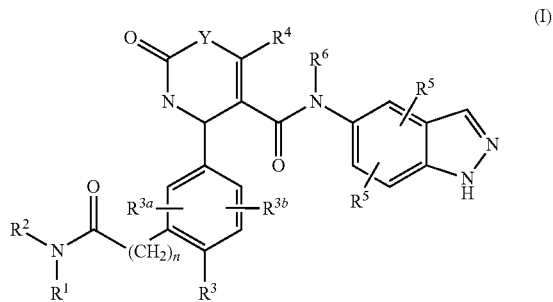

wherein:

n is 0, 1, or 2;

X and Y are each N(R$^7$), or one of X and Y is N(R$^7$) and the other is CH$_2$;

R$^1$ is H, C$_{1-8}$alkyl, C$_{2-8}$alkenyl, C$_{2-8}$alkynyl, C$_{3-8}$ cycloalkyl, C$_{3-8}$ cycloalkenyl, C$_{1-4}$ alkylene-aryl, C$_{1-4}$ alkylene-heteroaryl, C$_{3-8}$ cycloalkylene-aryl, or C$_{3-8}$ cycloalkylene-hetero aryl;

R$^2$ is C$_{1-8}$alkyl, C$_{2-8}$alkenyl, C$_{3-8}$ cycloalkyl, C$_{3-8}$ cycloalkenyl, C$_{1-4}$ alkylene-cycloalkyl, C$_{0-4}$ alkylene-heterocycloalkyl, C$_{1-4}$ alkylene-aryl, C$_{1-4}$ alkylene-heteroaryl, C$_{3-8}$ cycloalkylene-aryl, or C$_{3-8}$ cycloalkylene-heteroaryl;

or $R^1$ and $R^2$, together with the nitrogen atom to which they are attached, form a 3-8-membered heterocycloalkyl group;

$R^3$ is H, F, Cl, or $CH_3$;

$R^{3a}$ and $R^{3b}$ are each independently H, F, Cl, or $CH_3$;

$R^4$ is H, $CH_3$, $CF_3$, $CH_2CH_3$, or $CH_2CH_2CH_3$;

each $R^5$ independently is H or F;

$R^6$ is H or $C_{1-6}$ alkyl; and each $R^7$ independently is H or $C_{1-6}$ alkyl.

In some embodiments, $R^1$ is H. In various embodiments, $R^1$ is $C_{1-8}$alkyl, for example, $C_{1-4}$ alkyl (e.g., methyl, ethyl, n-propyl, isopropyl, n-butyl, isobutyl, sec-butyl, or tert-butyl), or $C_{5-8}$ alkyl (e.g., $C_5$ alkyl or $C_6$ alkyl or $C_7$ alkyl or $C_8$ alkyl). In some embodiments, the alkyl group is substituted (e.g., $CH_2CH_2OH$). In some cases, $R^1$ is $C_{2-8}$ alkenyl, for example, $C_{2-4}$alkenyl (e.g., $C_2$ alkenyl or $C_3$ alkenyl or $C_4$ alkenyl) or $C_{5-8}$alkenyl (e.g., $C_5$ alkenyl or $C_6$ alkenyl or $C_7$ alkenyl or $C_8$ alkenyl). The $C_{2-8}$ alkenyl can be monounsaturated. In various cases, $R^1$ is $C_{2-8}$ alkenyl (e.g., $CH_2CCH$), In some embodiments, $R^1$ is $C_{3-8}$ cycloalkyl (e.g., cyclopropyl, cyclobutyl, cyclopentyl, cyclohexyl) or cycloheptyl) or $C_{3-8}$ cycloalkenyl (e.g., cyclopentenyl, cyclohexenyl, or cycloheptenyl). The cycloalkyl and cycloalkenyl can be an isolated hydrocarbon ring or fused to a cycloalkyl group, a heterocycloalkyl group, an aryl group, a heteroaryl group, or a combination thereof. In some embodiments, $R^1$ is $C_{1-4}$ alkylene-aryl (e.g., $CH_2$-aryl, $CH_2CH_2$-aryl, or $CH_2CH_2CH_2$-aryl) or $C_{1-4}$ alkylene-heteroaryl (e.g., $CH_2$-heteroaryl, $CH_2CH_2$-heteroaryl, or $CH_2CH_2CH_2$-heteroaryl). In some cases, $R^1$ is $C_{3-8}$ cycloalkylene-aryl (e.g., cyclopropylene-aryl, cyclobutylene-aryl, cyclopentylene-aryl, or cyclohexylene-aryl) or $C_{3-8}$ cycloalkylene-heteroaryl (e.g., cyclopropylene-heteroaryl, cyclobutylene-heteroaryl, cyclopentylene-heteroaryl, or cyclohexylene-heteroaryl). In any of the embodiments disclosed herein, the aryl can be, for example, phenyl, naphthyl, tetrahydronaphthyl, phenanthrenyl, indanyl, indenyl, anthracenyl, and fluorenyl. In some cases, the aryl is phenyl or naphthyl. In any of the embodiments disclosed herein, the heteroaryl can be, for example, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl or benzothiazolyl. In some cases, the heteroaryl is pyridyl or quinolinyl. The aryl group or heteroaryl group can be substituted or unsubstituted. In some embodiments, the aryl group or heteroaryl group is substituted with one or more of halo (e.g., fluoro, chloro, bromo, or a combination thereof), $C_{1-4}$ alkyl (e.g., methyl, trifluoromethyl, ethyl, propyl, isopropyl, n-butyl, isobutyl, sec-butyl, tert-butyl, or a combination thereof), $C_{1-4}$ alkoxyl (e.g., methoxyl, trifluoromethoxyl, ethoxyl, n-propoxyl, isopropoxyl, n-butoxyl, isobutoxyl, sec-butoxyl, tert-butoxyl, or a combination thereof), or a combination thereof.

In various embodiments, $R^2$ is $C_{1-8}$alkyl, for example, $C_{1-4}$ alkyl (e.g., methyl, ethyl, n-propyl, isopropyl, n-butyl, isobutyl, sec-butyl, or tert-butyl) or $C_{5-8}$ alkyl (e.g., $C_5$ alkyl or $C_6$ alkyl or $C_7$ alkyl or $C_8$ alkyl). In some cases, $R^2$ is $C_{2-8}$ alkenyl, for example, $C_{2-4}$alkenyl (e.g., $C_2$ alkenyl or $C_3$ alkenyl or $C_4$ alkenyl) or $C_{5-8}$alkenyl (e.g., $C_5$ alkenyl or $C_6$ alkenyl or $C_7$ alkenyl or $C_8$ alkenyl). The $C_{2-8}$ alkenyl can be monounsaturated. In some embodiments, $R^2$ is $C_{3-8}$ cycloalkyl (e.g., cyclopropyl, cyclobutyl, cyclopentyl, cyclohexyl, cycloheptyl,

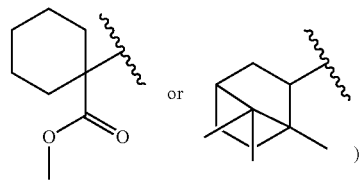 [SMILES: *C1(C(=O)OC)CCCCC1 ; *C1CC2CCC1(C)C2(C)C]

or $C_{3-8}$ cycloalkenyl (e.g., cyclopentenyl, cyclohexenyl, or cycloheptenyl). The cycloalkyl and cycloalkenyl can be an isolated hydrocarbon ring or fused to a cycloalkyl group, a heterocycloalkyl group, an aryl group, a heteroaryl group, or a combination thereof. In various cases, $R^2$ is $C_{1-4}$ alkylene-cycloalkyl or $C_{0-4}$ alkylene-heterocycloalkyl (e.g., azepanyl, tetrahydropyranyl, morpholinyl, piperidinyl) In some embodiments, $R^2$ is $C_{1-4}$ alkylene-aryl (e.g., $CH_2$-aryl, $CH_2CH_2$-aryl, or $CH_2CH_2CH_2$-aryl) or $C_{1-4}$ alkylene-heteroaryl (e.g., $CH_2$-heteroaryl, $CH_2CH_2$-heteroaryl, or $CH_2CH_2CH_2$-heteroaryl). In some cases, $R^2$ is $C_{3-8}$ cycloalkylene-aryl (e.g., cyclopropylene-aryl, cyclobutylene-aryl, cyclopentylene-aryl, or cyclohexylene-aryl) or $C_{3-8}$ cycloalkylene-heteroaryl (e.g., cyclopropylene-heteroaryl, cyclobutylene-heteroaryl, cyclopentylene-heteroaryl, or cyclohexylene-heteroaryl). In any of the embodiments disclosed herein, the aryl can be, for example, phenyl, naphthyl, tetrahydronaphthyl, phenanthrenyl, indanyl, indenyl, anthracenyl, and fluorenyl. In some cases, the aryl is phenyl or naphthyl. In any of the embodiments disclosed herein, the heteroaryl can be, for example, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl or benzothiazolyl. In some cases, the heteroaryl is pyridyl or quinolinyl. In various embodiments, the heteroaryl can include oxadiazolyl, oxazolyl, pyrazolyl, furanyl, or imidazolyl. The aryl group or heteroaryl group can be substituted or unsubstituted. In some embodiments, the aryl group or heteroaryl group is substituted with one or more of halo (e.g., fluoro, chloro, bromo, or a combination thereof), $C_{1-4}$ alkyl (e.g., methyl, trifluoromethyl, ethyl, propyl, isopropyl, n-butyl, isobutyl, sec-butyl, tert-butyl, or a combination thereof), $C_{1-4}$ alkoxyl (e.g., methoxyl, trifluoromethoxyl, ethoxyl, n-propoxyl, isopropoxyl, n-butoxyl, isobutoxyl, sec-butoxyl, tert-butoxyl, or a combination thereof), or a combination thereof. For example, $R^2$ can comprise

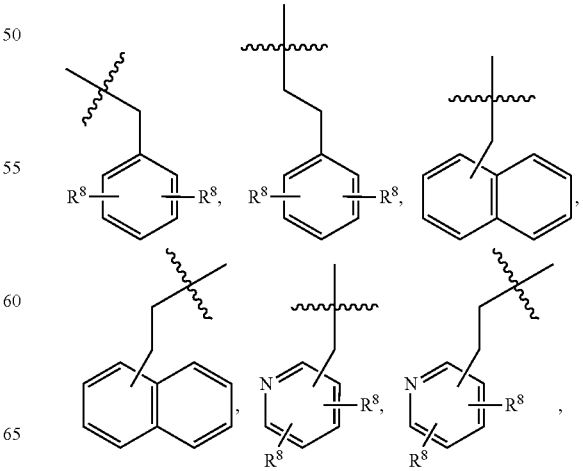

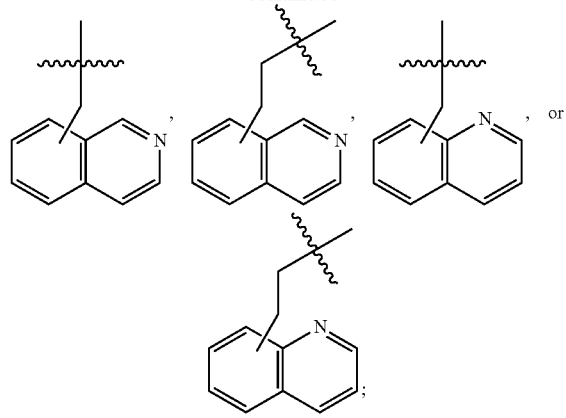

wherein each $R^8$ independently is H, halo, $C_{1-4}$ alkyl, or $C_{1-4}$ alkoxyl. In some embodiments, each $R^8$ is H. In other embodiments, one $R^8$ is H and one $R^8$ is selected from halo (e.g., F or Cl), $C_{1-4}$ alkyl (e.g., $CH_3$ or $CF_3$), and $C_{1-4}$ alkoxyl (e.g., $OCH_3$ or $OCF_3$). In some cases, each $R^8$ is halo (e.g., F or Cl), or $C_{1-4}$ alkyl (e.g., $CH_3$ or $CF_3$), or $C_{1-4}$ alkoxyl (e.g., $OCH_3$ or $OCF_3$). In some of these embodiments, each $R^8$ is ortho to the alkylene chain. In some cases, each $R^8$ is meta to the alkylene chain. In various of these embodiments, one $R^8$ is ortho to the alkylene chain and the other $R^8$ is para to the alkylene chain. In some cases, one $R^8$ is ortho to the alkylene chain and the other $R^8$ is meta to the alkylene chain. In some embodiments, $R^1$ and $R^2$, together with the nitrogen atom to which they are attached, for a 3-8-membered heterocycloalkyl group, such as a morpholinyl group. In various cases, $R^2$ can comprise a structure selected from $CH_3$, isopropyl, sec-butyl,

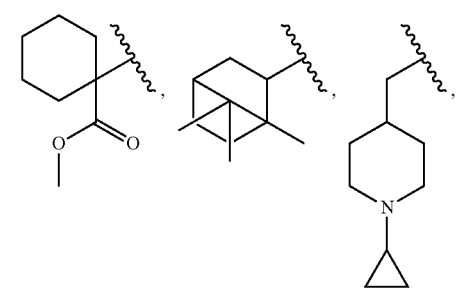

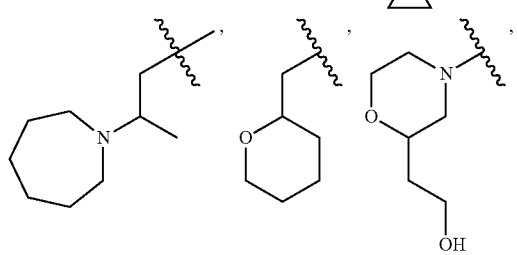

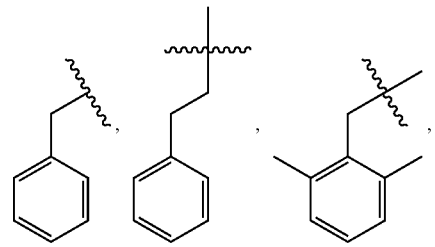

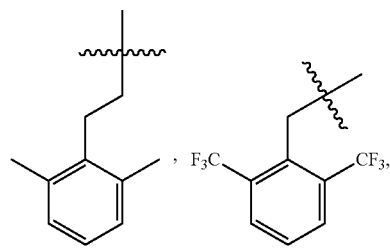

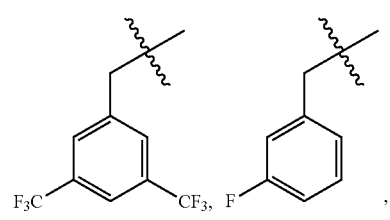

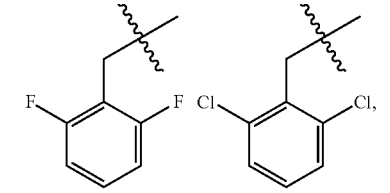

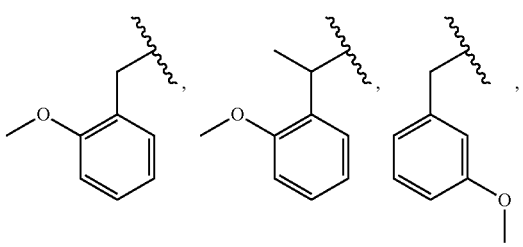

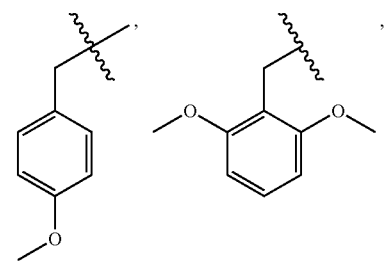

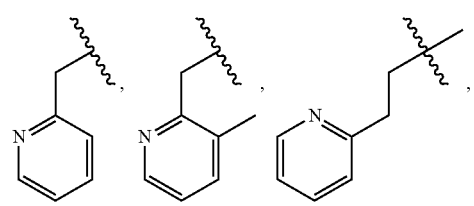

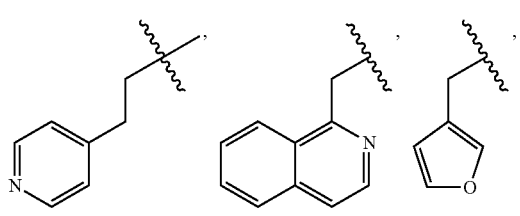

15

-continued

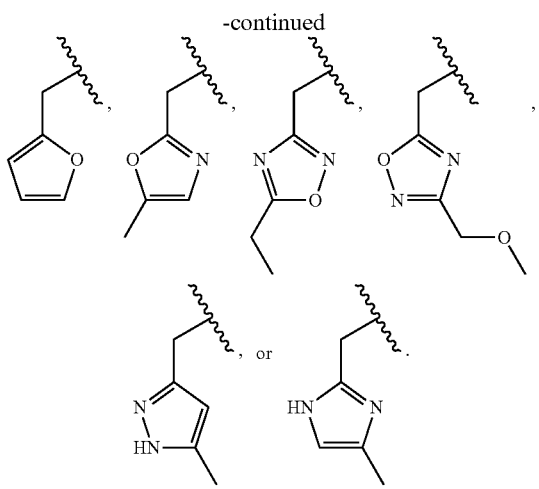

In some embodiments, $R^3$ is H, Cl, or $CH_3$. In other embodiments, $R^3$ is F.

In some embodiments, each of $R^{3a}$ and $R^{3b}$ are H. In other embodiments, $R^{3a}$ is H and $R^{3b}$ is F, Cl, or $CH_3$. In some cases, each of $R^{3a}$ and $R^{3b}$ are F, Cl, or $CH_3$.

In various embodiments, $R^4$ is H. In some embodiments, $R^4$ is $CH_3$, or $CH_2CH_3$, or $CH_2CH_2CH_3$.

In some embodiments, each $R^5$ is H or each $R^5$ is F. In various embodiments, one $R^5$ is H and one $R^5$ is F.

In some cases, $R^6$ is H. In other cases, $R^6$ is $C_{1-6}$ alkyl (e.g., $CH_3$, $CH_2CH_3$, or $CH_2CH_2CH_3$).

In various embodiments, X and Y are each $N(R^7)$. In some embodiments, X is $N(R^7)$ and Y is $CH_2$. In other embodiments, X is $CH_2$, and Y is $N(R^7)$. In any of these embodiments, $R^7$ can be H. In some cases, $R^7$ can be $C_{1-6}$ alkyl (e.g., $CH_3$, $CH_2CH_3$, or $CH_2CH_2CH_3$).

In some embodiments, n is 0. In other embodiments, n is 1. In some cases, n is 2.

Also provided herein is a compound of Formula (I'), or a pharmaceutically acceptable salt thereof:

(I')

[Structure of Formula (I')]

wherein:
$R^1$ is H, $C_{1-8}$alkyl, $C_{2-8}$alkenyl, $C_{3-8}$ cycloalkyl, $C_{3-8}$ cycloalkenyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;

$R^2$ is $C_{1-8}$alkyl, $C_{2-8}$alkenyl, $C_{3-8}$ cycloalkyl, $C_{3-8}$ cycloalkenyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;

16

$R^3$ is H, F, Cl, or $CH_3$;
$R^6$ is H or $C_{1-6}$ alkyl; and
each $R^7$ independently is H or $C_{1-6}$ alkyl.

In some of these embodiments, $R^1$ is H. In various embodiments, $R^3$ is F. In some cases, $R^6$ is H. In other embodiments, each $R^7$ is H. In any of these embodiments, $R^2$ is as defined above.

In some embodiments, the compound of Formula (I) is a structure selected from:

E01

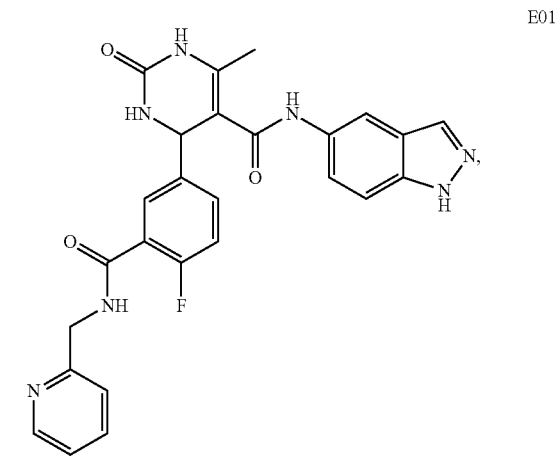

E02

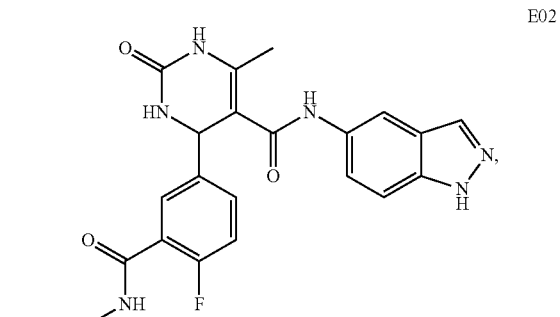

E03

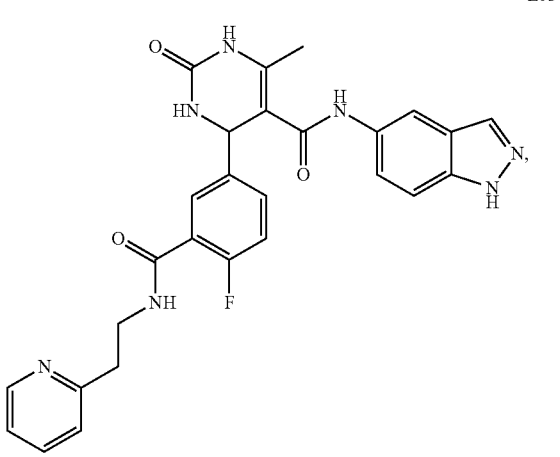

E04
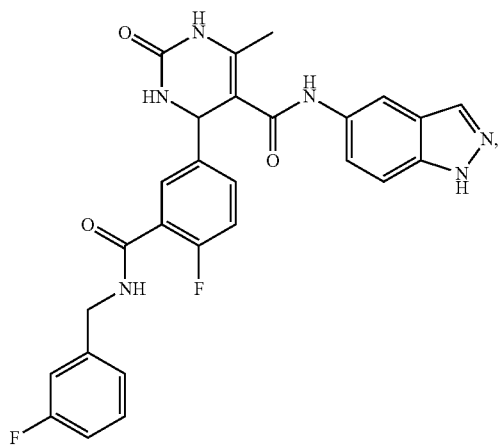
E05
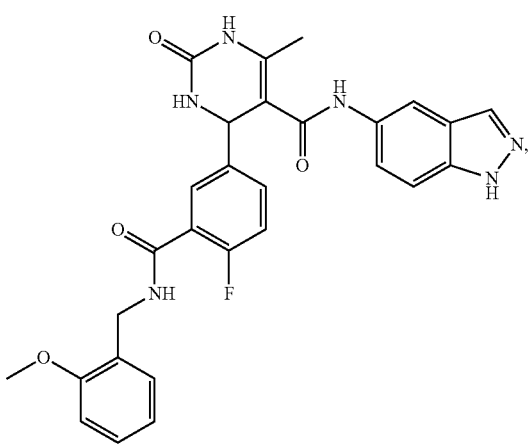
E06
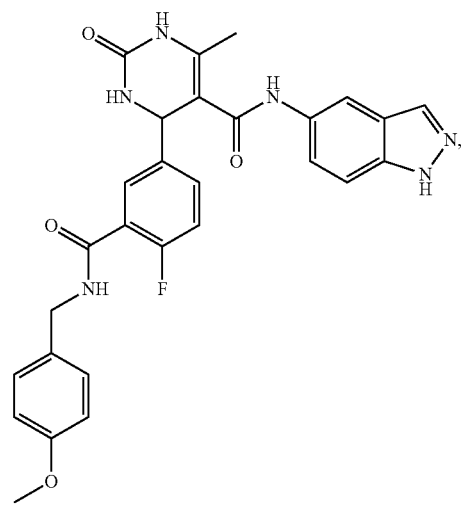
E07
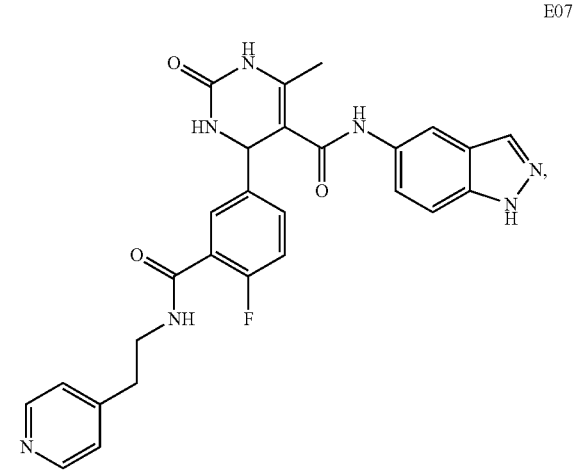
E08
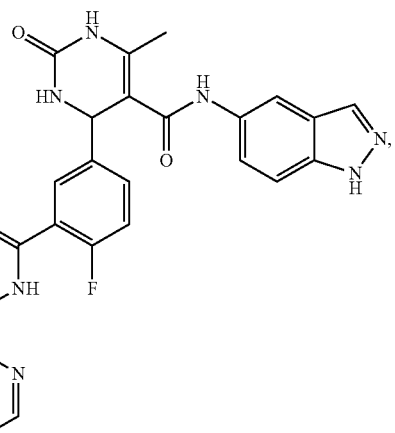
E09
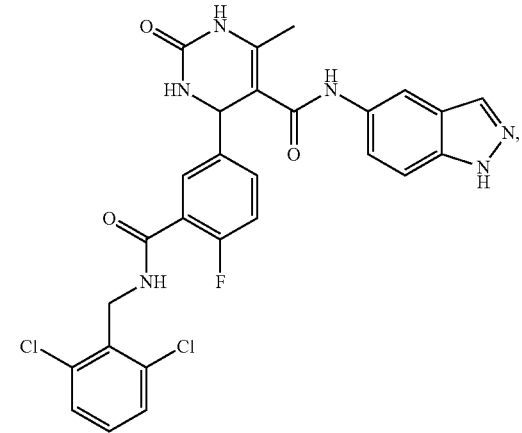

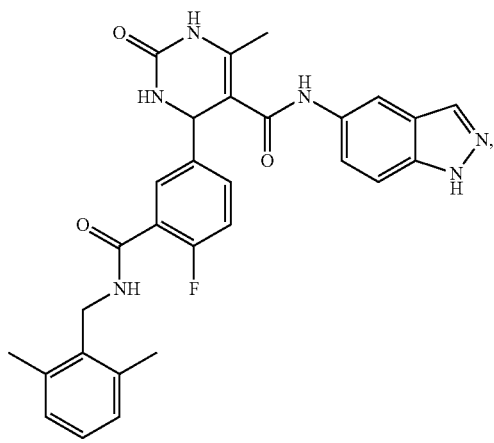
E10
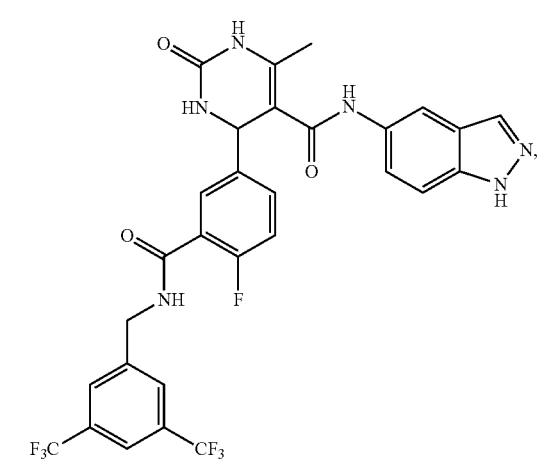
E13
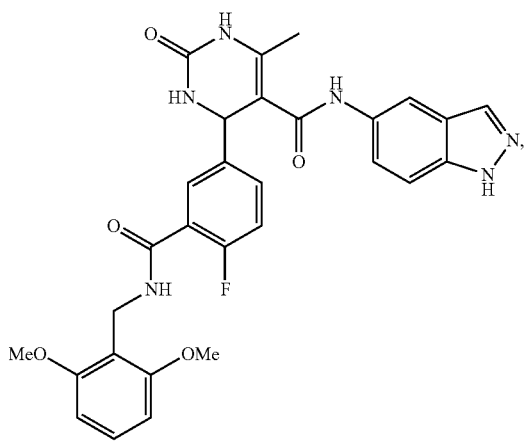
E11
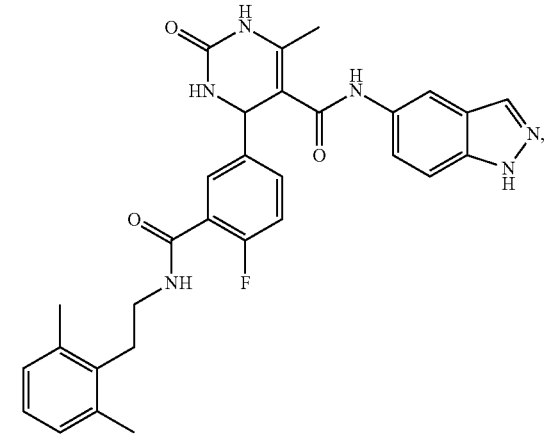
E14
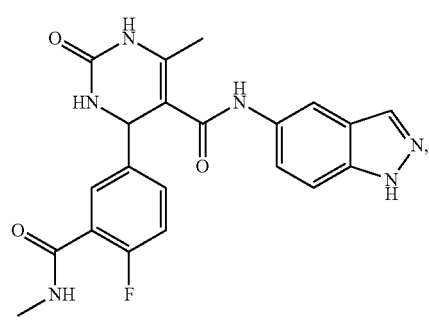
E12
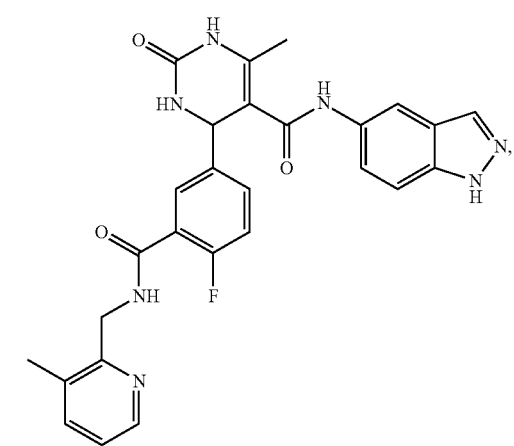
E15

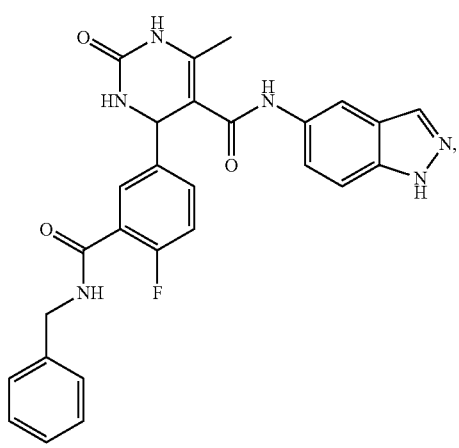
E16
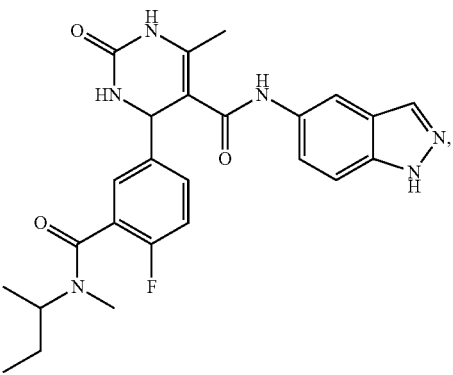
E19
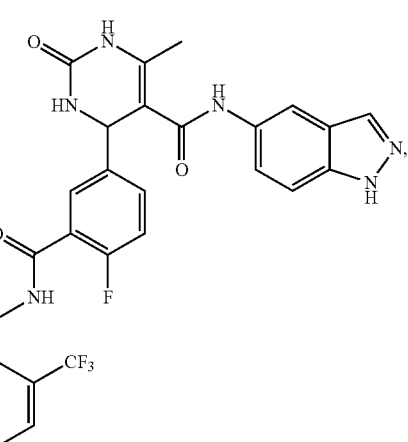
E17
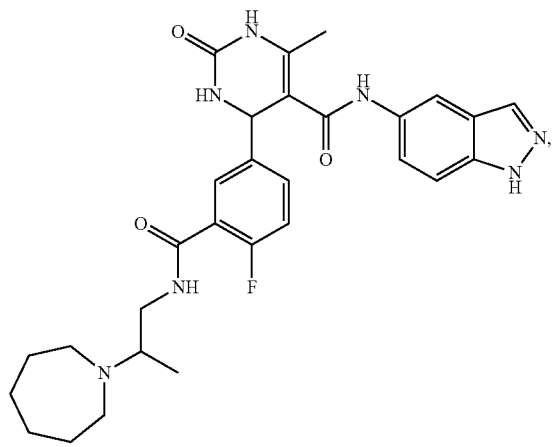
E20
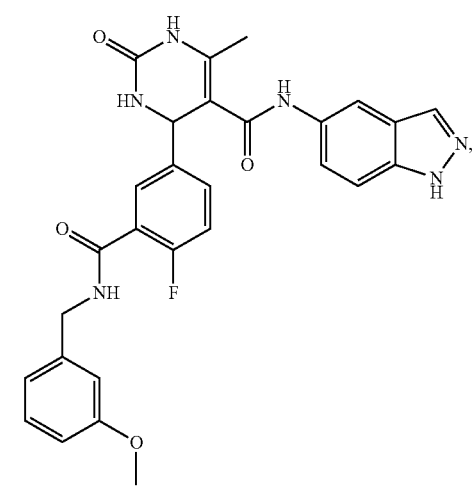
E18
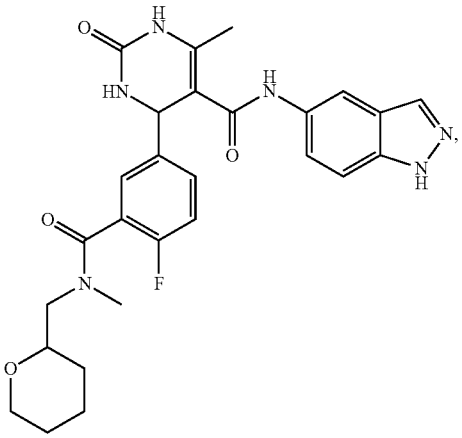
E21

E22
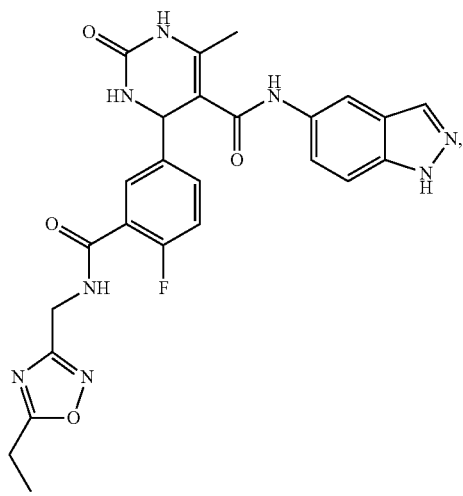
E23
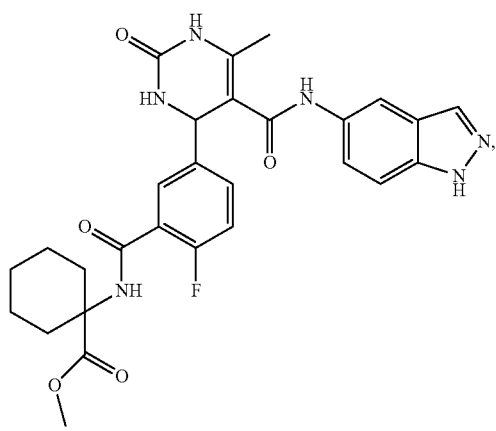
E24
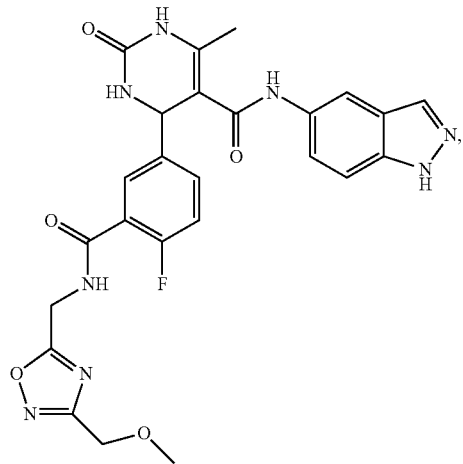
E25
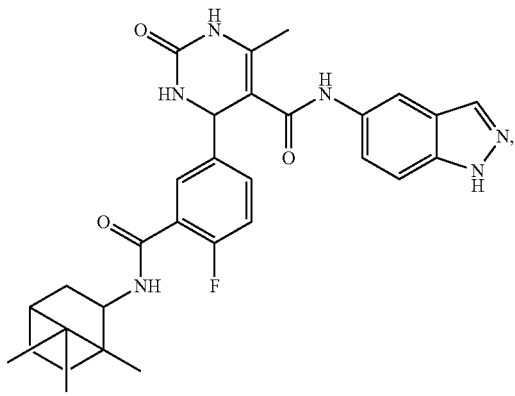
E26
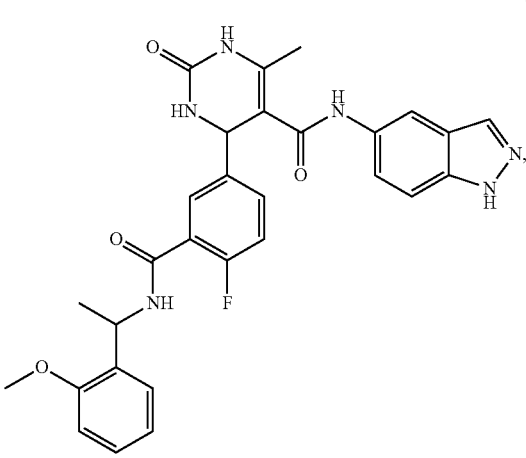
E27

E28
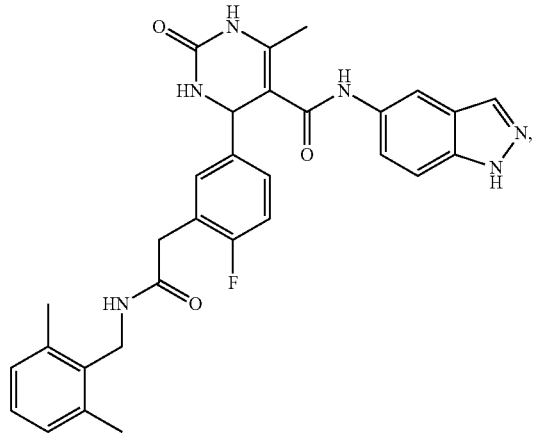
E31
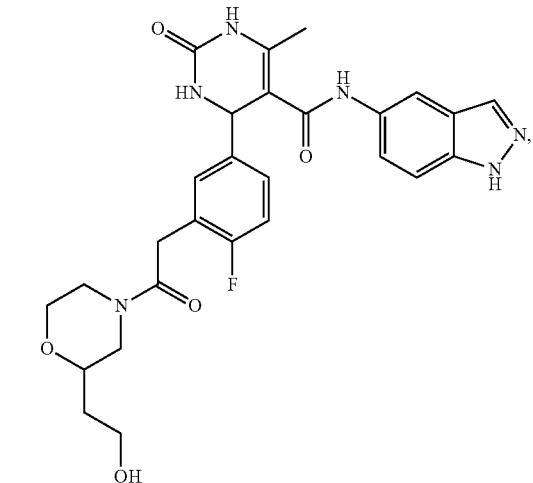
E29
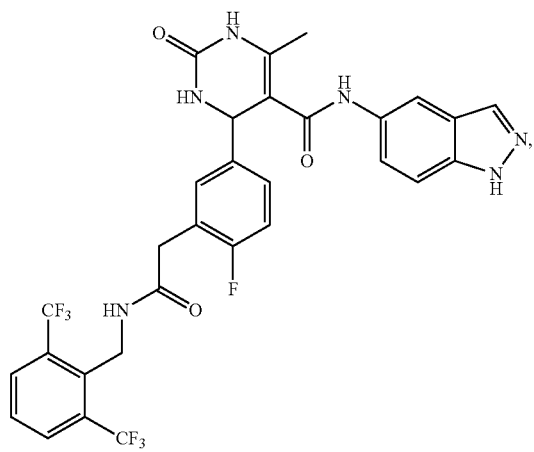
E32
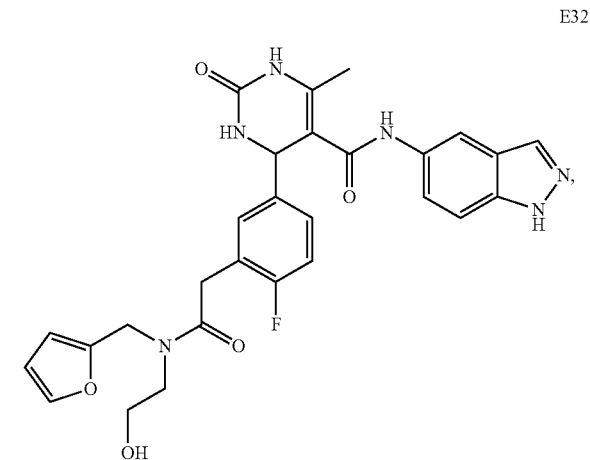
E30
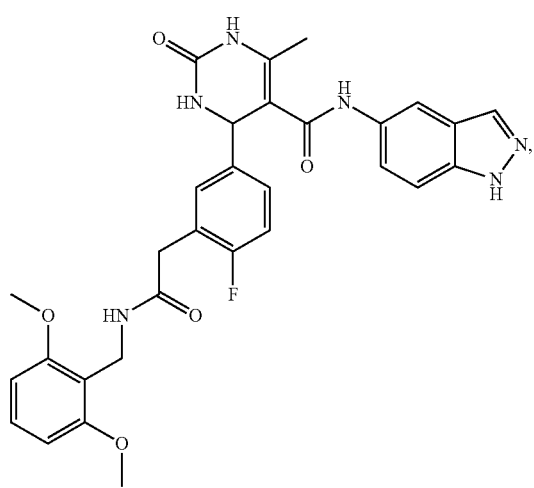
E33
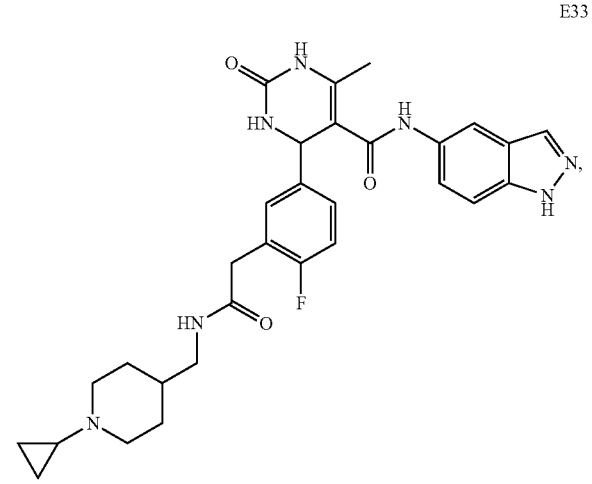

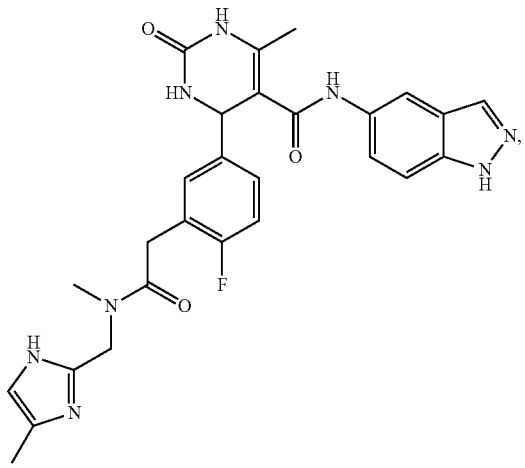

E34

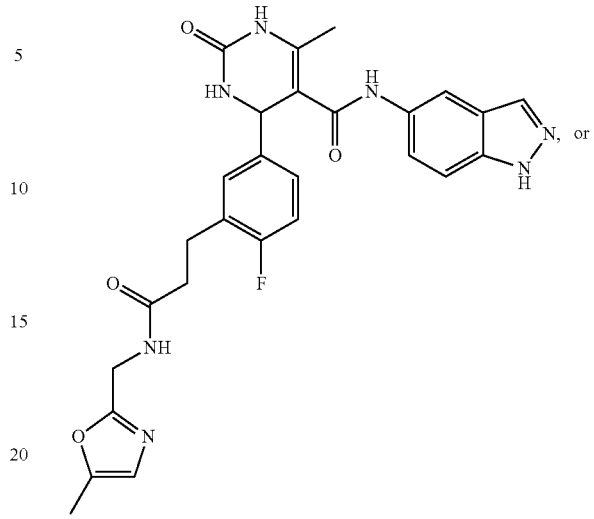

E37

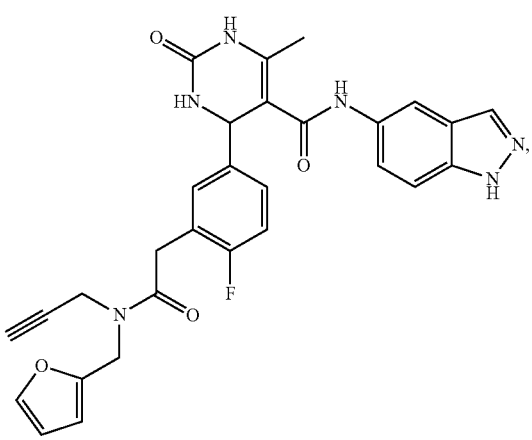

E35

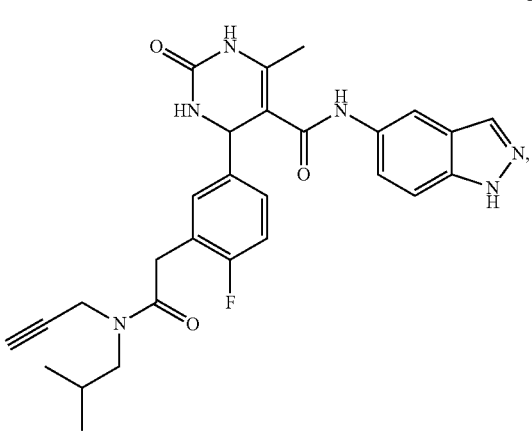

E36

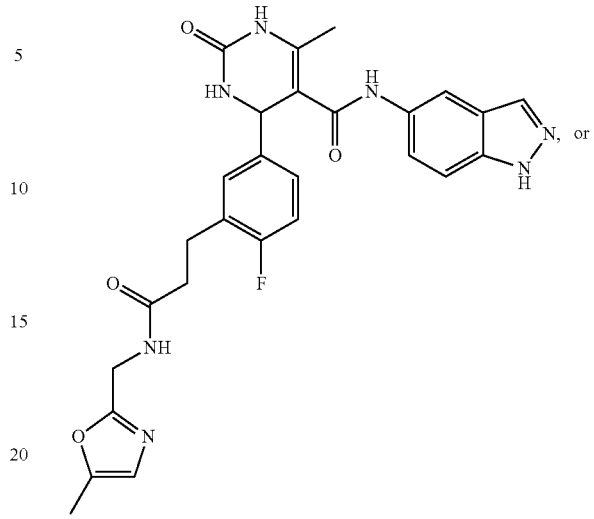

E38

Synthesis of GRK2 Inhibitors

The GRK2 inhibitors described herein are can be synthesized by any method known to one skilled in the art. For example, PCT publication nos. WO 2003/051877A1 and 2004/112719A2, each incorporated herein by reference, describe the synthesis of appropriate starting materials 2-fluoro-5-formylbenzoic acid and N-(1H-indazol-5-yl)-3-oxo-butyramide. These starting materials can be conjugated together using a Lewis acid catalyst (e.g., ytterbium), and then a substituted amide can be introduced on the resulting conjugated product using known amide bond coupling chemistry.

Additional synthetic procedures for preparing the GRK2 inhibitors disclosed herein can be found in the Examples section.

Methods

The compounds of Formula (I) can selectively inhibit GRK2. Overexpression of GRK2 has been implicated in a variety of conditions, including heart disease (see e.g., Ungerer Circuation 87:454-463 (1993); Ungerer Circ Res 74: 206-213 (1994)). As such, further provided are methods of treating or preventing heart disease using the compounds disclosed herein.

Thus, one aspect of the disclosure relates to a method of inhibiting GRK2 comprising contacting GRK2 with a compound of Formula (I) in an amount effective to inhibit GRK2. For example, GRK2 can be inhibited in a cell by contacting the cell with a compound of Formula (I). The cell can be a myocyte, such as a cardiomyocyte. The contacting of the cell can occur in vitro or in vivo. In some cases, contacting of the cell occurs in vitro. In other cases, contacting of the cell occurs in vivo. Compounds of Formula (I) can contact a cell in vivo by administering a compound of Formula (I) to a subject in need of GRK2 inhibition. Therefore, the disclosure includes administering one or more compounds of Formula (I) described herein to a subject, such as a human, in need thereof. In some embodiments, the subject suffers from heart disease (e.g., cardiac failure, cardiac hypertrophy, hypertension, or a combination thereof).

In view of the above, in various aspects, the disclosure includes a method of treating heart disease in a subject. The method comprises administering a therapeutically effective amount of a compound of Formula (I) to a subject in need of GRK2 inhibition, such that GRK2 is inhibited. Conditions resulting from overexpression of GRK2 can include those related to, for example, heart disease (e.g., cardiac failure, cardiac hypertrophy, hypertension, or a combination thereof). Use of a compound of Formula (I) to treat a condition resulting from overexpression of GRK2 in a subject, as well as use of the compound of Formula (I) described herein in the preparation of a medicament for treating the condition, also are contemplated.

Further guidance for using compounds of Formula (I) for inhibiting GRK2 can be found in the Examples section, below.

Pharmaceutical Formulations

Also provided herein are pharmaceutical formulations that include a compound of Formula (I), as previously described herein, and one or more pharmaceutically acceptable excipients.

The GRK2 inhibitors described herein can be administered to a subject in a therapeutically effective amount. The GRK2 inhibitor can be administered alone or as part of a pharmaceutically acceptable composition or formulation. In addition, the GRK2 inhibitor can be administered all at once, multiple times, or delivered substantially uniformly over a period of time. It is also noted that the dose of the compound can be varied over time.

The GRK2 inhibitors disclosed herein can be administered in combination with one or more additional pharmaceutically active compounds/agents. The additional pharmaceutically active compounds/agents may be small molecules or can be macromolecules such as a proteins, antibodies, peptibodies, DNA, RNA or fragments of such macromolecules.

The GRK2 inhibitors disclosed herein and other pharmaceutically active compounds, if desired, can be administered to a patient or subject by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The GRK2 inhibitors described herein can be administered to a patient or subject at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the patient or subject, the severity of the condition or disease being treated, and the pharmacological activity of the compound being administered. The determination of dosage ranges and optimal dosages for a particular patient or subject is within the ordinary skill in the art.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention General Synthetic Scheme 1

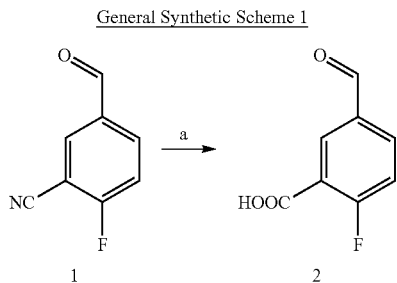

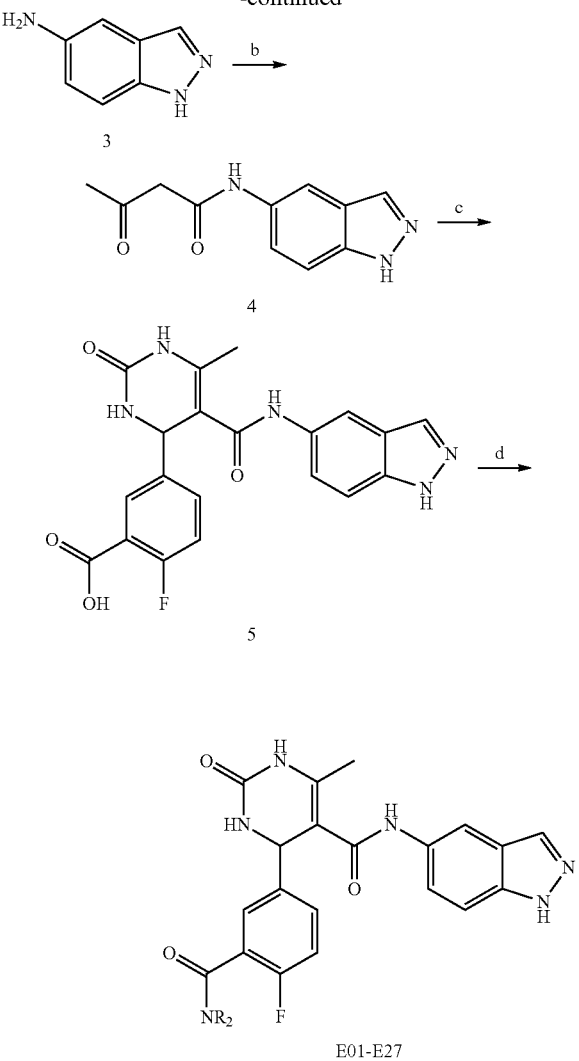

(a) see PCT Publication No. WO 2003/051877A1, incorporated herein by reference;
(b) see PCT Publication No. WO 2004/112719A2, incorporated herein by reference
(c) 2, Urea, Yb(OTf)$_3$, CH$_3$CN, 100° C., (d) HATU, DIEA, NR$_2$, DMF Preparation of 5-(5-(((1H-indazol-5-yl)carbamoyl)-6-methyl-2-oxo-1,2,3,4-tetrahydropyrimidin-4-yl)-2-fluorobenzoic acid (5)

To a 100 mL pressure vessel equipped with a stir bar was added 2-fluoro-5-formylbenzoic acid 2 (WO0351877A1, 0.682 g, 4.054 mmol), N-(1H-indazol-5-yl)-3-oxobutanamide 4 (WO2004112719A2, 0.801 g, 3.686 mmol), urea (0.332 g, 5.529 mmol), ytterbium trifluormethanesulfonate ("Yb(OTf)$_3$," 0.229 g, 0.3686 mmol) and acetonitrile ("CH$_3$CN," 15.0 mL). The reaction mixture was heated to 100° C. and stirred for 4 hours, and went from a white suspension to a clear mixture, and then back to a white suspension. After four hours, the reaction was diluted with 2 mL of water then ethyl acetate. The resulting white precipitate was filtered off and washed with ethyl acetate followed by diethyl ether yielding 5-(5-((1H-indazol-5-yl)carbamoyl)-6-methyl-2-oxo-1,2,3,4-tetrahydropyrimidin-4-yl)-2-fluorobenzoic acid (5) as a white powder (84% yield).

Example 1: 4-(4-fluoro-3-((pyridin-2-ylmethyl)carbamoyl)phenyl)-N-(1H-indazol-5-yl)-6-methyl-2-oxo-1,2,3,4-tetrahydropyrimidine-5-carboxamide (E01)

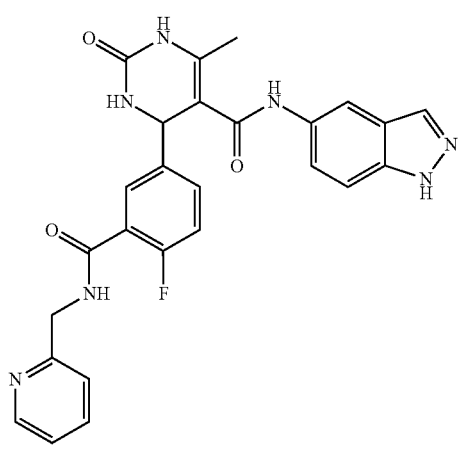

5-(5-(((1H-indazol-5-yl)carbamoyl)-6-methyl-2-oxo-1,2,3,4-tetrahydropyrimidin-4-yl)-2-fluorobenzoic acid 5 (0.300 g, 0.732 mmol), HATU (0.558 g, 1.464 mmol), DIEA (0.26 mL, 1.464 mmol), and 2-(aminomethyl)pyridine, (0.15 mL, 1.464 mmol) were added to 5 mL of DMF in a 25 mL round bottom flask and allowed to stir overnight at room temperature. The reaction was diluted with water and ethyl acetate giving a white suspension in the organic layer. The layers were separated and the organic layer was washed once with Na$_2$CO$_3$ and twice with NaCl. The organic suspension was then filtered off and washed with water giving a white solid. The solid was then washed with dichloromethane and purified using flash chromatography (20% MeOH/DCM) yielding 4-(4-fluoro-3-((pyridin-2-ylmethyl)carbamoyl)phenyl)-N-(1H-indazol-5-yl)-6-methyl-2-oxo-1,2,3,4-tetrahydropyrimidine-5-carboxamide (E01) as a white solid. (20%) $^1$H NMR (400 MHz, DMSO-d$_6$) δ 12.96 (s, 1H), 9.64 (s, 1H), 8.91 (q, J=5.3 Hz, 1H), 8.76 (d, J=2.0 Hz, 1H), 8.48 (d, J=4.3 Hz, 1H), 7.99 (s, 1H), 7.94 (s, 1H), 7.71 (td, J=7.7, 1.8 Hz, 1H), 7.66 (dd, J=6.9, 2.4 Hz, 1H), 7.62 (t, J=2.4 Hz, 1H), 7.47-7.36 (m, 3H), 7.33-7.20 (m, 3H), 5.45 (d, J=2.9 Hz, 1H), 4.53 (d, J=5.9 Hz, 2H), 2.06 (s, 3H). $^{13}$C NMR (126 MHz, DMSO) δ 164.89, 164.024, 158.56, 157.90, 152.83, 149.28, 141.14, 138.93, 137.17, 133.74, 132.47, 130.94, 128.94, 123.77, 123.65, 122.55, 121.43, 121.12, 116.71, 116.52, 110.83, 110.30, 105.49, 54.88, 45.15, 17.55. HPLC purity: 97%; MS (ESI+) m/z: 500.3 (M+1), 522.2 (M+Na+).

Example 2: 4-(3-((2,6-difluorobenzyl)carbamoyl)-4-fluorophenyl)-N-(1H-indazol-5-yl)-6-methyl-2-oxo-1,2,3,4-tetrahydropyrimidine-5-carboxamide (E02)

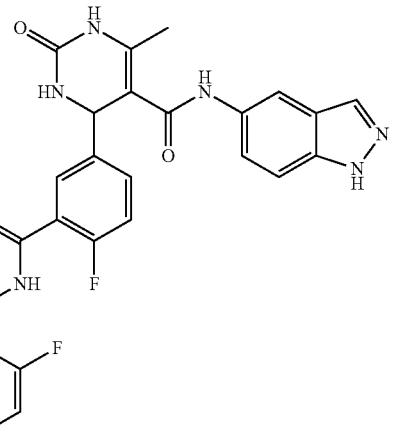

Compound E02 was prepared as described for Example 1, replacing 2-(aminomethyl)pyridine with 2,6-difluorobenzylamine. $^1$H NMR (400 MHz, DMSO) δ 12.91 (s, 1H), 9.55 (s, 1H), 8.74 (s, 1H), 8.70 (s, 1H), 7.96 (d, J=10.5 Hz, 2H), 7.59 (s, 1H), 7.52 (d, J=6.6 Hz, 1H), 7.42-7.35 (m, 4H), 7.19 (t, J=9.5 Hz, 1H), 7.05 (t, J=7.8 Hz, 2H), 5.40 (s, 1H), 4.47 (d, J=4.9 Hz, 2H), 2.05 (s, 3H). $^{13}$C NMR (126 MHz, DMSO) δ 164.90, 163.22, 152.25, 140.41, 138.43, 136.78, 133.17, 131.89, 130.11, 129.72, 128.12, 123.47, 122.50, 120.87, 115.96, 115.78, 113.79, 111.43, 111.23, 110.28, 109.72, 109.42, 104.88, 54.23, 31.19, 16.99. HPLC purity: 98%; MS (ESI+) m/z: 534.9 (M+1), 556.8 (M+Na+).

Example 3: 4-(4-fluoro-3-((2-(pyridin-2-yl)ethyl)carbamoyl)phenyl)-N-(1H-indazol-5-yl)-6-methyl-2-oxo-1,2,3,4-tetrahydropyrimidine-5-carboxamide (E03)

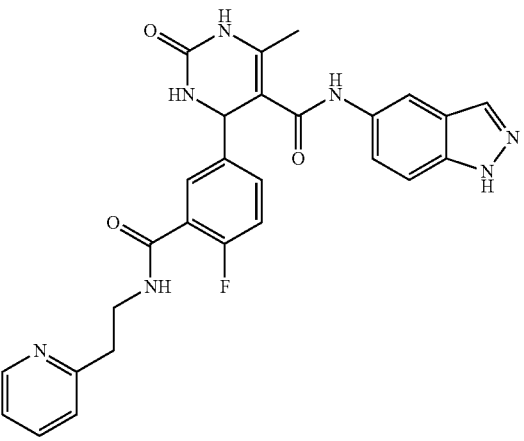 [SMILES: CC1=C(C(=O)Nc2ccc3[nH]ncc3c2)C(c2ccc(F)c(C(=O)NCCc3ccccn3)c2)NC(=O)N1]

Compound E03 was prepared as described for Example 1, replacing 2-(aminomethyl)pyridine with 2-pyridin-2-ylethylamine. $^1$H NMR (400 MHz, DMSO) δ ppm $^1$H NMR (400 MHz, DMSO) δ 12.92 (s, 1H), 9.58 (s, 1H), 8.77 (s, 1H), 8.47 (d, J=4.0 Hz, 1H), 8.37 (dd, J=8.2, 5.1 Hz, 1H), 7.97 (d, J=13.9 Hz, 2H), 7.67 (td, J=7.6, 1.8 Hz, 1H), 7.62 (s, 1H), 7.57 (dd, J=6.9, 2.3 Hz, 1H), 7.43-7.34 (m, 3H), 7.26-7.15 (m 3H), 5.42 (d, J=2.1 Hz, 1H), 3.57 (dd, J=13.2, 6.9 Hz, 2H), 2.94 (t, J=7.2 Hz, 2H), 2.05 (s, 3H). $^{13}$C NMR (126 MHz, DMSO) δ 164.91, 163.16, 159.33, 158.86, 156.86, 152.26, 148.93, 140.49, 138.32, 136.75, 136.34, 133.18, 131.90, 130.03, 128.17, 123.05, 122.50, 121.40, 120.84, 116.02, 110.238, 109.74, 104.93, 54.31, 36.90, 16.99. HPLC purity: 95%; MS (ESI+) m/z: 514.0 (M+1), 536.0 (M+Na+).

Example 4: 4-(4-fluoro-3-((3-fluorobenzyl)carbamoyl)phenyl)-N-(1H-indazol-5-yl)-6-methyl-2-oxo-1,2,3,4-tetrahydropyrimidine-5-carboxamide (E04)

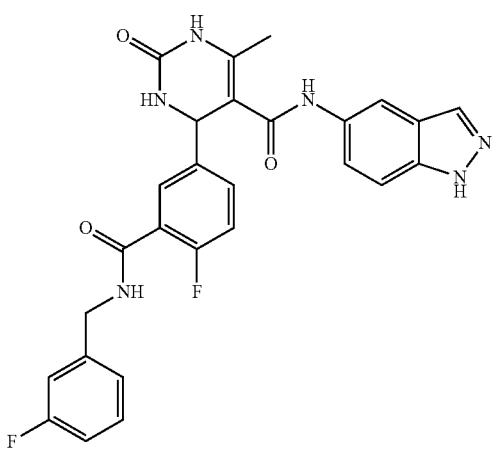 [SMILES: CC1=C(C(=O)Nc2ccc3[nH]ncc3c2)C(c2ccc(F)c(C(=O)NCc3cccc(F)c3)c2)NC(=O)N1]

Compound E04 was prepared as described for Example 1, replacing 2-(aminomethyl)pyridine with 3-fluorobenzylamine. $^1$H NMR (500 MHz, DMSO) δ 12.90 (s, 1H), 9.58 (s, 1H), 8.88 (s, 1H), 8.76 (s, 1H), 7.97 (d, J=18.0 Hz, 2H), 7.63 (s, 2H), 7.46-7.31 (m, 4H), 7.27 (t, J=9.4 Hz, 1H), 7.12 (dd, J=15.2, 9.0 Hz, 2H), 7.08-7.02 (m, J=11.8, 5.3 Hz, 1H), 5.44 (s, 1H), 4.46 (d, J=5.8 Hz, 2H), 2.07 (s, 3H). $^{13}$C NMR (126 MHz, DMSO) δ 171.71, 165.49, 164.12, 163.62, 161.69, 159.73, 157.75, 152.83, 142.48, 141.11, 139.00, 132.47, 130.85, 130.67, 128.82, 124.02, 123.50, 123.06, 121.44, 116.57, 114.18, 113.97, 110.85, 110.36, 105.45, 54.85, 42.65, 17.56. HPLC purity: 99%; MS (ESI+) m/z: 516.9 (M+1), 538.8 (M+Na+).

Example 5: 4-(4-fluoro-3-((2-methoxybenzyl)carbamoyl)phenyl)-N-(1H-indazol-5-yl)-6-methyl-2-oxo-1,2,3,4-tetrahydropyrimidine-5-carboxamide (E05)

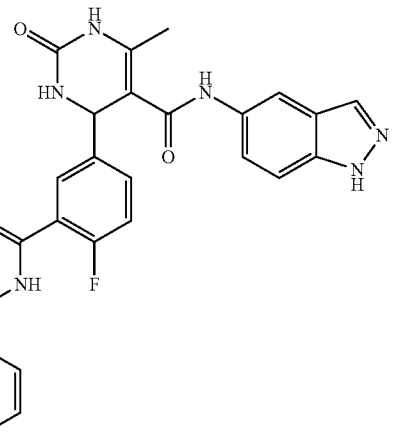

Compound E05 was prepared as described for Example 1, replacing 2-(aminomethyl)pyridine with 2-methoxybenzylamine. $^1$H NMR (400 MHz, DMSO) δ 12.94 (s, 1H), 9.60 (s, 1H), 8.78 (s, 1H), 8.64 (s, 1H), 8.01 (s, 1H), 7.97 (s, 1H), 7.67-7.61 (m, 2H), 7.45-7.36 (m, 3H), 7.31-7.17 (m, 3H), 6.98 (d, J=8.0 Hz, 1H), 6.88 (t, J=7.4 Hz, 1H), 5.45 (s, 1H), 4.42 (d, J=6.0 Hz, 2H), 3.81 (s, 3H), 2.08 (s, 3H). $^{13}$C NMR (126 MHz, DMSO) δ 164.92, 163.45, 163.44, 157.21, 156.46, 152.27, 140.52, 138.43, 136.78, 133.18, 131.91, 130.14, 128.26, 127.88, 127.05, 126.29, 123.63, 122.51, 120.86, 119.99, 115.96, 110.34, 109.57, 104.91, 55.20, 54.28, 37.75, 16.99. HPLC purity: 95%; MS (ESI+) m/z: 528.8 (M+1), 550.8 (M+Na+).

Example 6: 4-(4-fluoro-3-((4-methoxybenzyl)carbamoyl)phenyl)-N-(1H-indazol-5-yl)-6-methyl-2-oxo-1,2,3,4-tetrahydropyrimidine-5-carboxamide (E06)

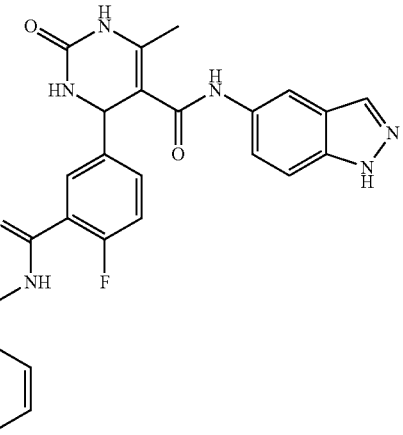

Compound E06 was prepared as described for Example 1, replacing 2-(aminomethyl)pyridine with 4-methoxybenzylamine. ¹H NMR (400 MHz, DMSO) δ 12.94 (s, 1H), 9.60 (s, 1H), 8.77 (s, 2H), 7.98 (d, J=14.1 Hz, 2H), 7.63 (s, 1H), 7.60 (dd, J=6.9, 2.3 Hz, 1H), 7.44-7.35 (m, 3H), 7.27 (d, J=10.2 Hz, 1H), 7.22 (d, J=8.5 Hz, 2H), 6.86 (d, J=8.7 Hz, 2H), 5.44 (s, 1H), 4.37 (d, J=6.0 Hz, 2H), 3.71 (s, 3H), 2.07 (s, 3H). ¹³C NMR (101 MHz, DMSO) δ 165.47, 163.86, 158.60, 157.43, 152.83, 138.93, 137.32, 133.74, 132.46, 131.57, 128.91, 128.73, 125.28, 124.22, 123.06, 121.40, 116.62, 116.39, 114.09, 110.80, 110.29, 105.47, 55.47, 54.81, 42.53, 17.55. HPLC purity: 99%; MS (ESI−) m/z: 527.0 (M−1).

Example 7: 4-(4-fluoro-3-((2-(pyridin-4-yl)ethyl)carbamoyl)phenyl)-N-(1H-indazol-5-yl)-6-methyl-2-oxo-1,2,3,4-tetrahydropyrimidine-5-carboxamide (E07)

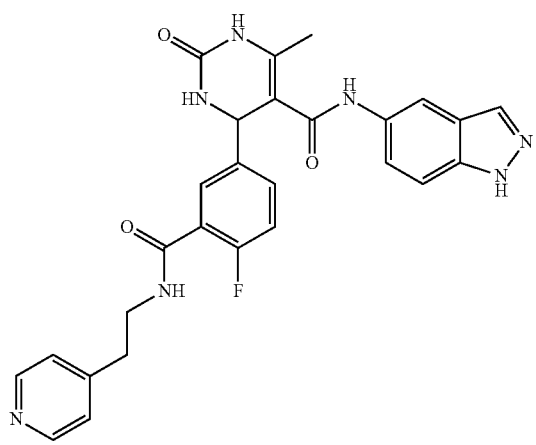 [SMILES: CC1=C(C(=O)Nc2ccc3[nH]ncc3c2)C(c2ccc(F)c(C(=O)NCCc3ccncc3)c2)NC(=O)N1]

Compound E07 was prepared as described for Example 1, replacing 2-(aminomethyl)pyridine with 2-(4-pyridyl)ethyl amine. ¹H NMR (400 MHz, DMSO) δ 12.94 (s, 1H), 9.59 (s, 1H), 8.78 (s, 1H), 8.45 (d, J=5.5 Hz, 2H), 8.38 (s, 1H), 7.99 (d, J=13.9 Hz, 2H), 7.63 (s, 1H), 7.55 (d, J=4.7 Hz, 1H), 7.47-7.34 (m, 3H), 7.29-7.18 (m, J=7.5 Hz, 3H), 5.44 (s, 1H), 3.50 (dd, J=12.8, 6.6 Hz, 2H), 2.82 (t, J=7.0 Hz, 2H), 2.07 (s, 3H). ¹³C NMR (126 MHz, DMSO) δ 165.48, 163.94, 152.83, 149.87, 148.68, 141.05, 138.95, 137.34, 133.75, 132.47, 130.63, 128.61, 124.50, 123.07, 121.42, 116.56, 116.37, 114.22, 110.82, 110.30, 105.48, 54.86, 39.47, 34.50, 17.55. HPLC purity: 99%; MS (ESI+) m/z: 514.1 (M+1), 536.1 (M+Na+).

Example 8: 4-(4-fluoro-3-((isoquinolin-1-ylmethyl)carbamoyl)phenyl)-N-(1H-indazol-5-yl)-6-methyl-2-oxo-1,2,3,4-tetrahydropyrimidine-5-carboxamide (E08)

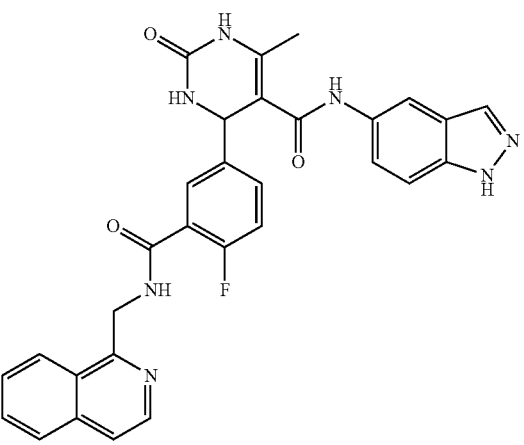 [SMILES: CC1=C(C(=O)Nc2ccc3[nH]ncc3c2)C(c2ccc(F)c(C(=O)NCc3nccc4ccccc34)c2)NC(=O)N1]

Compound E08 was prepared as described for Example 1, replacing 2-(aminomethyl)pyridine with isoquinolin1-ylm-ethylamine. ¹H NMR (400 MHz, DMSO) δ ppm 12.95, 9.61, 8.90, 8.80, 8.43, 8.31, 8.01-7.97, 7.82-7.67, 7.48-7.36, 7.30, 5.47, 5.15, 2.08.

Example 9: 4-(3-((2,6-dichlorobenzyl)carbamoyl)-4-fluorophenyl)-N-(1H-indazol-5-yl)-6-methyl-2-oxo-1,2,3,4-tetrahydropyrimidine-5-carboxamide (E09)

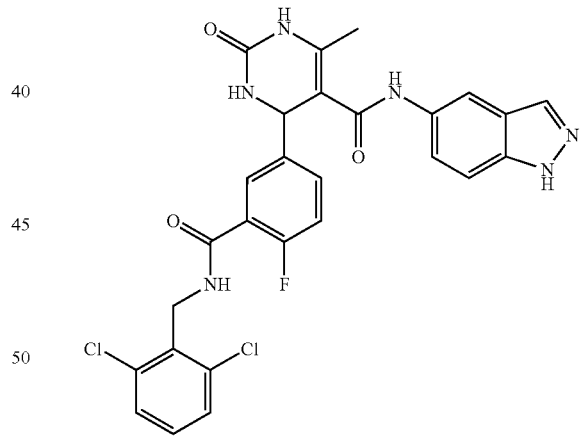

Compound E09 was prepared as described for Example 1, replacing 2-(aminomethyl)pyridine with isoquinolin1-ylm-ethylamine. ¹H NMR (500 MHz, DMSO) δ 12.91 (s, 1H), 9.56 (s, 1H), 8.74 (d, J=2.0 Hz, 1H), 8.55 (t, J=5.3 Hz, 1H), 7.98 (s, 1H), 7.95 (s, 1H), 7.61-7.59 (m, 1H), 7.52 (dd, J=6.7, 2.4 Hz, 1H), 7.45 (s, 1H), 7.43 (s, 1H), 7.41-7.35 (m, 3H), 7.33 (dd, J=8.5, 7.6 Hz, 1H), 7.18 (dd, J=10.0, 8.7 Hz, 1H), 5.41 (d, J=2.2 Hz, 1H), 4.70-4.61 (m, 2H), 2.05 (s, 3H). ¹³C NMR (126 MHz, DMSO) δ 164.90, 163.37, 152.28, 140.30, 138.50, 136.78, 135.55, 133.18, 132.88, 131.91, 130.07, 128.38, 128.02, 123.83, 123.71, 122.51, 120.88, 115.92, 115.73, 110.28, 109.71, 104.88, 54.20, 38.91, 16.99. HPLC purity: 97%;

Example 10: 4-(3-((2,6-dimethylbenzyl)carbamoyl)-4-fluorophenyl)-N-(1H-indazol-5-yl)-6-methyl-2-oxo-1,2,3,4-tetrahydropyrimidine-5 carboxamide (E10)

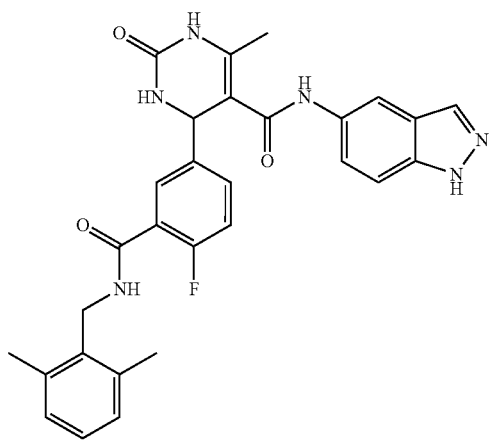 [SMILES: CC1=C(C(=O)Nc2ccc3[nH]ncc3c2)C(c2ccc(F)c(C(=O)NCc3c(C)cccc3C)c2)NC(=O)N1]

Compound E10 was prepared as described for Example 1, replacing 2-(aminomethyl)pyridine with 2,6-dimethylbenzylamine. $^1$H NMR (500 MHz, DMSO) δ 12.93 (s, 1H), 9.58 (s, 1H), 8.76 (d, J=1.6 Hz, 1H), 8.41 (t, J=4.6 Hz, 1H), 7.99 (d, J=18.7 Hz, 2H), 7.51 (dd, J=6.7, 2.3 Hz, 1H), 7.43-7.34 (m, 3H), 7.19 (dd, J=9.9, 8.7 Hz, 1H), 7.10-7.03 (m, 1H), 6.99 (d, J=7.5 Hz, 2H), 5.43 (d, J=2.4 Hz, 1H), 4.43 (t, J=4.7 Hz, 2H), 2.32 (s, 6H), 2.07 (s, 3H). HPLC purity: 96%; MS (ESI+) m/z: 527.1 (M+1).

Example 11: 4-(3-((2,6-dimethoxybenzyl)carbamoyl)-4-fluorophenyl)-N-(1H-indazol-5-yl)-6-methyl-2-oxo-1,2,3,4-tetrahydropyrimidine-5-carboxamide (E11)

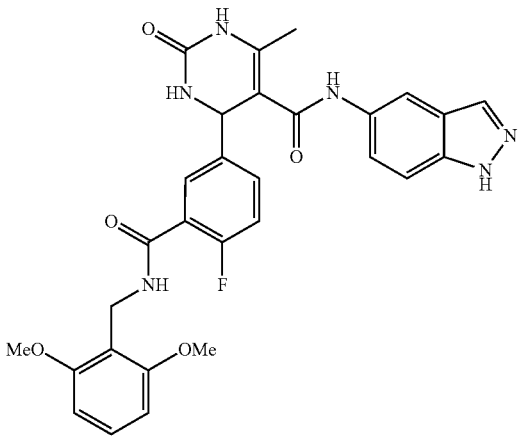 [SMILES: COc1cccc(OC)c1CNC(=O)c1cc(C2NC(=O)NC(C)=C2C(=O)Nc2ccc3[nH]ncc3c2)ccc1F]

Compound E11 was prepared as described for Example 1, replacing 2-(aminomethyl)pyridine with 2,6-dimethoxybenzylamine. $^1$H NMR (400 MHz, DMSO-d$_6$) δ 12.94 (s, 1H), 9.58 (s, 1H), 8.77 (d, J=1.9 Hz, 1H), 8.03-7.93 (m, 3H), 7.62 (dt, J=5.0, 2.4 Hz, 2H), 7.45-7.32 (m, 3H), 7.29-7.14 (m, 2H), 6.65 (d, J=8.4 Hz, 2H), 5.43 (d, J=2.9 Hz, 1H), 4.48 (d, J=4.9 Hz, 2H), 3.77 (s, 6H), 2.07 (s, 3H). $^{13}$C NMR (126 MHz, DMSO) δ 164.89, 158.21, 152.26, 140.43, 138.40, 136.76, 133.68, 133.17, 131.91, 128.98, 128.59, 123.41, 123.30, 122.50, 120.85, 115.93, 115.74, 112.95, 110.24, 109.71, 104.95, 103.99, 55.68, 54.28, 32.25, 16.98. HPLC purity: 97%; MS (ESI+) m/z: 559.1 (M+1), 581.1 (M+Na+).

Example 12: 4-(4-fluoro-3-(methylcarbamoyl)phenyl)-N-(1H-indazol-5-yl)-6-methyl-2-oxo-1,2,3,4-tetrahydropyrimidine-5-carboxamide (E12)

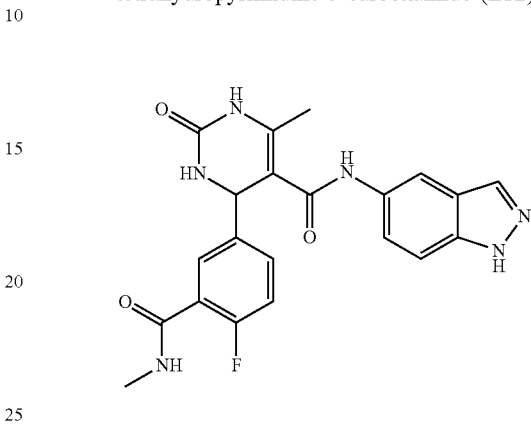

Compound E12 was prepared as described for Example 1, replacing 2-(aminomethyl)pyridine with methylamine. $^1$H NMR (500 MHz, DMSO) δ 12.93 (s, 1H), 9.58 (s, 1H), 8.75 (d, J=1.9 Hz, 1H), 8.20 (t, J=1.3 Hz, 1H), 7.98 (d, J=7.1 Hz, 2H), 7.63-7.57 (m, 2H), 7.44-7.35 (m, 3H), 7.24 (dd, J=10.3, 8.6 Hz, 1H), 5.43 (d, J=2.9 Hz, 1H), 3.17 (d, J=4.6 Hz, 1H), 2.75 (d, J=4.6 Hz, 3H), 2.07 (s, 3H). $^{13}$C NMR (126 MHz, DMSO) δ 164.92, 163.71, 152.24, 140.48, 138.29, 136.77, 133.18, 131.90, 130.01, 128.19, 123.70, 122.50, 120.85, 115.97, 115.79, 110.25, 109.72, 104.96, 54.32, 26.17, 16.98. HPLC purity: 96%; MS (ESI+) m/z: 445.1 (M+1).

Example 13: 4-(3-((3,5-bis(trifluoromethyl)benzyl)carbamoyl)-4-fluorophenyl)-N-(1H-indazol-5-yl)-6-methyl-2-oxo-1,2,3,4-tetrahydropyrimidine-5-carboxamide (E13)

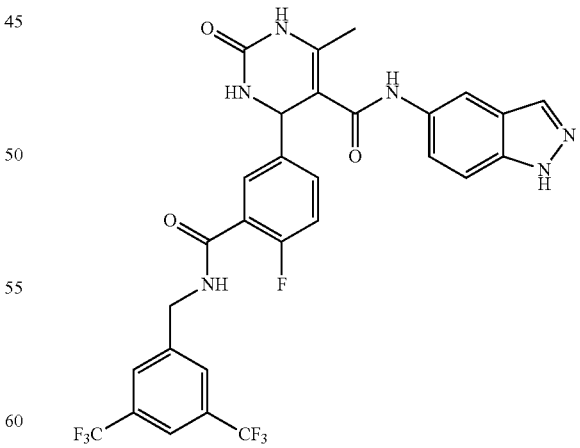

Compound E13 was prepared as described for Example 1, replacing 2-(aminomethyl)pyridine with 3,5-bis(trifluoromethyl)benzylamine. $^1$H NMR (400 MHz, DMSO) δ 12.93 (s, 1H), 9.58 (s, 1H), 9.05 (s, 1H), 8.77 (s, 1H), 8.03 (s, 2H), 8.00 (d, J=4.3 Hz, 2H), 7.95 (s, 1H), 7.65-7.59 (m, 2H), 7.46-7.28 (m, 4H), 5.44 (s, 1H), 4.64 (d, J=5.9 Hz, 2H), 2.07 (s, 3H). HPLC purity: 95%; MS (ESI+) m/z: 635.0 (M+1), 657.0 (M+Na+).

Example 14: 4-(3-((2,6-dimethylphenethyl)carbamoyl)-4-fluorophenyl)-N-(1H-indazol-5-yl)-6-methyl-2-oxo-1,2,3,4-tetrahydropyrimidine-5-carboxamide (E14)

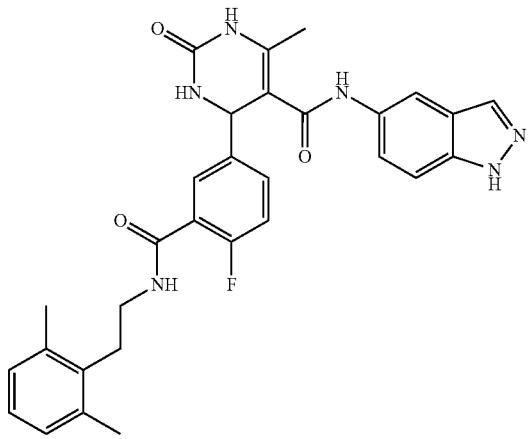 [SMILES: CC1=C(C(=O)Nc2ccc3[nH]ncc3c2)C(c2ccc(F)c(C(=O)NCCc3c(C)cccc3C)c2)NC(=O)N1]

Compound E14 was prepared as described for Example 1, replacing 2-(aminomethyl)pyridine with 2-(2,6-dimethylphenyl)ethanamine. $^1$H NMR (500 MHz, DMSO) δ 12.93 (s, 1H), 9.59 (s, 1H), 8.77 (s, 1H), 8.50 (dd, J=8.4, 5.6 Hz, 1H), 7.98 (d, J=19.6 Hz, 2H), 7.66 (dd, J=7.0, 2.3 Hz, 1H), 7.63 (broad s, 1H), 7.45-7.36 (m, 3H), 7.26 (dd, J=10.3, 8.6 Hz, 1H), 6.98 (d, J=1.1 Hz, 3H) 5.45 (d, J=1.8 Hz, 1H), 3.32-3.23 (m, 2H), 2.82 (dd, J=10.0, 6.5 Hz, 2H), 2.33 (s, 6H), 2.08 (s, 3H). $^{13}$C NMR (126 MHz, DMSO) δ 165.49, 163.73, 157.76, 152.81, 141.14, 138.84, 137.35, 136.67, 136.04, 133.73, 132.45, 130.78, 128.91, 128.33, 126.37, 124.01, 123.07, 121.45, 116.50, 110.88, 110.28, 105.53, 54.94, 38.91, 30.03, 19.84, 17.54. HPLC purity: 97%; MS (ESI+) m/z: 541.1 (M+1), 563.1 (M+Na+).

Example 15: 4-(4-fluoro-3-(((3-methylpyridin-2-yl)methyl)carbamoyl)phenyl)-N-(1H-indazol-5-yl)-6-methyl-2-oxo-1,2,3,4-tetrahydropyrimidine-5-carboxamide (E15)

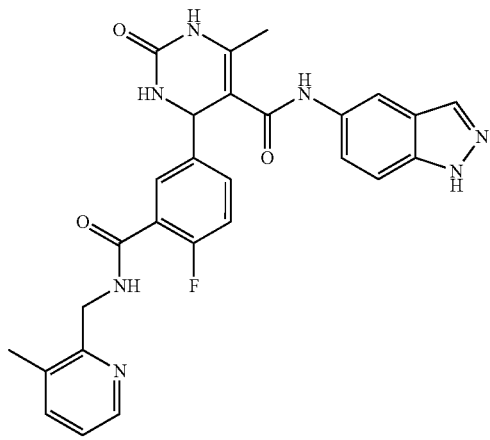 [SMILES: CC1=C(C(=O)Nc2ccc3[nH]ncc3c2)C(c2ccc(F)c(C(=O)NCc3ncccc3C)c2)NC(=O)N1]

Compound E15 was prepared as described for Example 1, replacing 2-(aminomethyl)pyridine with (3-methylpyridin-2-yl)methanamine. $^1$H NMR (400 MHz, DMSO-d$_6$) δ 12.93 (s, 1H), 9.60 (s, 1H), 8.87 (broad s, 1H), 8.77 (s, 1H), 8.35-8.29 (m, 2H), 7.99 (d, J=16 Hz, 2H), 7.65-7.61 (m, 2H), 7.47-7.36 (m, 3H), 7.30 (dd, J=10.3, 8.5 Hz, 1H), 7.17 (d, J=5.0 Hz, 1H), 5.46 (s, 1H), 4.43 (d, J=5.9 Hz, 2H), 2.28 (s, 3H), 2.08 (s, 3H). $^{13}$C NMR (126 MHz, DMSO) δ 165.48, 164.28, 157.75, 155.04, 152.83, 150.47, 147.76, 146.21, 139.12, 137.25, 133.59, 132.48, 131.28, 130.82, 128.71, 123.94, 123.07, 121.40, 116.63, 116.41, 110.74, 110.19, 105.43, 98.78, 54.74, 40.56, 17.45, 15.74. HPLC purity: 97%; MS (ESI+) m/z: 514.1 (M+1), 536.1 (M+Na+).

Example 16: 4-(3-(benzylcarbamoyl)-4-fluorophenyl)-N-(1H-indazol-5-yl)-6-methyl-2-oxo-1,2,3,4-tetrahydropyrimidine-5-carboxamide (E16)

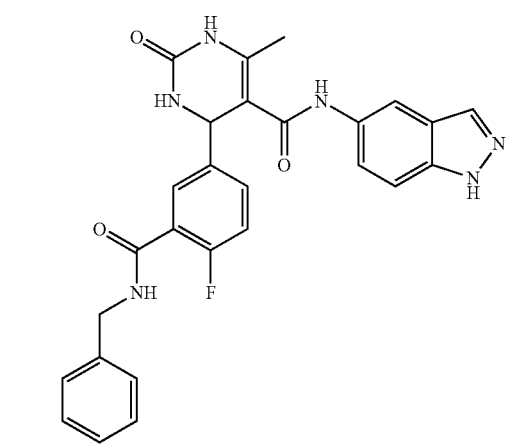 [SMILES: CC1=C(C(=O)Nc2ccc3[nH]ncc3c2)C(c2ccc(F)c(C(=O)NCc3ccccc3)c2)NC(=O)N1]

Compound E16 was prepared as described for Example 1, replacing 2-(aminomethyl)pyridine with benzylamine. $^1$H NMR (500 MHz, DMSO) δ 12.93 (s, 1H), 9.59 (s, 1H), 8.83 (td, J=5.4, 1.5 Hz, 1H), 8.77 (d, J=1.4 Hz, 1H), 7.98 (d, J=18.6 Hz, 2H), 7.65-7.60 (m, 2H), 7.44-7.37 (m, 3H), 7.32-7.20 (m, 6H), 5.45 (d, J=2.9 Hz, 1H), 4.45 (d, J=6.1 Hz, 2H), 2.08 (s, 3H). $^{13}$C NMR (126 MHz, DMSO) δ 164.92, 163.46, 159.13, 157.15, 152.26, 140.51, 139.09, 138.40, 136.78, 133.18, 131.91, 130.12, 128.14, 126.95, 126.62, 123.71, 123.59, 122.51, 120.85, 116.06, 115.87, 110.26, 109.72, 104.91, 54.28, 42.52, 16.99. HPLC purity: 95%; MS (ESI+) m/z: 499.1 (M+1).

Example 17: 4-(3-((2,6-bis(trifluoromethyl)benzyl)carbamoyl)-4-fluorophenyl)-N-(1H-indazol-5-yl)-6-methyl-2-oxo-1,2,3,4-tetrahydropyrimidine-5-carboxamide (E17)

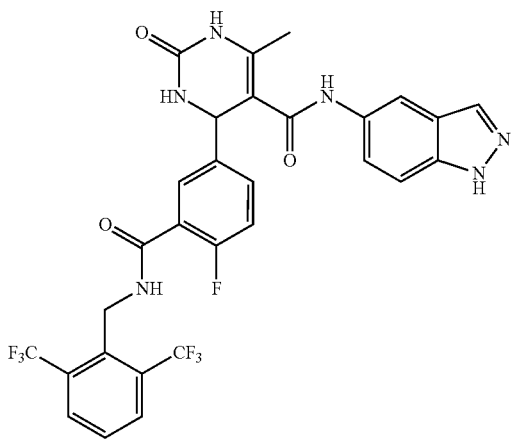 [SMILES: CC1=C(C(=O)Nc2ccc3[nH]ncc3c2)C(c2ccc(F)c(C(=O)NCc3c(C(F)(F)F)cccc3C(F)(F)F)c2)NC(=O)N1]

Compound E17 was prepared as described for Example 1, replacing 2-(aminomethyl)pyridine with 2,6-bis(trifluoromethyl)benzylamine. $^1$H NMR (400 MHz, DMSO-$d_6$) δ 12.93 (s, 1H), 9.57 (s, 1H), 8.76 (s, 1H), 8.61 (s, 1H), 8.10 (d, J=8.0 Hz, 2H), 7.97 (d, J=10.9 Hz, 2H), 7.80 (t, J=8.0 Hz, 1H), 7.62 (s, 1H), 7.51 (dd, J=6.7, 2.4 Hz, 1H), 7.45-7.34 (m, 3H), 7.19 (dd, J=9.9, 8.6 Hz, 1H), 5.43 (d, J=2.9 Hz, 1H), 4.73-4.59 (m, 2H), 2.07 (s, 3H). $^{13}$C NMR (126 MHz, DMSO) δ 165.44, 163.55, 159.45, 157.54, 152.90, 140.89, 139.16, 137.34, 133.98, 133.69, 132.44, 130.09, 128.33, 125.24, 125.14, 123.05, 121.41, 116.50, 116.24, 110.96, 110.31, 105.40, 54.65, 37.73, 17.54. HPLC purity: 95%; MS (ESI+) m/z: 635.0 (M+1), 657.0 (M+Na+).

Example 18: 4-(4-fluoro-3-((3-methoxybenzyl)carbamoyl)phenyl)-N-(1H-indazol-5-yl)-6-methyl-2-oxo-1,2,3,4-tetrahydropyrimidine-5-carboxamide (E18)

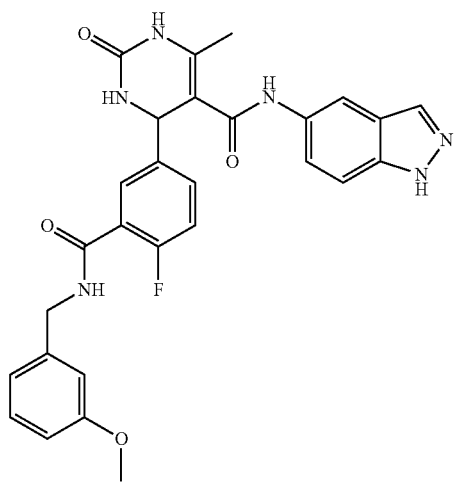 [SMILES: COc1cccc(CNC(=O)c2cc(C3NC(=O)NC(C)=C3C(=O)Nc3ccc4[nH]ncc4c3)ccc2F)c1]

Compound E18 was prepared as described for Example 1, replacing 2-(aminomethyl)pyridine with (3-methoxyphenyl) methanamine. $^1$H NMR (400 MHz, DMSO-$d_6$) δ 12.93 (s, 1H), 9.58 (s, 1H), 8.82 (broad s, 1H), 8.76 (s, 1H), 7.98 (d, J=16 Hz, 2H), 7.65-7.57 (m, 2H), 7.46-7.34 (m, 3H), 7.32-7.17 (m, 2H), 6.91-6.84 (m, 2H), 6.80 (dt, J=8.2, 1.4 Hz, 1H), 5.45 (d, J=2.8 Hz, 1H), 4.43 (d, J=6.1 Hz, 2H), 3.72 (s, 3H), 2.07 (s, 3H). HPLC purity: 95%; MS (ESI+) m/z: 529.1 (M+1), 551.1 (M+Na+).

Example 19: 4-(3-(sec-butyl(methyl)carbamoyl)-4-fluorophenyl)-N-(1H-indazol-5-yl)-6-methyl-2-oxo-1,2,3,4-tetrahydropyrimidine-5-carboxamide (E19)

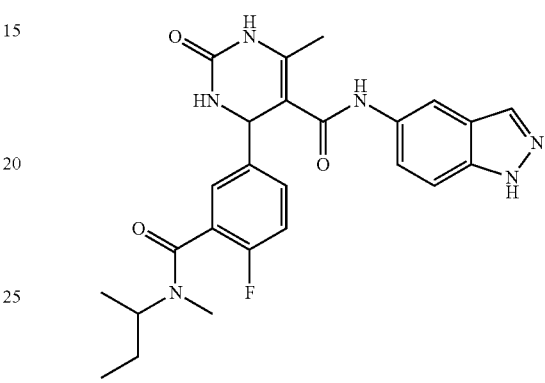

Compound E19 was prepared as described for Example 1, replacing 2-(aminomethyl)pyridine with N-methylbutan-2-amine. $^1$H NMR (400 MHz, cd$_3$od, 55° C.) δ 7.94 (s, 1H), 7.88-7.80 (m, 1H), 7.55-7.45 (m, 1H), 7.44 (d, J=9.0 Hz, 1H), 7.35-7.23 (m, 2H), 7.21-7.15 (m, 1H), 5.52 (d, J=13.1 Hz, 1H), 4.59 (dq, J=13.2, 6.7 Hz, 0.5H), 3.40 (s, 0.5H), 2.87 (d, J=2.6 Hz, 2H), 2.56 (s, 1H), 2.12 (d, J=3.3 Hz, 3H), 1.53-1.48 (m, 1H), 1.17-1.05 (m, 3H), 0.87 (dt, J=20.4, 7.4 Hz, 2H), 0.70-0.57 (m, 2H). HPLC purity: 95%; MS (ESI+) m/z: 479.2 (M+1), 501.1 (M+Na+).

Example 20: 4-(3-((2-(azepan-1-yl)propyl)carbamoyl)-4-fluorophenyl)-N-(1H-indazol-5-yl)-6-methyl-2-oxo-1,2,3,4-tetrahydropyrimidine-5-carboxamide (E20)

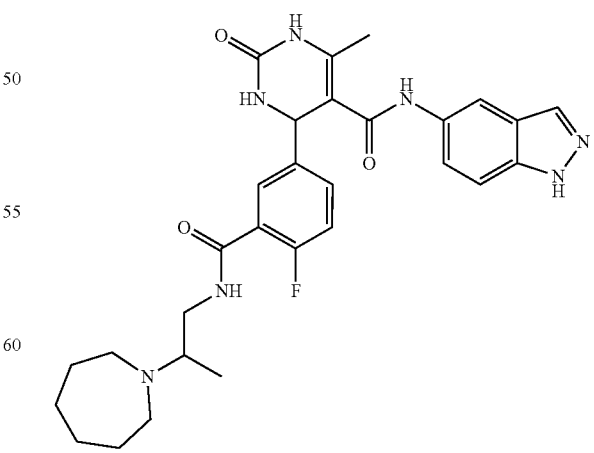

Compound E20 was prepared as described for Example 1, replacing 2-(aminomethyl)pyridine with 2-(azepan-1-yl)

propan-1-amine. ¹H NMR (400 MHz, Methanol-d₄) δ 7.96 (s, 1H), 7.90 (dd, J=7.1, 2.4 Hz, 2H), 7.87 (s, 1H), 7.54 (ddd, J=8.6, 4.8, 2.5 Hz, 1H), 7.44 (d, J=8.9 Hz, 1H), 7.32 (dd, J=8.9, 1.9 Hz, 1H), 7.21 (dd, J=11.1, 8.5 Hz, 1H), 5.54 (s, 1H), 3.40 (dt, J=13.5, 5.3 Hz 1H), 3.23 (ddd, J=13.4, 8.9, 4.3 Hz, 1H), 2.93 (p, J=6.3 Hz, 1H), 2.75 (d, J=12.9 Hz, 2H), 2.58 (d, J=12.6 Hz, 2H), 2.14 (d, J=1.1 Hz, 3H), 1.70-1.52 (m, 8H), 1.00 (d, J=6.6 Hz, 3H). ¹³C NMR (126 MHz, cd₃od) δ 168.15, 162.23, 155.08, 142.20, 141.59, 138.23, 132.96, 132.88, 132.67, 130.53, 123.49, 117.75, 117.55, 113.45, 111.63, 111.27, 107.64, 102.14, 73.58, 62.31, 60.46, 57.38, 52.00, 44.02, 30.53, 27.91, 17.21, 12.21. HPLC purity: 96%; MS (ESI+) m/z: 548.2 (M+1).

Example 21: 4-(4-fluoro-3-(methyl((tetrahydro-2H-pyran-2-yl)methyl)carbamoyl)phenyl)-N-(1H-indazol-5-yl)-6-methyl-2-oxo-1,2,3,4-tetrahydropyrimidine-5-carboxamide (E21)

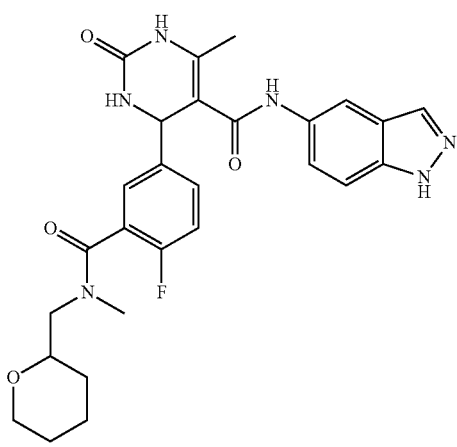 [SMILES: CC1=C(C(=O)Nc2ccc3[nH]ncc3c2)C(c2ccc(F)c(C(=O)N(C)CC3CCCCO3)c2)NC(=O)N1]

Compound E21 was prepared as described for Example 1, replacing 2-(aminomethyl)pyridine with N-methyl-1-(tetrahydro-2H-pyran-2-yl)methanamine. ¹H NMR (400 MHz, cd₃od) δ 7.99-7.88 (m, 2H), 7.50 (ddd, J=11.8, 5.7, 3.2 Hz, 1H), 7.45 (d, J=9.1 Hz, 1H), 7.39-7.30 (m, 2H), 7.23-7.14 (m, 1H), 5.56-5.51 (m, 1H), 3.92-3.76 (m, 1H), 3.64-3.55 (m, 1H), 3.44-3.33 (m, 1H), 3.26-3.06 (m, 3H), 2.83 (d, J=4.6 Hz, 2H), 2.12 (d, J=5.9 Hz, 3H), 1.82 (s, 1H), 1.63-1.43 (m, 3H), 1.37-1.10 (m, 2H). HPLC purity: 96%; MS (ESI+) m/z: 521.1 (M+1), 543.1 (M+Na+).

Example 22: 4-(3-(((5-ethyl-1,2,4-oxadiazol-3-yl)methyl)carbamoyl)-4-fluorophenyl)-N-(1H-indazol-5-yl)-6-methyl-2-oxo-1,2,3,4-tetrahydropyrimidine-5-carboxamide (E22)

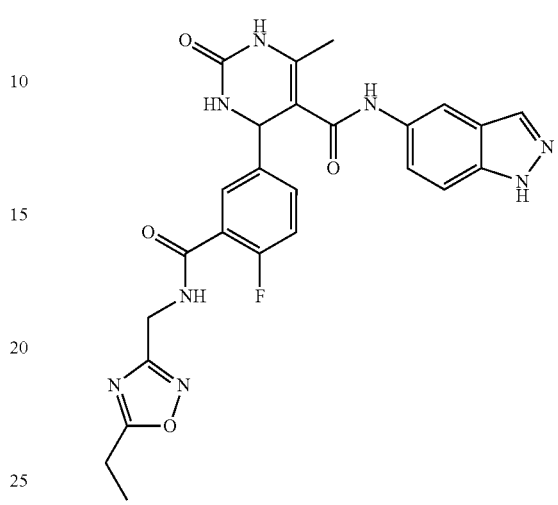

Compound E22 was prepared as described for Example 1, replacing -(aminomethyl)pyridine with (5-ethyl-1,2,4-oxadiazol-3-yl)methanamine. ¹H NMR (400 MHz, DMSO-d₆) δ 12.92 (s, 1H), 9.58 (s, 1H), 8.86 (td, J=5.9, 3.2 Hz, 1H), 8.77 (d, J=2.0 Hz, 1H), 7.99 (d, J=8.0 Hz, 2H), 7.67-7.62 (m, 2H), 7.45-7.33 (m, 3H), 7.26 (dd, J=10.4, 8.5 Hz, 1H), 5.43 (d, J=3.0 Hz, 1H), 4.51 (d, J=5.8 Hz, 2H), 2.89 (q, J=7.6 Hz, 2H), 2.05 (s, 3H), 1.23 (t, J=7.6 Hz, 3H). ¹³C NMR (101 MHz, DMSO) δ 181.32, 168.27, 165.46, 164.06, 160.08, 157.61, 152.82, 141.16, 138.88, 137.33, 132.43, 128.96, 123.28, 123.13, 123.05, 121.44, 110.80, 110.29, 109.98, 105.47, 54.91, 35.67, 19.89, 17.59, 10.86. HPLC purity: 98%; MS (ESI+) m/z: 519.1 (M+1), 541.0 (M+Na+).

Example 23: methyl 1-(5-(5-((1H-indazol-5-yl)carbamoyl)-6-methyl-2-oxo-1,2,3,4-tetrahydropyrimidin-4-yl)-2-fluorobenzamido)cyclohexanecarboxylate (E23)

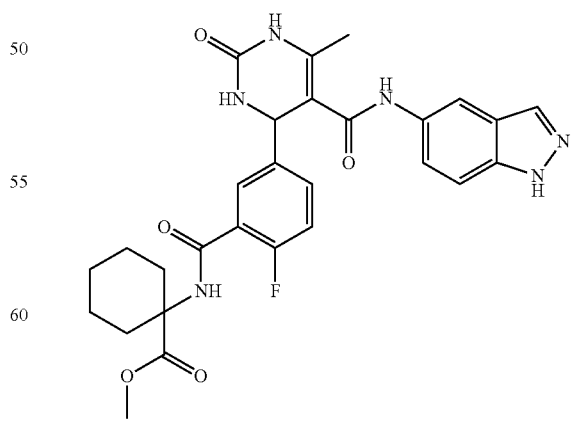

Compound E23 was prepared as described for Example 1, replacing 2-(aminomethyl)pyridine with methyl 1-aminocyclohexanecarboxylate. $^1$H NMR (400 MHz, cd$_3$od) δ 7.96 (s, 1H), 7.89 (s, 1H), 7.67 (dd, J=6.7, 2.3 Hz, 1H), 7.53 (ddd, J=8.1, 4.8, 2.4 Hz, 1H), 7.45 (d, J=9.0 Hz, 1H), 7.34 (dd, J=9.0, 1.7 Hz, 1H), 7.20 (dd, J=10.1, 8.7 Hz, 1H), 5.53 (s, 1H), 3.65 (s, 3H), 2.14 (s, 3H), 2.13-1.97 (m, 2H), 1.91-1.79 (m, 2H), 1.67-1.48 (m, 6H). $^{13}$C NMR (126 MHz, cd$_3$od) δ 174.74, 166.69, 164.86, 160.45, 158.46, 153.59, 139.86, 136.85, 133.43, 131.07, 131.00, 128.46, 122.02, 16.19, 116.00, 111.99, 109.79, 106.15, 103.54, 59.46, 55.85, 51.29, 31.97, 31.64, 24.93, 21.11, 21.08, 15.75. HPLC purity: 95%.

Example 24: 4-(4-fluoro-3-(((3-(methoxymethyl)-1,2,4-oxadiazol-5-yl)methyl)carbamoyl)phenyl)-N-(1H-indazol-5-yl)-6-methyl-2-oxo-1,2,3,4-tetrahydropyrimidine-5-carboxamide (E24)

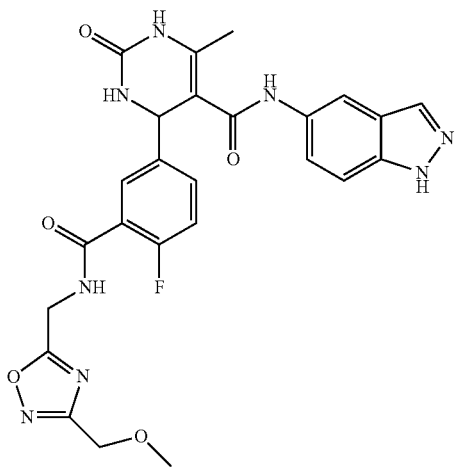 [SMILES: COCc1noc(CNC(=O)c2cc(C3NC(=O)NC(C)=C3C(=O)Nc3ccc4[nH]ncc4c3)ccc2F)n1]

Compound E24 was prepared as described for Example 1, replacing -(aminomethyl)pyridine with (3-(methoxymethyl)-1,2,4-oxadiazol-5-yl)methanamine. $^1$H NMR (400 MHz, Methanol-d$_4$) δ 7.96 (s, 1H), 7.89-7.83 (m, 2H), 7.56 (ddd, J=7.8, 4.7, 2.5 Hz, 1H), 7.44 (d, J=8.9 Hz, 1H), 7.31 (dd, J=8.9, 1.9 Hz, 1H), 7.22 (dd, J=10.7, 8.5 Hz, 1H), 5.54 (s, 1H), 4.81 (s, 2H), 4.52 (s, 2H), 3.39 (s, 3H), 2.13 (d, J=1.1 Hz, 3H). HPLC purity: 95%; MS (ESI+) m/z: 519.1 (M+1), 541.0 (M+Na+).

Example 25: 4-(4-fluoro-3-((1,7,7-trimethylbicyclo[2.2.1]heptan-2-yl)carbamoyl)phenyl)-N-(1H-indazol-5-yl)-6-methyl-2-oxo-1,2,3,4-tetrahydropyrimidine-5-carboxamide (E25)

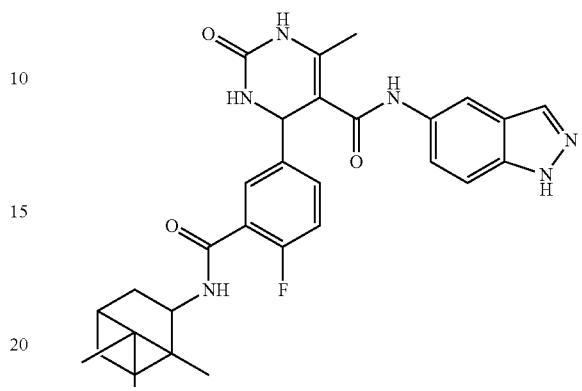

Compound E25 was prepared as described for Example 1, replacing -(aminomethyl)pyridine with 1,7,7-trimethylbicyclo[2.2.1]heptan-2-amine. (1:1)$^1$H NMR (500 MHz, DMSO) δ 12.93 (s, 1H), 9.62-9.56 (m, 1H), 8.77 (s, 1H), 8.17 (t, J=7.8 Hz, 0.5H), 8.01 (s, 1H), 7.96 (s, 1H), 7.67-7.59 (m, 1H), 7.53 (dd, J=15.6, 5.6 Hz, 1H), 7.47 (dd, J=12.2, 6.9 Hz, 0.5H), 7.43-7.36 (m, 3H), 7.27-7.19 (m, 1H), 5.45 (s, 1H), 4.28 (dd, J=17.5, 12.8 Hz, 0.5H), 3.96-3.89 (m, 1H), 2.17-2.11 (m, 0.5H), 2.08 (d, J=4.7 Hz, 3H), 1.79-1.58 (m, 2H), 1.57-1.48 (m, 1H), 1.27-0.98 (m, 3H), 0.94-0.74 (m, 9H). HPLC purity: 99%; MS (ESI+) m/z: 545.1 (M+1), 567.1 (M+Na+).

Example 26: 4-(4-fluoro-3-(methyl((5-methyl-1H-pyrazol-3-yl)methyl)carbamoyl)phenyl)-N-(1H-indazol-5-yl)-6-methyl-2-oxo-1,2,3,4-tetrahydropyrimidine-5-carboxamide (E26)

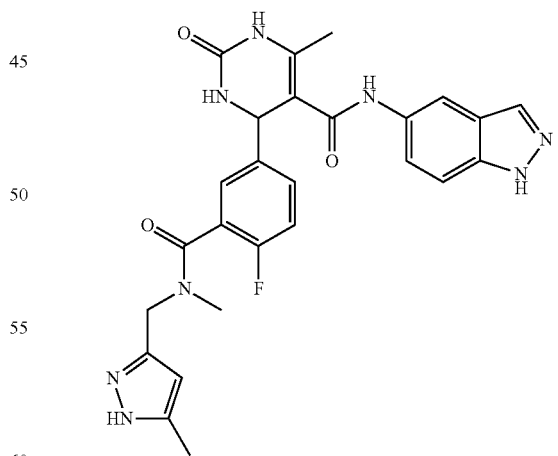

Compound E26 was prepared as described for Example 1, replacing -(aminomethyl)pyridine with N-methyl-1-(5-methyl-1H-pyrazol-3-yl)methanamine. $^1$H NMR (400 MHz, DMSO) δ 12.95 (s, 1H), 12.34 (s, 1H), 9.60 (s, 1H), 8.77 (s, 1H), 7.99-7.92 (m, 2H), 7.63 (broad s, 1H), 7.44-7.22 (m, 5H), 5.87 (s, 0.5H), 5.67 (s, 0.5H), 5.44 (s, 1H), 4.52 (s, 1H), 4.15 (broad s, 0.5H), 2.86 (s, 1.5H), 2.66 (s, 1.5H), 2.15 (d, J=25.6 Hz, 3H), 2.10-2.01 (m, 3H). HPLC purity: 96%; MS (ESI+) m/z: 517.0 (M+1), 539.0 (M+Na+).

Example 27: 4-(4-fluoro-3-((1-(2-methoxyphenyl)ethyl)carbamoyl)phenyl)-N-(1H-indazol-5-yl)-6-methyl-2-oxo-1,2,3,4-tetrahydropyrimidine-5-carboxamide (E27)

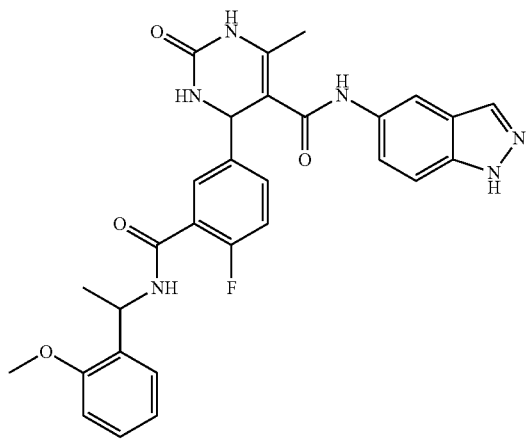 [SMILES: COc1ccccc1C(C)NC(=O)c1cc(C2NC(=O)NC(C)=C2C(=O)Nc2ccc3[nH]ncc3c2)ccc1F]

Compound E27 was prepared as described for Example 1, replacing -(aminomethyl)pyridine with 1-(2-methoxyphenyl)ethanamine. $^1$H NMR (400 MHz, DMSO-d$_6$) δ 12.94 (s, 1H), 9.60 (d, J=2.2 Hz, 1H), 8.78 (d, J=1.9 Hz, 1H), 8.69 (t, J=8.7 Hz, 1H), 8.00 (s, 1H), 7.97 (s, 1H), 7.65 (s, 1H), 7.55 (dt, J=6.8, 2.2 Hz, 1H), 7.44-7.36 (m, 3H), 7.34-7.18 (m, 3H), 6.98 (d, J=8.2 Hz, 1H), 6.88 (qd, J=7.4, 1.1 Hz, 1H), 5.45 (d, J=2.9 Hz, 1H), 5.42-5.33 (m, 1H), 3.83 (s, 3H), 2.10-2.04 (m, 3H), 1.32 (d, J=7.0 Hz, 3H). HPLC purity: 97%; MS (ESI+) m/z: 543.0 (M+1), 565.0 (M+Na+).

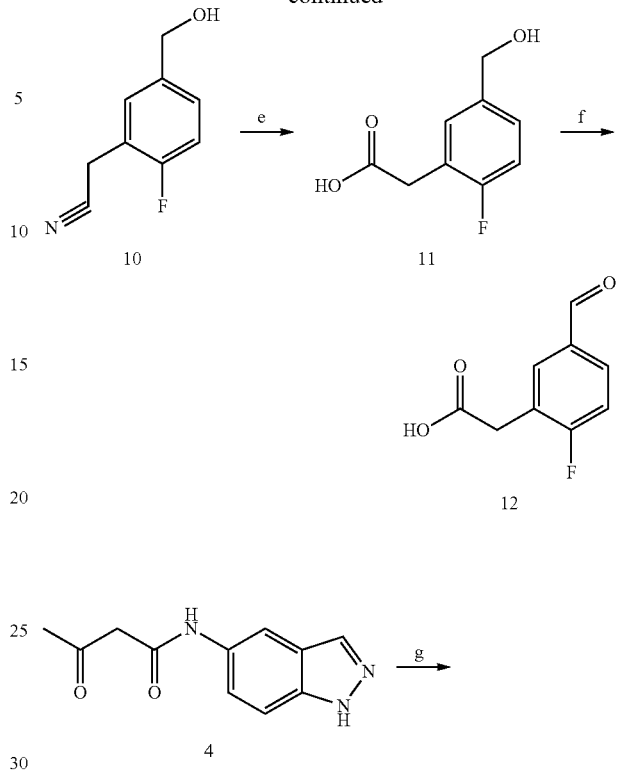

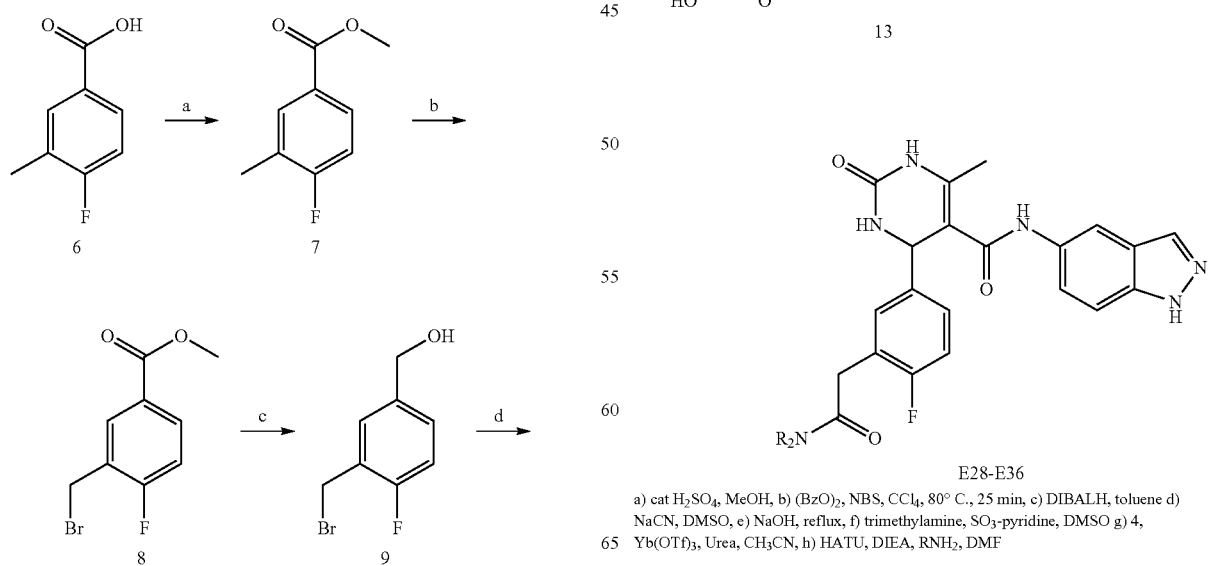

E28-E36 a) cat H$_2$SO$_4$, MeOH, b) (BzO)$_2$, NBS, CCl$_4$, 80° C., 25 min, c) DIBALH, toluene d) NaCN, DMSO, e) NaOH, reflux, f) trimethylamine, SO$_3$-pyridine, DMSO g) 4, Yb(OTf)$_3$, Urea, CH$_3$CN, h) HATU, DIEA, RNH$_2$, DMF

Preparation of methyl 4-fluoro-3-methylbenzoate (7)

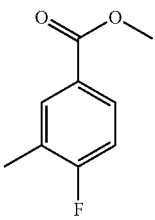

To a 100 mL round bottom flask with 40 mL of methanol was added 4-fluoro-3-methyl benzoic acid (4.0 g, 25.96 mmol) followed by concentrated $H_2SO_4$ (1.0 mL). The reaction vessel was equipped with a condenser and refluxed overnight at 65° C. Cooled down reaction and diluted with ether and $NaHCO_3$. The organic layer was washed with brine (3×), dried over $MgSO_4$, and concentrated at room temperature under reduced pressure to give methyl 4-fluoro-3-methylbenzoate (7) as a clear liquid (98% yield, 4.38 g). $^1$H NMR (400 MHz, DMSO-$d_6$) δ 7.90 (dd, J=7.5, 2.2 Hz, 1H), 7.83 (ddd, J=7.9, 5.0, 2.3 Hz, 1H), 7.27 (t, J=9.1 Hz, 1H), 3.83 (s, 3H), 2.28 (s, 3H). HPLC purity: 100%.

Preparation of methyl 3-(bromomethyl)-4-fluorobenzoate (8)

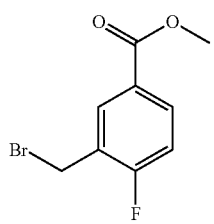

To a 250 mL closed pressure vessel was added methyl 4-fluoro-3-methylbenzoate (4.02 g, 23.91 mmol) dissolved in anhydrous carbon tetrachloride (40 mL). N-bromosuccinimide (3.83 g, 21.50 mmol) was then added followed by benzoyl peroxide (0.290 g, 1.20 mmol). The reaction stirred for 1 hour at 65° C. then cooled and filtered through celite with dichloromethane and concentrated. Purified using 0%-4% EtOAc/Hexanes using flash chromatography to give methyl 3-(bromomethyl)-4-fluorobenzoate (8) as a clear oil (82% yield, 4.31 g). $^1$H NMR (400 MHz, DMSO-$d_6$) δ 8.19 (dd, J=7.4, 2.3 Hz, 1H), 8.00 (ddd, J=8.7, 5.0, 2.3 Hz, 1H), 7.41 (dd, J=9.8, 8.7 Hz, 1H), 4.79 (d, J=1.1 Hz, 2H), 3.87 (s, 3H).

Preparation of (3-(bromomethyl)-4-fluorophenyl)methanol (9)

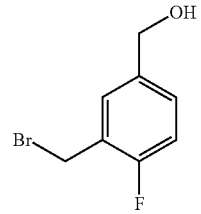 [SMILES: OCc1ccc(F)c(CBr)c1]

To a dry 250 mL flask was added toluene (30 mL) followed by 1M DIBAL in toluene (23.16 mL, 23.16 mmol). The flask was then cooled to 0° C. and then methyl 3-(bromomethyl)-4-fluorobenzoate (2.73 g, 11.05 mmol) in toluene (5 mL) was added. The reaction stirred for 2 hours and was then quenched (on ice) with 2N HCl to a pH of 2. The reaction was extracted with ethyl acetate (2×), the organic layers were combined and washed with NaCl (2×), dried over $MgSO_4$, and concentrated to give (3-(bromomethyl)-4-fluorophenyl)methanol (9) as a white solid (94% yield, 2.09 g). $^1$H NMR (500 MHz, DMSO-$d_6$) δ 7.46 (dd, J=7.5, 2.2 Hz, 1H), 7.32 (ddd, J=7.8, 5.1, 2.2 Hz, 1H), 7.18 (dd, J=10.0, 8.4 Hz, 1H), 5.28 (s, 1H), 4.69 (s, 2H), 4.46 (s, 2H).

Preparation of 2-(2-fluoro-5-(hydroxymethyl)phenyl)acetonitrile (10)

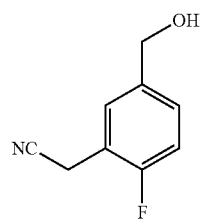

To a 250 mL round bottom flask was added (3-(bromomethyl)-4-fluorophenyl)methanol (2.06 g, 10.26 mmol) dissolved in DMSO (40 mL) followed by sodium cyanide (1.51 g, 30.77 mmol). After stirring at room temperature for 2 hours the reaction was diluted with $H_2O$ and ethyl acetate. The layers were separated and the aqueous layer was further extracted with ethyl acetate (2×). The organic layers were combined, washed 3× with NaCl, dried over $MgSO_4$, and concentrated. Using flash chromatography (15%-30% EtOAc/Hexanes) the residue was purified to obtain 2-(2-fluoro-5-(hydroxymethyl)phenyl)acetonitrile (10) as a clear liquid (1.50 g, 99% yield). $^1$H NMR (400 MHz, DMSO-$d_6$) δ 7.42 (dd, J=7.5, 2.1 Hz, 1H), 7.32 (ddd, J=7.7, 5.1, 2.1 Hz, 1H), 7.21 (dd, J=9.9, 8.4 Hz, 1H), 5.31 (t, J=5.7 Hz, 1H), 4.48 (d, J=5.6 Hz, 2H), 4.06 (s, 2H).

Preparation of 2-(2-fluoro-5-(hydroxymethyl)phenyl)acetic acid (11)

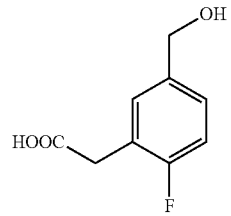 [SMILES: O=C(O)Cc1cc(CO)ccc1F]

To a 100 mL round bottom flask was added 2-(2-fluoro-5-(hydroxymethyl)phenyl)acetonitrile (0.881 g, 5.33 mmol) followed by 2N NaOH (20 mL). The reaction vessel was equipped with a condenser and refluxed overnight. After cooling the reaction down HCl was added to reach a pH of 3. The reaction was extracted with ethyl acetate (2×). The organic layers were combined, washed with NaCl (2×), dried over MgSO$_4$, and concentrated in vacuo to give 2-(2-fluoro-5-(hydroxymethyl)phenyl)acetic acid 11 as a white solid (0.969 g, 99% yield). $^1$H NMR (400 MHz, DMSO) δ 12.45 (s, 1H), 7.28-7.20 (m, 2H), 7.11 (dd, J=9.7, 8.5 Hz, 1H), 5.22 (s, 1H), 4.45 (s, 2H), 3.60 (s, 2H).

Preparation of 2-(2-fluoro-5-formylphenyl)acetic acid (12)

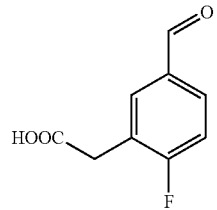 [SMILES: O=Cc1ccc(F)c(CC(=O)O)c1]

To a 100 mL round bottom flask at room temperature was added 2-(2-fluoro-5-(hydroxymethyl)phenyl)acetic acid (1.26 g, 7.58 mmol), triethylamine (8.46 mL, 60.66 mmol), and DMSO (20 mL). Sulfur trioxide pyridine complex (4.83 g, 30.33 mmol) in DMSO (20 mL) was then added to the reaction and the reaction was stirred for 20 minutes. The reaction was diluted with Na$_2$CO$_3$ then extracted with ether. To the aqueous layer 2N HCl was added to give a pH of 3. The aqueous layer was then extracted with ethyl acetate (2×). The ethyl acetate layers were combined and washed with NaCl (2×), dried over MgSO$_4$, and concentrated in vacuo to give 2-(2-fluoro-5-formylphenyl)acetic acid 12 as a white solid (1.24 g, 100% yield). $^1$H NMR (400 MHz, DMSO-d$_6$) δ 12.49 (s, 1H), 9.96 (s, 1H), 7.98-7.85 (m, 2H), 7.43 (dd, J=9.6, 8.3 Hz, 1H), 3.76 (d, J=1.4 Hz, 2H).

Preparation of 2-(5-(5-((1H-indazol-5-yl)carbamoyl)-6-methyl-2-oxo-1,2,3,4-tetrahydropyrimidin-4-yl)-2-fluorophenyl)acetic acid (13)

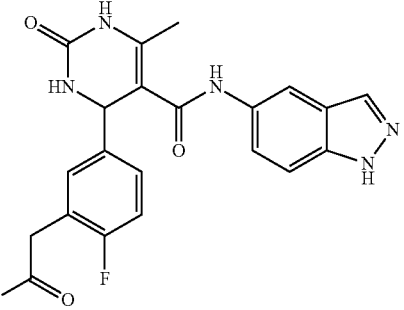

Compound 13 was prepared as described for compound 5, replacing 2-fluoro-5-formylbenzoic acid 2 with 2-(2-fluoro-5-formylphenyl)acetic acid 12 (72% yield). $^1$H NMR (400 MHz, DMSO-d$_6$) δ 12.80 (s, 1H), 12.53 (s, 1H), 9.54 (s, 1H), 8.69 (d, J=2.0 Hz, 1H), 7.99-7.92 (m, 2H), 7.58 (s, 1H), 7.42-7.33 (m, 2H), 7.26-7.16 (m, 2H), 7.11 (t, J=9.1 Hz, 1H), 5.38 (s, 1H), 3.56 (s, 2H), 2.04 (s, 3H).

Example 28: 4-(3-(2-((2,6-dimethylbenzyl)amino)-2-oxoethyl)-4-fluorophenyl)-N-(1H-indazol-5-yl)-6-methyl-2-oxo-1,2,3,4-tetrahydropyrimidine-5-carboxamide (E28)

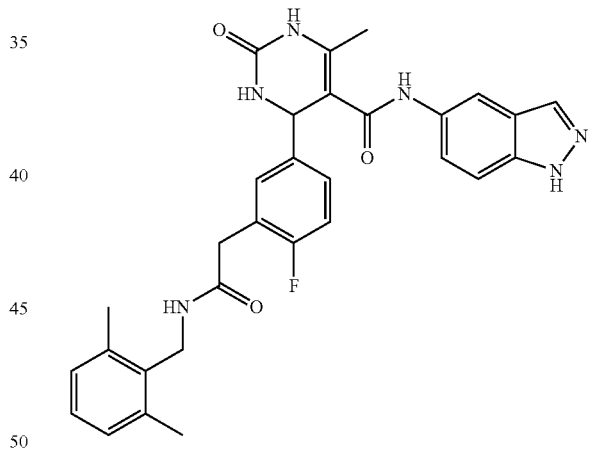

Compound E28 was prepared as described for Example 1, replacing 2-(aminomethyl)pyridine with (3-methoxyphenyl)methanamine and 5-(5-((1H-indazol-5-yl)carbamoyl)-6-methyl-2-oxo-1,2,3,4-tetrahydropyrimidin-4-yl)-2-fluorobenzoic acid 5 with 2-(5-(5-((1H-indazol-5-yl)carbamoyl)-6-methyl-2-oxo-1,2,3,4-tetrahydropyrimidin-4-yl)-2-fluorophenyl)acetic acid 13. $^1$H NMR (400 MHz, DMSO-d$_6$) δ 12.98 (s, 1H), 9.61 (s, 1H), 8.70 (s, 1H), 8.15 (s, 1H), 7.99 (d, J=21.7 Hz, 2H), 7.60 (s, 1H), 7.41 (s, 2H), 7.28-7.15 (m, 2H), 7.15-6.96 (m, 4H), 5.40 (s, 1H), 4.25 (s, 2H), 3.45 (s, 2H), 2.28 (s, 6H), 2.06 (s, 3H). $^{13}$C NMR (126 MHz, DMSO) δ 169.05, 165.61, 159.38, 152.90, 140.63, 138.38, 138.38, 137.69, 137.34, 135.06, 133.71, 132.53, 130.25, 128.34, 127.62, 123.83, 121.47, 115.41, 110.85, 110.25, 109.99, 105.84, 55.02, 37.86, 35.77, 19.83, 17.52. HPLC purity: 95%

Example 29: 4-(3-(2-((2,6-bis(trifluoromethyl)benzyl)amino)-2-oxoethyl)-4-fluorophenyl)-N-(1H-indazol-5-yl)-6-methyl-2-oxo-1,2,3,4-tetrahydropyrimidine-5-carboxamide (E29)

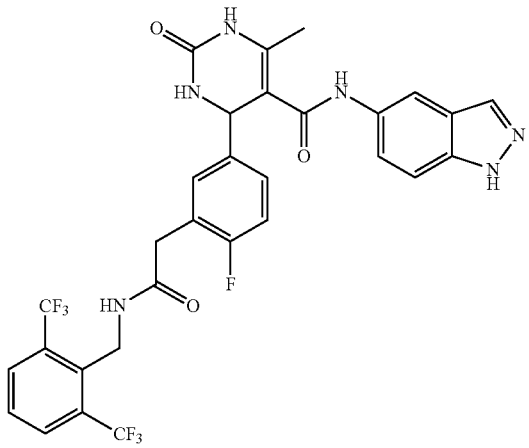 [SMILES: CC1=C(C(=O)Nc2ccc3[nH]ncc3c2)C(c2ccc(F)c(CC(=O)NCc3c(C(F)(F)F)cccc3C(F)(F)F)c2)NC(=O)N1]

Compound E29 was prepared as described for Example 28, replacing (3-methoxyphenyl)methanamine with 2,6-bis(trifluoromethyl)benzylamine. $^1$H NMR (500 MHz, DMSO-d$_6$) δ 12.93 (s, 1H), 9.55 (s, 1H), 8.68 (d, J=2.0 Hz, 1H), 8.35 (t, J=3.9 Hz, 1H), 8.13 (d, J=8.0 Hz, 2H), 8.00 (d, J=1.4 Hz, 1H), 7.96 (s, 1H), 7.82 (t, J=8.0 Hz, 1H), 7.58 (t, J=2.5 Hz, 1H), 7.44-7.36 (m, 2H), 7.26-7.16 (m, 2H), 7.10 (t, J=7.5 Hz, 1H), 5.40 (d, J=2.9 Hz, 1H), 4.48 (d, J=3.7 Hz, 2H), 3.43 (s, 2H), 2.09 (s, 3H). $^{13}$C NMR (126 MHz, DMSO) δ 168.04, 165.15, 158.92, 152.44, 140.10, 137.99, 136.88, 134.15, 133.24, 132.05, 130.872, 130.03, 126.54, 124.68, 123.01, 122.56, 121.03, 114.92, 114.75, 110.42, 109.77, 105.34, 54.52, 38.57, 36.23, 17.04. HPLC purity: 95%

Example 30: 4-(3-(2-((2,6-dimethoxybenzyl)amino)-2-oxoethyl)-4-fluorophenyl)-N-(1H-indazol-5-yl)-6-methyl-2-oxo-1,2,3,4-tetrahydropyrimidine-5-carboxamide (E30)

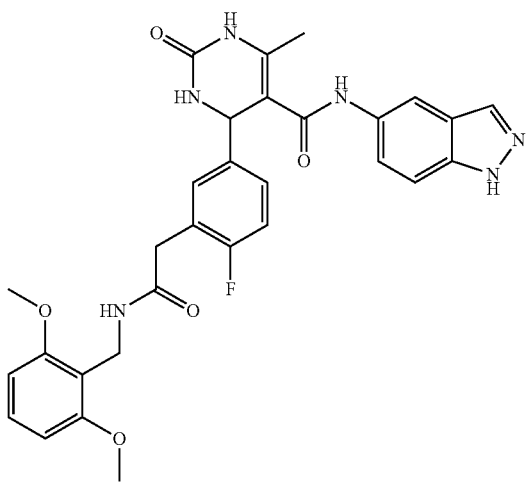 [SMILES: COc1cccc(OC)c1CNC(=O)Cc1cc(C2NC(=O)NC(C)=C2C(=O)Nc2ccc3[nH]ncc3c2)ccc1F]

Compound E30 was prepared as described for Example 28, replacing (3-methoxyphenyl)methanamine with 2,6-dimethoxybenzylamine. $^1$H NMR (500 MHz, DMSO-d$_6$) δ 12.93 (s, 1H), 9.56 (s, 1H), 8.67 (d, J=2.0 Hz, 1H), 7.98 (d, J=20.4 Hz, 2H), 7.70 (t, J=4.6 Hz, 1H), 7.57 (s, 1H), 7.45-7.35 (m, 2H), 7.27-7.15 (m, 3H), 7.09 (t, J=9.1 Hz, 1H), 6.64 (d, J=8.4 Hz, 2H), 5.40 (s, 1H), 4.24 (d, J=4.6 Hz, 2H), 3.74 (s, 6H), 3.42 (s, 2H), 2.06 (s, 3H). $^{13}$C NMR (126 MHz, DMSO) δ 168.73, 165.52, 159.29, 158.82, 152.86, 140.57, 138.21, 137.35, 133.68, 132.46, 130.37, 129.42, 126.78, 123.86, 123.00, 121.51, 115.26, 113.65, 110.81, 110.16, 105.92, 104.46, 56.10, 54.77, 35.41, 32.35, 17.22. HPLC purity: 97%.

Example 31: 4-(4-fluoro-3-(2-(2-(2-hydroxyethyl)morpholino)-2-oxoethyl)phenyl)-N-(1H-indazol-5-yl)-6-methyl-2-oxo-1,2,3,4-tetrahydropyrimidine-5-carboxamide (E31)

Compound E31 was prepared as described for Example 28, replacing (3-methoxyphenyl)methanamine with 2-(morpholin-2-yl)ethanol. $^1$H NMR (400 MHz, DMSO-d$_6$, 80° C.) δ 12.70 (s, 1H), 9.26 (s, 1H), 8.40 (s, 1H), 7.92 (s, 2H), 7.41-7.36 (m, 2H), 7.29 (s, 1H), 7.24-7.18 (m, 2H), 7.06 (dd, J=9.8, 8.3 Hz, 1H), 5.39 (d, J=3.0 Hz, 1H), 4.15 (s, 1H), 3.84-3.71 (m, 2H), 3.67 (s, 2H), 3.47 (broad s, 2H), 3.43-3.29 (m, 2H), 3.05 (broad s, 3H), 2.07 (d, J=2.5 Hz, 3H), 1.63-1.45 (m, J=6.8, 6.3 Hz, 2H). HPLC purity 97%.

Example 32: 4-(4-fluoro-3-(2-((furan-2-ylmethyl)(2-hydroxyethyl)amino)-2-oxoethyl)phenyl)-N-(1H-indazol-5-yl)-6-methyl-2-oxo-1,2,3,4-tetrahydropyrimidine-5-carboxamide (E32)

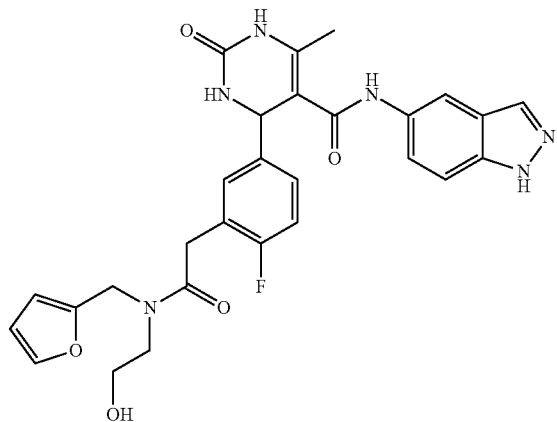 [SMILES: CC1=C(C(=O)Nc2ccc3[nH]ncc3c2)C(c2ccc(F)c(CC(=O)N(CCO)Cc3ccco3)c2)NC(=O)N1]

Compound E32 was prepared as described for Example 28, replacing (3-methoxyphenyl)methanamine with 2-((furan-2-ylmethyl)amino)ethanol. $^1$H NMR (400 MHz, DMSO-$d_6$, 80° C.) δ 12.67 (s, 1H), 9.22 (s, 1H), 8.35 (s, 1H), 7.92 (d, J=4.0 Hz, 2H), 7.53 (broad s, 1H), 7.44-7.35 (m, 2H), 7.24 (broad s, 3H), 7.06 (t, J=9.4 Hz, 1H), 6.37 (s, 1H), 6.26 (broad s, 1H), 5.41 (s, 1H), 4.58 (s, 2H), 4.37 (broad s, 1H), 3.79 (s, 2H), 3.51 (s, 2H), 3.41 (s, 2H), 2.10 (d, J=3.4 Hz, 3H). HPLC purity: 97%; MS (ESI+) m/z: 547.0 (M+1), 569.0 (M+Na+).

Example 33: 4-(3-(2-(((1-cyclopropylpiperidin-4-yl)methyl)amino)-2-oxoethyl)-4-fluorophenyl)-N-(1H-indazol-5-yl)-6-methyl-2-oxo-1,2,3,4-tetrahydropyrimidine-5-carboxamide (E33)

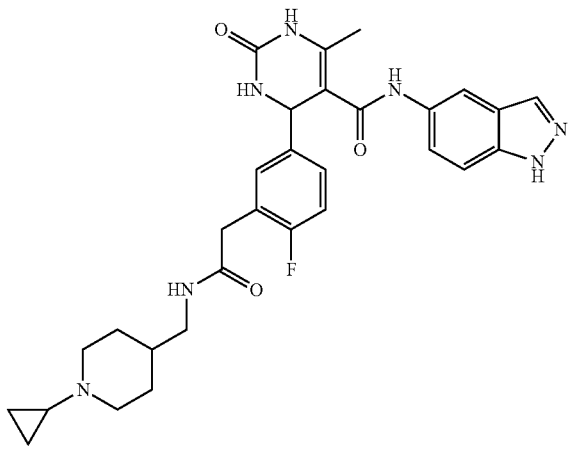 [SMILES: CC1=C(C(=O)Nc2ccc3[nH]ncc3c2)C(c2ccc(F)c(CC(=O)NCC3CCN(C4CC4)CC3)c2)NC(=O)N1]

Compound E33 was prepared as described for Example 28, replacing (3-methoxyphenyl)methanamine with (1-cyclopropylpiperidin-4-yl)methanamine. $^1$H NMR (400 MHz, DMSO) δ 12.91 (s, 1H), 9.52 (s, 1H), 8.67 (s, 1H), 7.98 (s, 1H), 7.94 (s, 1H), 7.56 (s, 1H), 7.42-7.35 (m, 2H), 7.22-7.14 (m, 3H), 7.11-7.05 (m, 1H), 5.37 (s, 1H), 3.47 (dd, J=14.9, 7.2 Hz, 1H), 3.38 (s, 2H), 2.79 (d, J=10.9 Hz, 2H), 2.11 (t, J=12.3 Hz, 2H), 2.04 (s, 3H), 1.63 (d, J=10.4 Hz, 2H), 1.52 (s, 1H), 1.25 (d, J=7.5 Hz, 2H), 0.36 (s, 2H), 0.22 (s, 2H). HPLC purity: 96%; MS (ESI+) m/z: 546.1 (M+1), 568.0 (M+Na+).

Example 34: 4-(4-fluoro-3-(2-(methyl((4-methyl-1H-imidazol-2-yl)methyl)amino)-2-oxoethyl)phenyl)-N-(1H-indazol-5-yl)-6-methyl-2-oxo-1,2,3,4-tetrahydropyrimidine-5-carboxamide (E34)

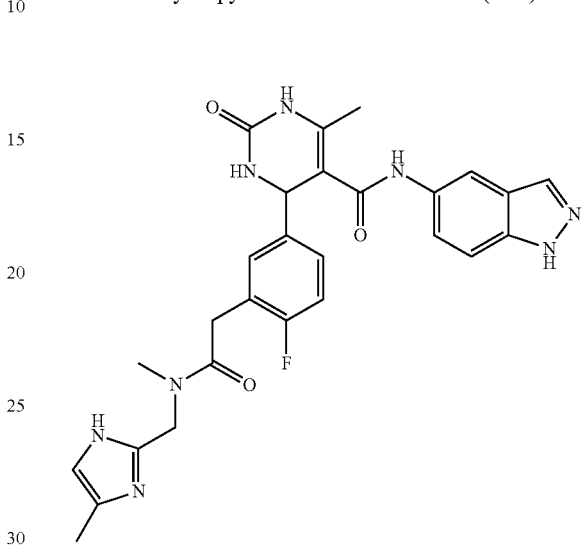

Compound E34 was prepared as described for Example 28, replacing (3-methoxyphenyl)methanamine with N-methyl-1-(4-methyl-1H-imidazol-2-yl)methanamine. $^1$H NMR (400 MHz, DMSO) δ 12.92 (s, 1H), 11.74 (s, 1H), 9.55 (s, 1H), 8.69 (s, 1H), 7.97 (d, J=14.9 Hz, 2H), 7.58 (s, 1H), 7.44-7.33 (m, 2H), 7.21-7.04 (m, 3H), 6.64 (s, 0.5H), 6.59 (s, 0.5H), 5.38 (s, 1H), 4.47 (s, 1H), 4.40 (s, 1H), 3.88 (s, 1H), 3.71 (s, 1H), 2.99 (s, 1.5H), 2.77 (s, 1.5H), 2.11-1.99 (m, 6H). HPLC purity: 95%; MS (ESI+) m/z: 531.1 (M+1), 553.0 (M+Na+).

Example 35: 4-(4-fluoro-3-(2-((furan-2-ylmethyl)(prop-2-yn-1-yl)amino)-2-oxoethyl)phenyl)-N-(1H-indazol-5-yl)-6-methyl-2-oxo-1,2,3,4-tetrahydropyrimidine-5-carboxamide (E35)

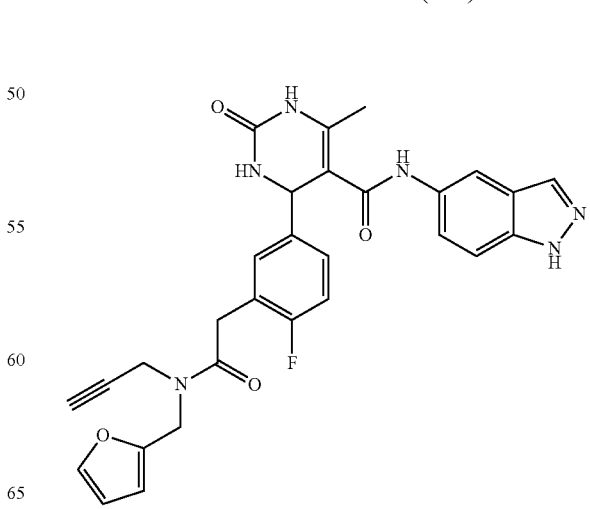

Compound E35 was prepared as described for Example 28, replacing (3-methoxyphenyl)methanamine with N-(furan-2-ylmethyl)prop-2-yn-1-amine. $^1$H NMR (400 MHz, DMSO-d$_6$) δ 12.92 (s, 1H), 9.55 (s, 1H), 8.69 (s, 1H), 7.97 (d, J=15.2 Hz, 2H), 7.66-7.55 (m, 2H), 7.43-7.35 (m, 2H), 7.23-7.13 (m, 2H), 7.09 (t, J=8.8 Hz, 1H), 6.43-6.39 (m, 1H), 6.38-6.28 (m, 1H), 5.39 (d, J=2.9 Hz, 1H), 4.69 (s, 1H), 4.51 (s, 1H), 4.22 (d, J=2.5 Hz, 1H), 4.04 (s, 1H), 3.83 (d, J=17.6 Hz, 2H), 3.29 (t, J=2.4 Hz, 0.5H), 3.13 (t, J=2.4 Hz, 0.5H), 2.04 (s, 3H). HPLC purity: 95%; MS (ESI+) m/z: 563.1 (M+1).

Example 36: 4-(4-fluoro-3-(2-(isobutyl(prop-2-yn-1-yl)amino)-2-oxoethyl)phenyl)-N-(1H-indazol-5-yl)-6-methyl-2-oxo-1,2,3,4-tetrahydropyrimidine-5-carboxamide (E36)

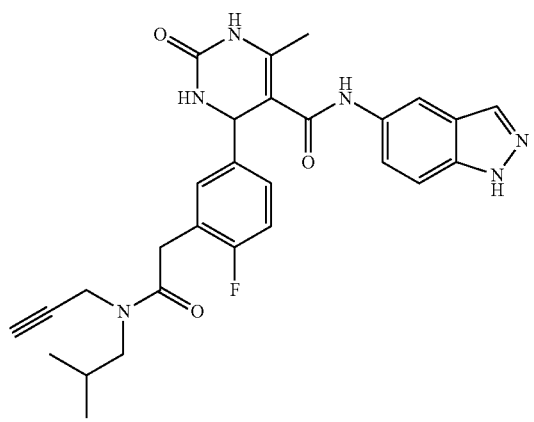 [SMILES: C#CCN(CC(C)C)C(=O)Cc1cc(C2NC(=O)NC(C)=C2C(=O)Nc2ccc3[nH]ncc3c2)ccc1F]

Compound E36 was prepared as described for Example 28, replacing (3-methoxyphenyl)methanamine with N-isobutylprop-2-yn-1-amine. $^1$H NMR (400 MHz, Methanol-d$_4$) δ 7.97 (s, 1H), 7.88 (s, 1H), 7.45 (d, J=9.0 Hz, 1H), 7.34-7.27 (m, 2H), 7.24 (ddd, J=6.7, 3.9, 2.4 Hz, 1H), 7.06 (t, J=9.0 Hz, 1H), 5.48 (s, 1H), 4.19-4.12 (m, 2H), 3.88 (d, J=3.5 Hz, 1H), 3.76 (d, J=8.1 Hz, 1H), 3.29-3.28 (m, 1H), 3.21 (dd, J=7.6, 3.7 Hz, 1H), 2.79 (t, J=2.4 Hz, 0.5H), 2.59 (t, J=2.5 Hz, 0.5H), 2.11 (s, 3H), 2.08-2.02 (m, 0.5H), 1.95 (p, J=6.9 Hz, 0.5H), 0.92 (dd, J=7.7, 6.6 Hz, 3H), 0.84 (dd, J=6.7, 3.1 Hz, 3H). HPLC purity: 97%.

General Synthetic Scheme 3

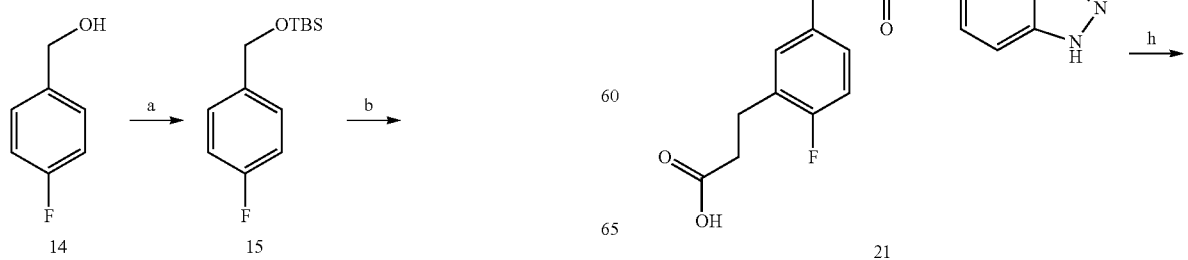

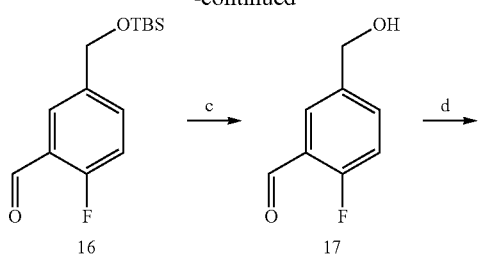

-continued

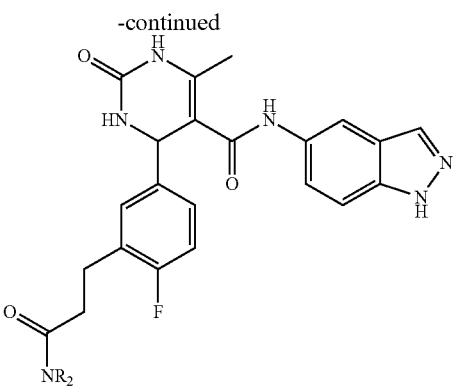

E37-E38 a)TBSCl, ImH, DIEA, DCM, b) sBuLi, TMEDA, THF, then DMF, c) TBAF, THF, d) Malonic acid, pyridine, piperidine, 100° C., e) Pd/H$_2$, EtOAc, f) SO$_3$-pyridine, Et$_3$N, DMSO, g) 4, Yb(OTf)$_3$, Urea, CH$_3$CN, h) HATU, DIEA, RNH$_2$, DMF Preparation of tert-butyl((4-fluorobenzyl)oxy)dimethylsilane (15)

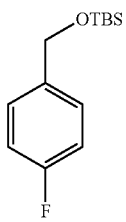 [SMILES: CC(C)(C)[Si](C)(C)OCc1ccc(F)cc1]

To a 100 mL flask was added 4-fluorobenzyl alcohol (2.0 g, 15.86 mmol), tert-butyldimethylsilyl chloride (3.58 g, 23.78 mmol), imidazole (1.08 g, 15.86 mmol), diisopropylethylamine (4.15 mL, 23.78 mmol) and dichloromethane (35 mL). The reaction was allowed to stir overnight at room temperature. Water was added to quench the reaction followed by dilution with dichloromethane. The layers were separated and the organic layer was then washed with NaCl (3×), dried over MgSO$_4$, and concentrated. The resulting residue was purified using flash chromatography (10% EtOAc/Hexanes) to give tert-butyl((4-fluorobenzyl)oxy)dimethylsilane as a clear oil (2.81 g, 77% yield). $^1$H NMR (500 MHz, DMSO-d$_6$) δ 7.32 (dd, J=8.4, 5.7 Hz, 2H), 7.18-7.10 (m, 2H), 4.66 (s, 2H), 0.88 (s, 9H), 0.05 (s, 6H).

Preparation of 5-(((tert-butyldimethylsilyl)oxy)methyl)-2-fluorobenzaldehyde (16)

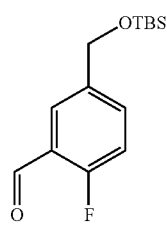 [SMILES: CC(C)(C)[Si](C)(C)OCc1ccc(F)c(C=O)c1]

To a 250 mL dry round bottom flask flushed with argon at −78° C. was added THF (18 mL) followed by tetramethylethylenediamine (1.38 mL, 9.20 mmol). Reaction stirred for 5 minutes. Sec-butyllithium (1.4 M in THF, 6.57 mL, 9.20) was then added slowly to the reaction. Reaction stirred for ten minutes. Tert-butyl((4-fluorobenzyl)oxy)dimethylsilane 15 (1.10 g, 4.60 mmol) in THF (18 mL) was then added to the reaction and stirred 1 hour keeping at −78° C. Dimethyl formamide (6 mL) was then slowly added giving a color change from yellow to clear and the reaction was allowed to warm to room temperature. Saturated ammonium chloride was added followed by dilution with water and ethyl acetate. The layers were separated. The aqueous layer was extracted with ethyl acetate (2×). The organic layers were combined and washed with brine (2×), dried over MgSO$_4$, and concentrated. Purification via flash chromatography (2% EtOAc/Hexanes) yielded as a clear oil 5-(((tert-butyldimethylsilyl)oxy)methyl)-2-fluorobenzaldehyde (0.950 g, 77% yield). $^1$H NMR (400 MHz, DMSO-d$_6$) δ 10.23 (s, 1H), 7.78 (dd, J=6.8, 2.3 Hz, 1H), 7.71-7.62 (m, 1H), 7.39 (dd, J=10.6, 8.6 Hz, 1H), 4.75 (s, 2H), 0.90 (s, 9H), 0.08 (s, 6H).

Preparation of 2-fluoro-5-(hydroxymethyl)benzaldehyde (17)

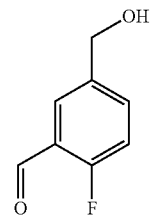 [SMILES: O=Cc1cc(CO)ccc1F]

To a dry 250 mL flask at 0° C. was added 5-(((tert-butyldimethylsilyl)oxy)methyl)-2-fluorobenzaldehyde 16 (4.22 g, 15.71 mmol), 1.0M tetra-n-butylammonium fluoride (31.41 mL, 31.41 mmol), and THF (20 mL). After six hours of stirring the reaction was diluted with water and then ethyl acetate. The layers were separated and the organic layer was washed with NaCl (2×), dried over MgSO$_4$, and concentrated. The residue was purified using flash chromatography (20% EtOAc/Hexanes) to give as an oil 2-fluoro-5-(hydroxymethyl)benzaldehyde (1.97 g, 74% yield). $^1$H NMR (500 MHz, DMSO-d$_6$) δ 10.23 (s, 1H), 7.79 (dq, J=7.1, 2.9, 2.5 Hz, 1H), 7.67 (ddq, J=7.4, 4.9, 2.4 Hz, 1H), 7.36 (ddd, J=10.4, 8.3, 1.6 Hz, 1H), 5.39 (s, 1H), 4.54 (d, J=5.5 Hz, 2H).

Preparation of (E)-3-(2-fluoro-5-(hydroxymethyl)phenyl)acrylic acid (18)

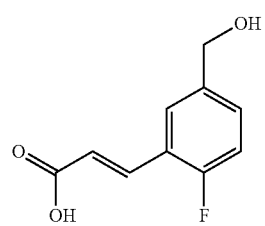 [SMILES: O=C(O)/C=C/c1cc(CO)ccc1F]

To a 250 mL flask was added 2-fluoro-5-(hydroxymethyl)benzaldehyde 17 (1.15 g, 6.76 mmol), malonic acid (0.70 g, 6.76 mmol), piperidine (1.34 mL, 13.52 mmol) and then pyridine (5.0 mL). The reaction was then stirred at 100° C. for four hours. After cooling, HCl was added to give a pH of 4 and then the reaction was diluted with water and extracted with ethyl acetate (1×). The organic layer was then washed with brine (2×), dried over $MgSO_4$, and concentrated. The residue was purified using flash chromatography (0%-5% EtOAc/Hexanes) to yield as a white powder (E)-3-(2-fluoro-5-(hydroxymethyl)phenyl)acrylic acid (1.06 g, 80% yield). $^1$H NMR (400 MHz, DMSO-$d_6$) δ 12.57 (s, 1H), 7.71 (dd, J=7.4, 2.1 Hz, 1H), 7.63 (d, J=16.1 Hz, 1H), 7.40 (ddd, J=7.7, 5.1, 2.1 Hz, 1H), 7.23 (dd, J=10.8, 8.5 Hz, 1H), 6.54 (d, J=16.1 Hz, 1H), 5.26 (s, 1H), 4.47 (t, J=2.2 Hz, 2H).

Preparation of 3-(2-fluoro-5-(hydroxymethyl)phenyl)propanoic acid (19)

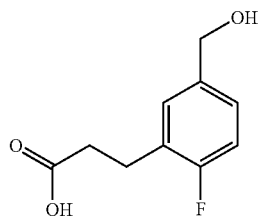 [SMILES: O=C(O)CCc1cc(CO)ccc1F]

To a dry 100 mL round bottom flask was added (E)-3-(2-fluoro-5-(hydroxymethyl)phenyl)acrylic acid 18 (0.480 g, 2.44 mmol) and ethyl acetate (30 mL). After bubbling through argon 10% Pd/C (0.05 g) was added. The reaction vessel was then vacuumed and the atmosphere was replaced with $H_2$. After stirring the reaction for 24 hours at room temperature it was filtered through celite with ethyl acetate (200 mL). The filtrate was concentrated to give as a white solid 3-(2-fluoro-5-(hydroxymethyl)phenyl)propanoic acid (0.438 g, 91% yield). $^1$H NMR (400 MHz, DMSO-$d_6$) δ 12.19 (s, 1H), 7.24 (dd, J=7.7, 2.2 Hz, 1H), 7.18 (ddd, J=7.7, 5.2, 2.2 Hz, 1H), 7.08 (dd, J=10.2, 8.3 Hz, 1H), 5.18 (t, J=5.7 Hz, 1H), 4.43 (d, J=5.5 Hz, 2H), 2.83 (t, J=7.7 Hz, 2H), 2.52 (t, J=7.6 Hz, 2H).

Preparation of 3-(2-fluoro-5-formylphenyl)propanoic acid (20)

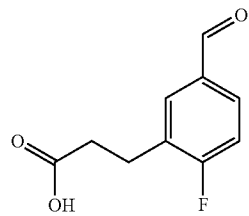 [SMILES: O=Cc1ccc(F)c(CCC(=O)O)c1]

Compound 20 was prepared as described for compound 11, replacing 2-(2-fluoro-5-(hydroxymethyl)phenyl)acetic acid 10 with 3-(2-fluoro-5-(hydroxymethyl)phenyl)propanoic acid 19 (79% yield). $^1$H NMR (500 MHz, DMSO-$d_6$) δ 12.25 (s, 1H), 9.95 (s, 1H), 7.90 (dd, J=7.5, 2.2 Hz, 1H), 7.85 (ddd, J=8.4, 5.2, 2.2 Hz, 1H), 7.40 (dd, J=9.9, 8.4 Hz, 1H), 2.92 (t, J=7.5 Hz, 2H), 2.59 (t, J=7.5 Hz, 2H).

Preparation of 3-(5-(5-(((1H-indazol-5-yl)carbamoyl)-6-methyl-2-oxo-1,2,3,4-tetrahydropyrimidin-4-yl)-2-fluorophenyl)propanoic acid (21)

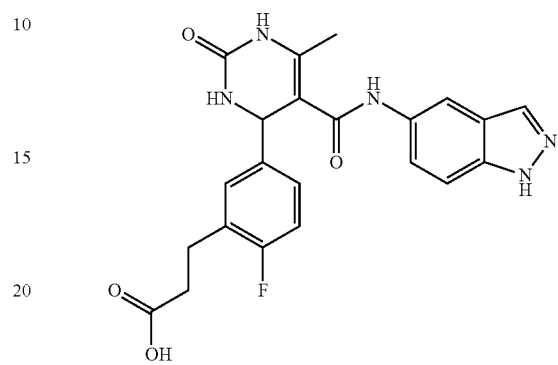

Compound 21 was prepared as described for compound 5, replacing 2-fluoro-5-formylbenzoic acid 2 with 3-(2-fluoro-5-formylphenyl)propanoic acid 20 (63% yield). $^1$H NMR (500 MHz, DMSO-$d_6$) δ 12.91 (s, 1H), 12.25 (s, 1H), 9.55 (s, 1H), 8.68 (d, J=2.0 Hz, 1H), 8.01-7.87 (m, 2H), 7.53 (s, 1H), 7.42 (d, J=8.9 Hz, 1H), 7.37 (dd, J=9.1, 1.8 Hz, 1H), 7.26-7.21 (m, 1H), 7.19-7.14 (m, 1H), 7.11 (t, J=9.2 Hz, 1H), 5.38 (d, J=2.8 Hz, 1H), 2.79 (t, J=7.9 Hz, 2H), 2.45 (t, J=7.8 Hz, 2H), 2.05 (s, 2H).

Example 37: 4-(4-fluoro-3-(3-(((5-methyloxazol-2-yl)methyl)amino)-3-oxopropyl)phenyl)-N-(1H-indazol-5-yl)-6-methyl-2-oxo-1,2,3,4-tetrahydropyrimidine-5-carboxamide (E37)

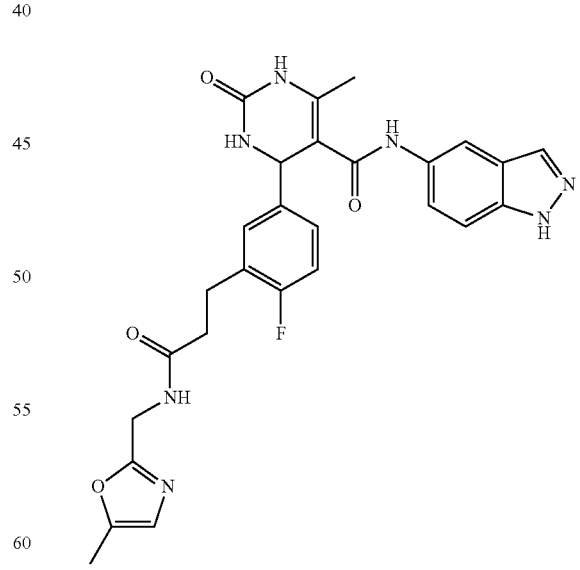

Compound E37 was prepared as described for Example 1, replacing 2-(aminomethyl)pyridine with (5-methyloxazol-2-yl)methanamine and 5-(5-(((1H-indazol-5-yl)carbamoyl)-6-methyl-2-oxo-1,2,3,4-tetrahydropyrimidin-4-yl)-2-fluorobenzoic acid 5 with 3-(5-(5-(((1H-indazol-5-yl)

carbamoyl)-6-methyl-2-oxo-1,2,3,4-tetrahydropyrimidin-4-yl)-2-fluorophenyl)propanoic acid 21 $^1$H NMR (400 MHz, DMSO-$d_6$) δ 12.92 (s, 1H), 9.55 (s, 1H), 8.68 (s, 1H), 8.50 (t, J=5.8 Hz, 1H), 7.96 (d, J=12.7 Hz, 2H), 7.52 (s, 1H), 7.38 (q, J=8.9 Hz, 2H), 7.21 (d, J=7.3 Hz, 1H), 7.17-7.05 (m, 2H), 6.72 (d, J=1.4 Hz, 1H), 5.36 (s, 1H), 4.30-4.23 (m, 2H), 2.82-2.71 (m, 2H), 2.39-2.29 (m, 2H), 2.23 (s, 3H), 2.04 (s, 3H). HPLC purity: 95%; MS (ESI+) m/z: 532.0 (M+1), 554.0 (M+Na+).

Example 38: 4-(4-fluoro-3-(3-oxo-3-(phenethyl-amino)propyl)phenyl)-N-(1H-indazol-5-yl)-6-methyl-2-oxo-1,2,3,4-tetrahydropyrimidine-5-carboxamide (E38)

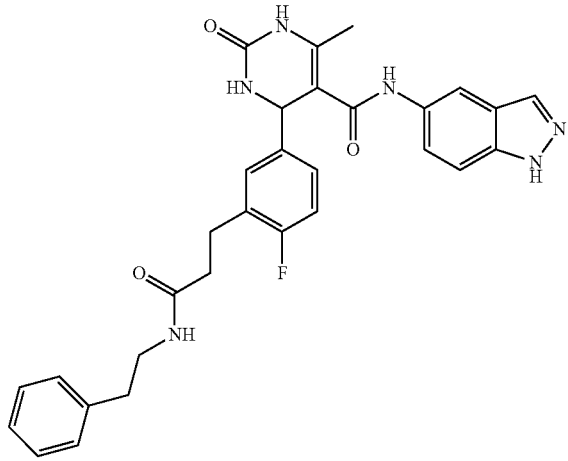 [SMILES: CC1=C(C(=O)Nc2ccc3[nH]ncc3c2)C(c2ccc(F)c(CCC(=O)NCCc3ccccc3)c2)NC(=O)N1]

Compound E38 was prepared as described for Example 38, replacing (5-methyloxazol-2-yl)methanamine with 2-phenylethanamine. $^1$H NMR (500 MHz, DMSO-$d_6$) δ 12.93 (s, 1H), 9.56 (s, 1H), 8.68 (s, 1H), 8.03-7.88 (m, 3H), 7.52 (s, 1H), 7.40 (q, J=9.0 Hz, 2H), 7.30-7.07 (m, 8H), 5.38 (s, 1H), 3.23 (q, J=6.9 Hz, 2H), 2.76 (t, J=8.1 Hz, 2H), 2.66 (t, J=7.5 Hz, 2H), 2.28 (broad s, 2H), 2.06 (s, 3H). HPLC purity: 98%; MS (ESI+) m/z: 563.0 (M+Na+).

Assays for Inhibition of GRKs

GRK1, 2 and 5 kinetic assays were conducted in a buffer containing 20 mM HEPES pH 7.0, 5 μM ATP, 2 mM MgCl$_2$, and 0.025% DDM with 50 nM GRK and either 500 nM bROS or 500 nM soluble substrate tubulin in 5 min reactions. The low salt concentration and DDM were used to maximize GRK activity and disrupt small molecule aggregates from forming, respectively. Reactions were quenched with SDS loading buffer, separated via SDS-PAGE, dried and exposed with a phosphorimaging screen prior to quantification via Typhoon imager, as previously reported (see Thal et al., ACS Chemical Biology 7(11):1830-1839 (2012)). Data was analyzed and inhibition curves were fit via GraphPad Prism.

Rho-associated coiled-coil kinase (ROCK) assays were performed with the ADP-Glo system using 0.1 μg ROCK1 and 1 μg S6K substrate, and 100 μM ATP for 60 min prior to addition of ADP-GLO Reagent, and allowed to incubate for an additional 40 min prior to the addition of the Kinase Detection Reagent and imaging on a PHERASTAR system. Results of the assays for inhibition of GRKs are shown in the Table, below.

| Example No. | Compound Name | GRK1 IC$_{50}$ (μM) | GRK2 IC$_{50}$ (μM) | GRK5 IC$_{50}$ (μM) | ROCK1 IC$_{50}$ (μM) |
|---|---|---|---|---|---|
|  | GSK180736A | >100 | 0.77 | 100 | 0.078 |
| 1 | E01 | 3.9 | 0.15 | 0.38 | 0.011 |
| 2 | E02 | >100 | 0.12 | 5.0 | 0.061 |
| 3 | E03 | >100 | 0.28 | 6.20 | 0.023 |
| 4 | E04 | 11.9 | 0.20 | 0.80 | 0.021 |
| 5 | E05 | 16.3 | 0.060 | 2.30 | 0.057 |
| 6 | E06 | >100 | 0.46 | 8.10 | 0.050 |
| 7 | E07 | >100 | 5.15 | >100 | >100 |
| 8 | E08 | 0.070 | 2.60 | 5.40 | 0.017 |
| 9 | E09 | >100 | 0.13 | >100 | 6.70 |
| 10 | E10 | >100 | 0.070 | 63 | 5.8 |
| 11 | E11 | >100 | 0.13 | >100 | >10 |
| 12 | E12 | >100 | 4.3 | >100 | 0.19 |
| 13 | E13 | >100 | 2.7 | >100 | 1.9 |
| 14 | E14 | >100 | 0.23 | 58 | 0.29 |
| 15 | E15 | >100 | 1.9 | 68 | 0.15 |
| 16 | E16 | 71 | 0.69 | 4.7 | 0.069 |
| 17 | E17 | >100 | 1.2 | >100 | >10 |
| 18 | E18 | >100 | 0.42 | 3.8 | 0.097 |
| 19 | E19 | >100 | 51 | >100 |  |
| 20 | E20 | >100 | 0.74 | 94 |  |
| 21 | E21 | >100 | 14.6 | >100 |  |
| 22 | E22 | 3.5 | 0.18 | 0.41 |  |
| 23 | E23 | 67 | 0.82 | 22 |  |
| 24 | E24 | 18 | 0.24 | 0.14 |  |
| 25 | E25 | >100 | 5.2 | 89 |  |
| 26 | E26 | >100 | 1.2 | 40 |  |
| 27 | E27 | 14 | 0.32 | 2.4 |  |
| 28 | E28 | >100 | 25 | >100 | 0.45 |
| 29 | E29 | >100 | >100 | >100 | 0.40 |
| 30 | E30 | >100 | 0.45 | >100 | 0.20 |
| 31 | E31 | >100 | 1.5 | 10.8 |  |
| 32 | E32 | 21 | 0.50 | 1.7 |  |
| 33 | E33 | >100 | 0.68 | 11.8 |  |
| 34 | E34 | >100 | 1.2 | 40 |  |
| 35 | E35 | >100 | 0.96 | 4.4 |  |
| 36 | E36 | >100 | 2.6 | 8.9 |  |
| 37 | E37 | 74 | 4.0 | 66 |  |
| 38 | E38 | >100 | 7.0 | >100 |  |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A compound of Formula (I), or a pharmaceutically acceptable salt thereof:

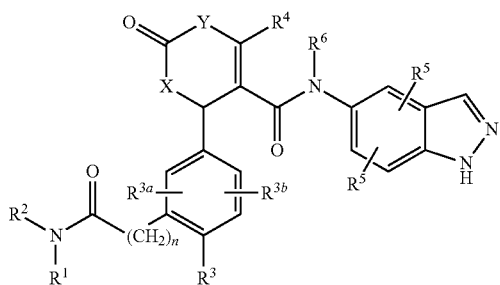

wherein:

n is 0, 1, or 2;

X and Y are each $N(R^7)$, or one of X and Y is $N(R^7)$ and the other is $CH_2$;

$R^1$ is H, $C_{1-8}$alkyl, $C_{2-8}$alkenyl, $C_{2-8}$alkynyl, $C_{3-8}$ cycloalkyl, $C_{3-8}$ cycloalkenyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;

$R^2$ is $C_{1-8}$alkyl, $C_{2-8}$alkenyl, $C_{3-8}$ cycloalkyl, $C_{3-8}$ cycloalkenyl, $C_{1-4}$ alkylene-cycloalkyl, $C_{0-4}$ alkylene-heterocycloalkyl, $C_{1-4}$ alkylene-aryl, $C_{1-4}$ alkylene-heteroaryl, $C_{3-8}$ cycloalkylene-aryl, or $C_{3-8}$ cycloalkylene-heteroaryl;

or $R^1$ and $R^2$, together with the nitrogen atom to which they are attached, form a 3-8-membered heterocycloalkyl group;

$R^3$ is H, F, Cl, or $CH_3$;

$R^{3a}$ and $R^{3b}$ are each independently H, F, Cl, or $CH_3$;

$R^4$ is H, $CH_3$, $CF_3$, $CH_2CH_3$, or $CH_2CH_2CH_3$;

each $R^5$ independently is H or F;

$R^6$ is H or $C_{1-6}$ alkyl; and each $R^7$ independently is H or $C_{1-6}$ alkyl.

2. The compound of claim 1, wherein $R^1$ is:
(i) H; or
(ii) $CH_3$, $CH_2CH_2OH$, or $CH_2CCH$.

3. The compound of claim 1, wherein $R^1$ is:
(i) $C_{3-8}$ cycloalkyl or $C_{3-8}$ cycloalkenyl; or
(ii) $C_{1-4}$ alkylene-aryl or $C_{1-4}$ alkylene-heteroaryl; or
(iii) $C_{3-8}$ cycloalkylene-aryl or $C_{3-8}$ cycloalkylene-heteroaryl.

4. The compound of claim 1, wherein:
(i) $R^2$ is methyl, ethyl, isopropyl, or sec-butyl; or
(ii) $R^2$ comprises

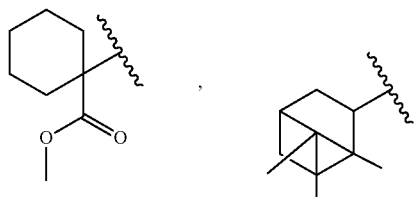

azepanyl, tetrahydropyranyl, morpholinyl, piperidinyl,

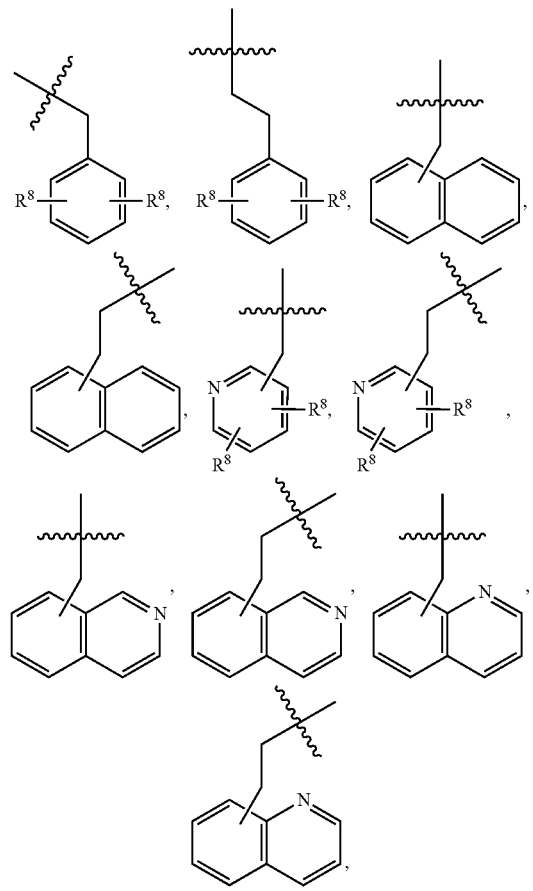

oxadiazolyl, oxazolyl, pyrazolyl, furanyl, or primidazolyl, wherein each $R^8$ independently is H, halo, $C_{1-4}$ alkyl, or $C_{1-4}$ alkoxyl; or (iii) $R^1$ and $R^2$, together with the nitrogen atom to which they are attached form a 3-8-membered heterocycloalkyl group comprising morpholinyl.

5. The compound of claim 4, wherein:
(i) beach $R^8$ is H; or
(ii) one $R^8$ is H and one $R^8$ is F or Cl; or
(iii) one $R^8$ is H and one $R^8$ is $CH_3$ or $CF_3$; or
(iv) one $R^8$ is H and one $R^8$ is $OCH_3$ or $OCF_3$; or
(v) each $R^8$ independently is F or Cl; or
(vi) each $R^8$ independently is $CH_3$ or $CF_3$; or
(v) each $R^8$ independently is $OCH_3$ or $OCF_3$.

6. The compound of claim 1, wherein each $R^8$ is ortho.

7. The compound of claim 1, wherein $R^2$ comprises $CH_3$, isopropyl, sec-butyl, $CH_2$-pyrazolyl,

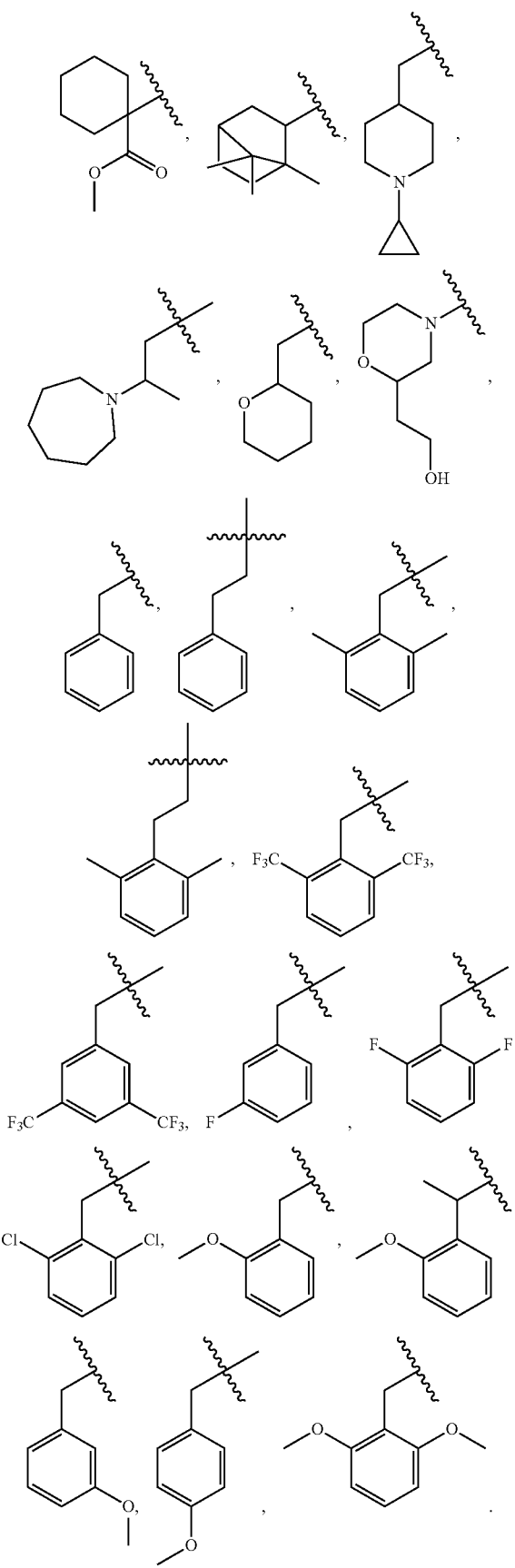

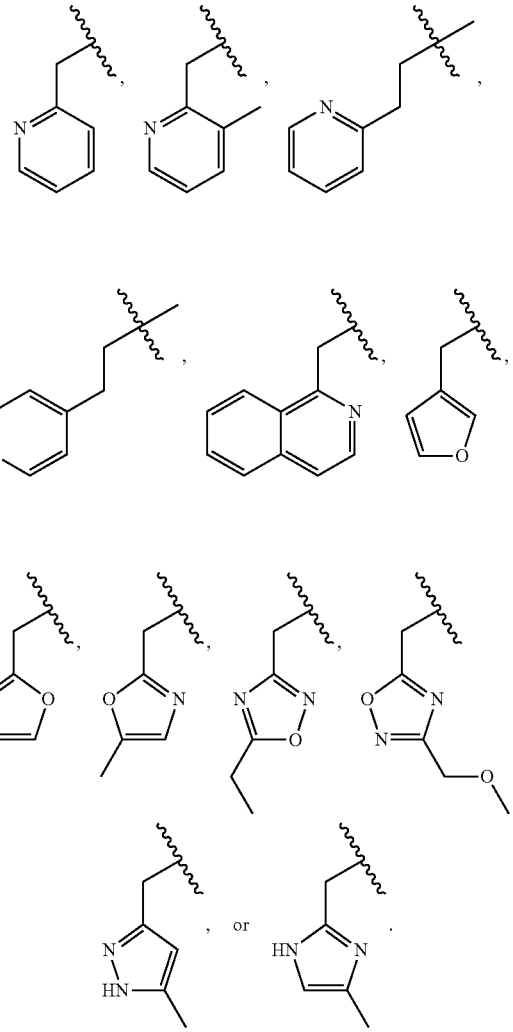

8. The compound of claim 1, wherein $R^3$ is:
(i) H, Cl, or $CH_3$; or
(ii) F.

9. The compound of claim 1, wherein:
(i) each of $R^{3a}$ and $R^{3b}$ are H; or
(ii) $R^{3a}$ is H, and $R^{3b}$ is F, Cl, or $CH_3$; or
(iii) each of $R^{3a}$ and $R^{3b}$ independently is F, Cl, or $CH_3$.

10. The compound of claim 1, wherein $R^4$ is:
(i) H, $CH_2CH_3$, or $CH_2CH_2CH_3$; or
(ii) $CH_3$ or $CF_3$.

11. The compound of claim 1, wherein:
(i) each $R^5$ is H; or
(ii) each $R^5$ is F; or
(iii) one $R^5$ is H and one $R^5$ is F.

12. The compound of claim 1, wherein $R^6$ is H.

13. The compound of claim 1, wherein:
(i) X and Y are each NH; or
(ii) X is NH and Y is $CH_2$; or
(iii) X is $CH_2$, and Y is NH.

14. The compound of claim 1 having a structure selected from the group consisting of:
E01
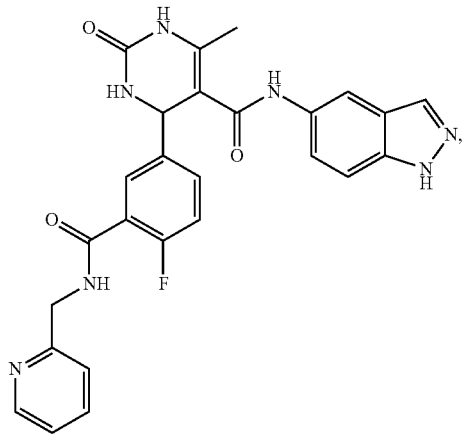
E02
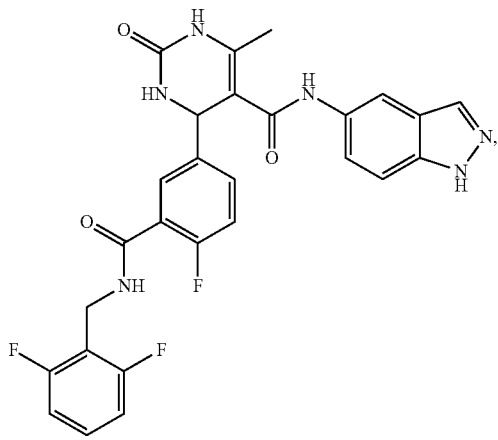
E03
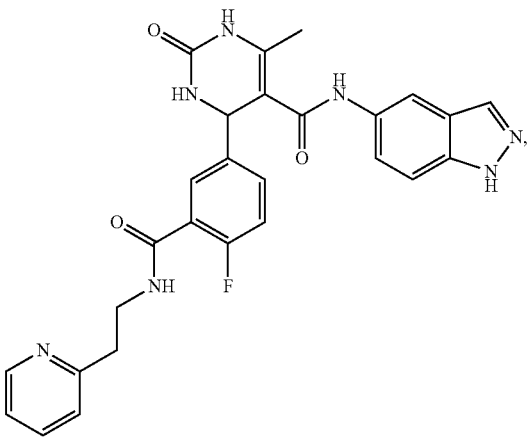
-continued
E04
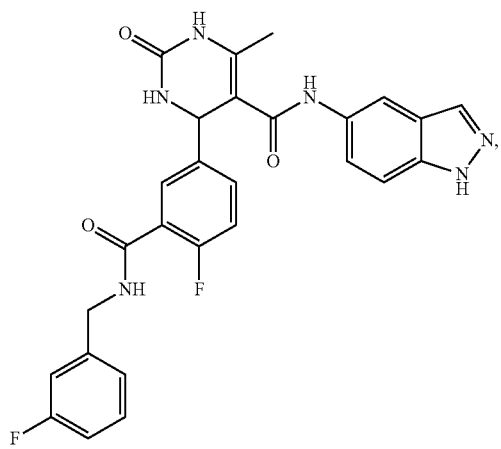
E05
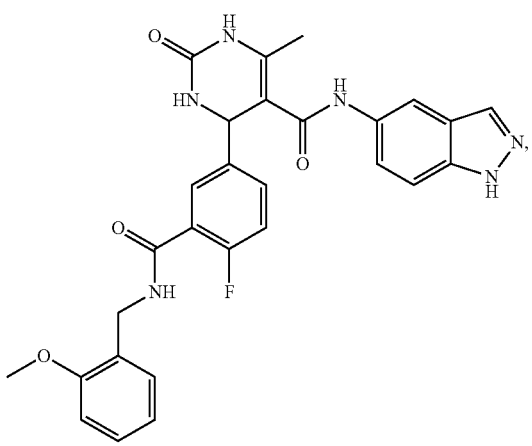
E06
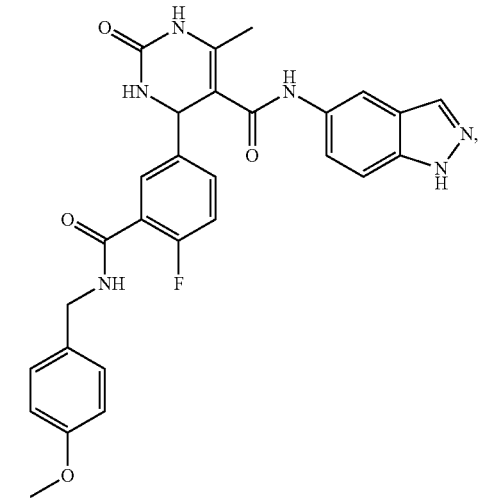

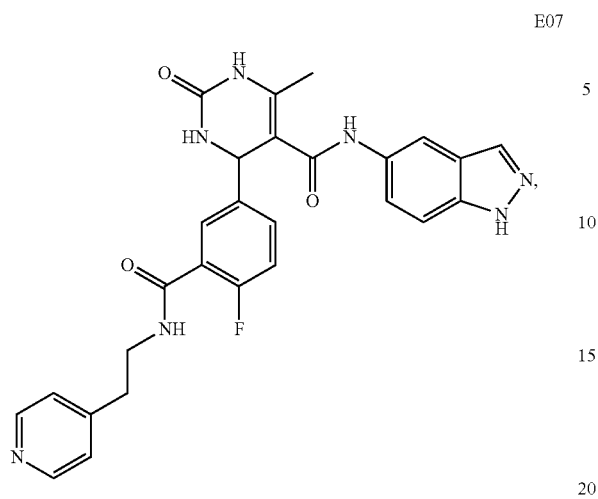
E07
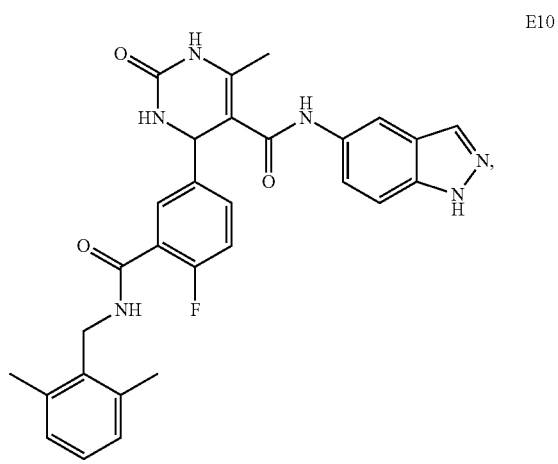
E10
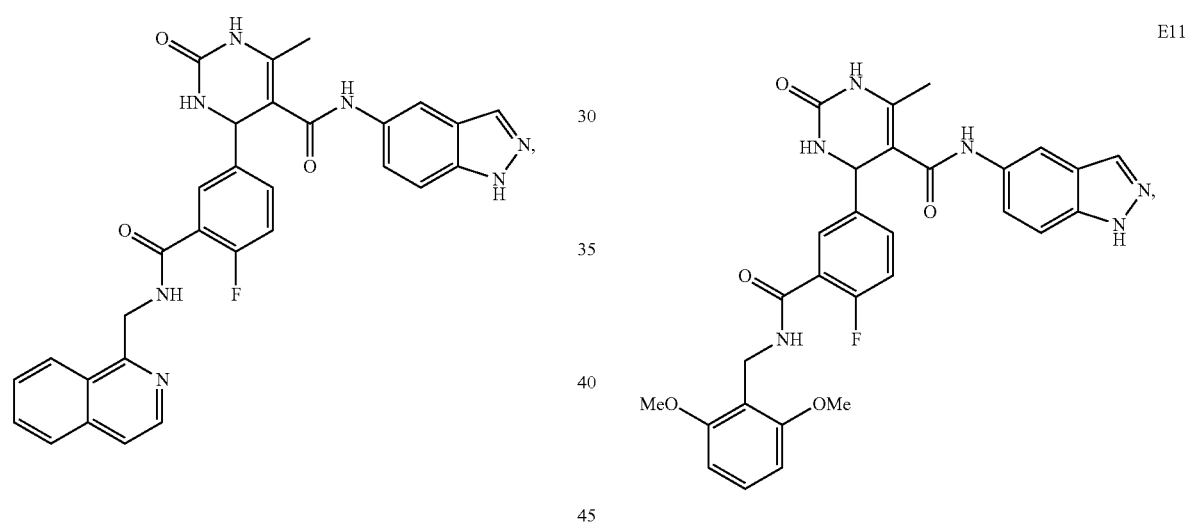
E08
E11
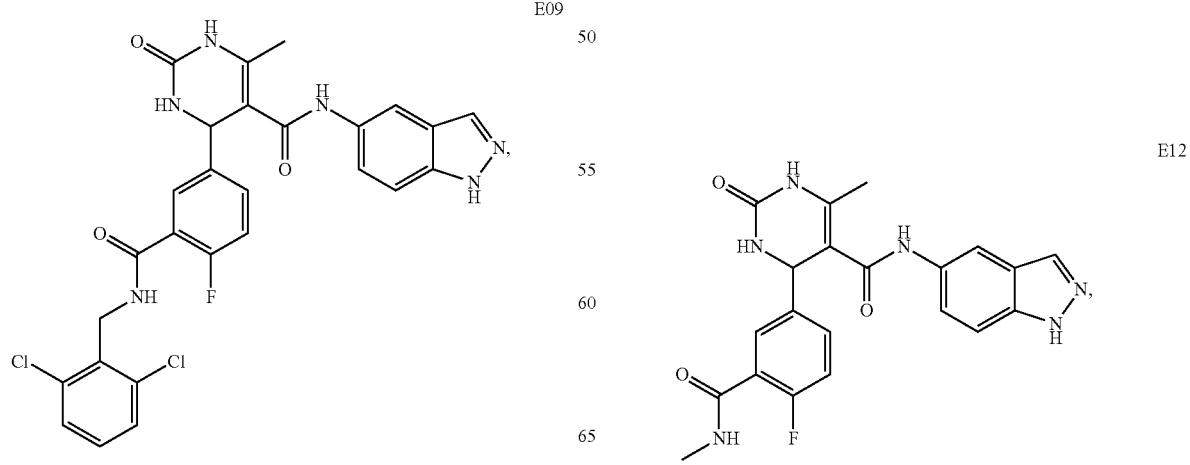
E09
E12

E13
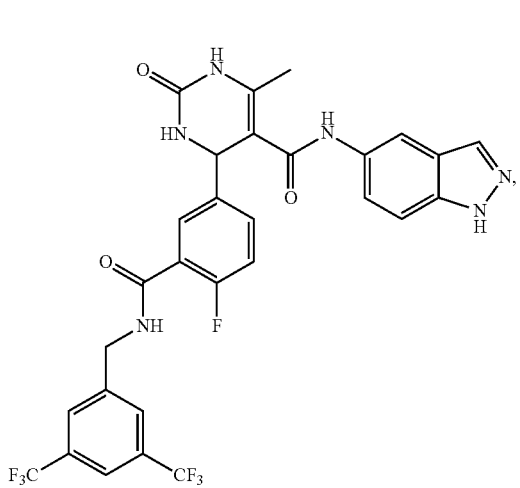
E16
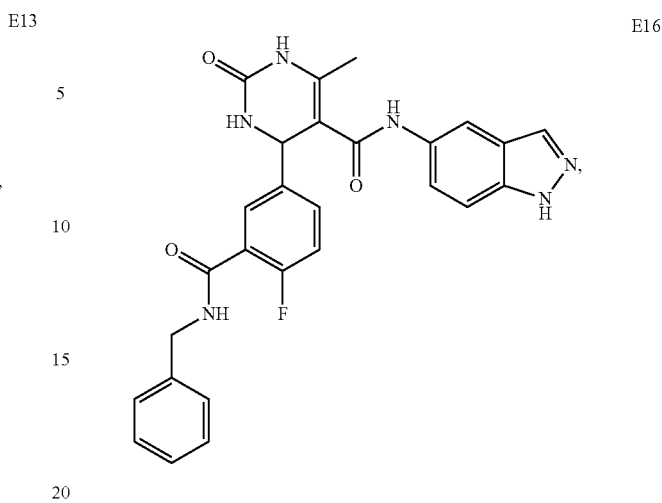
E14
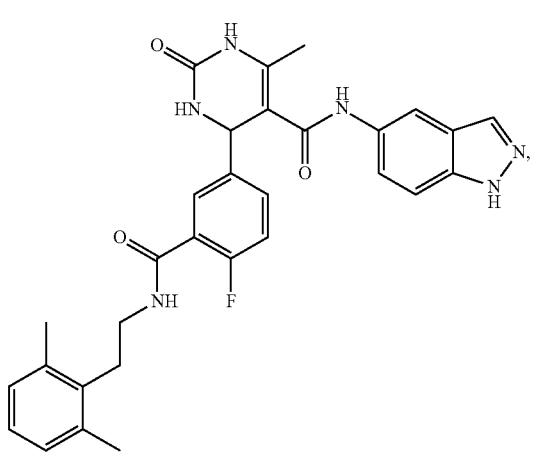
E17
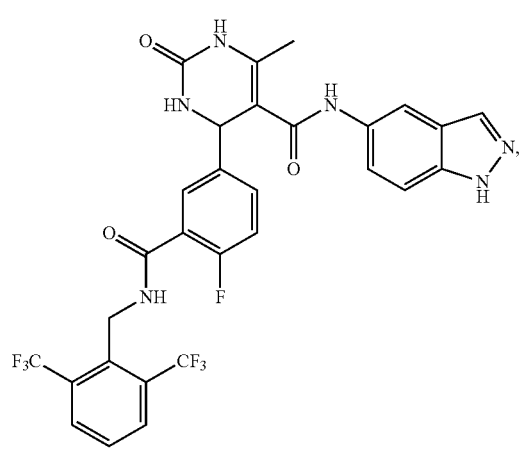
E15
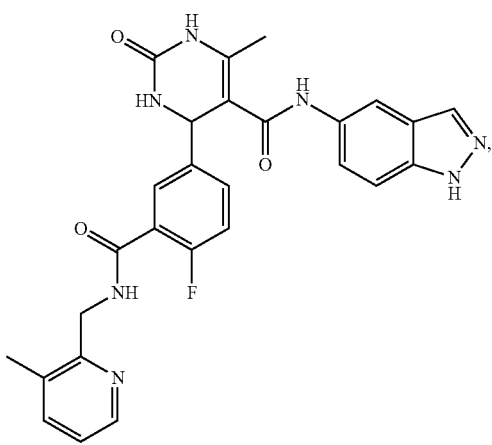
E18
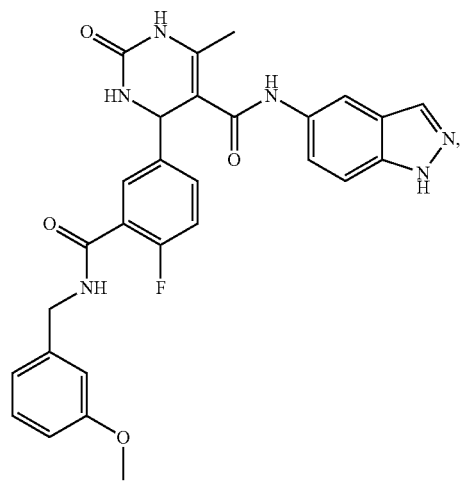

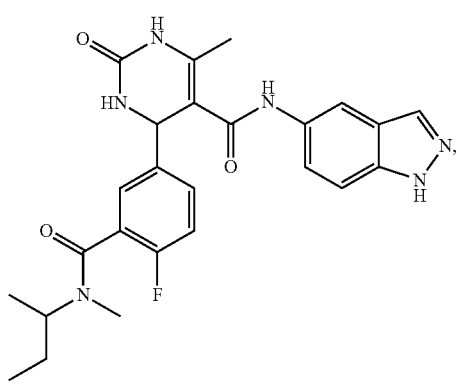
E19
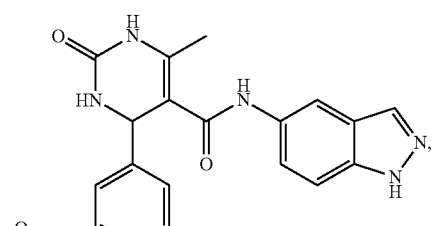
E22
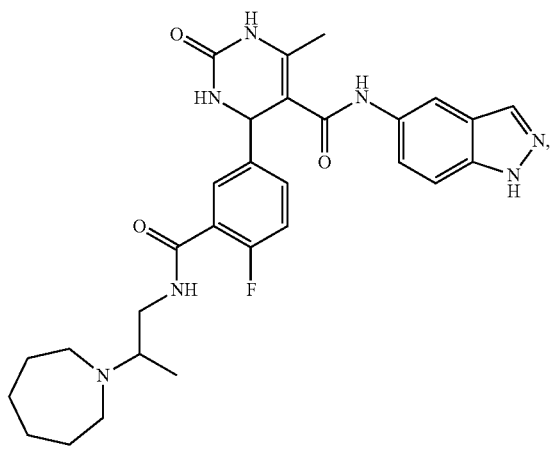
E20
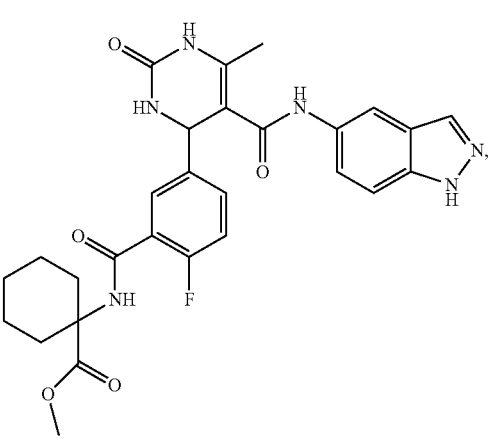
E23
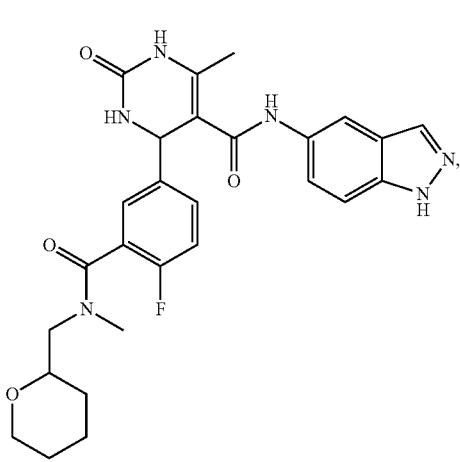
E21
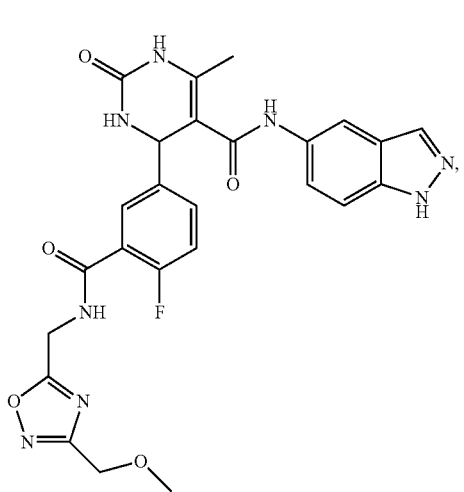
E24

E25
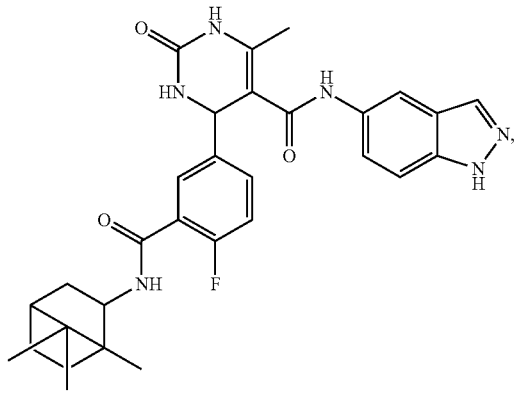
E26
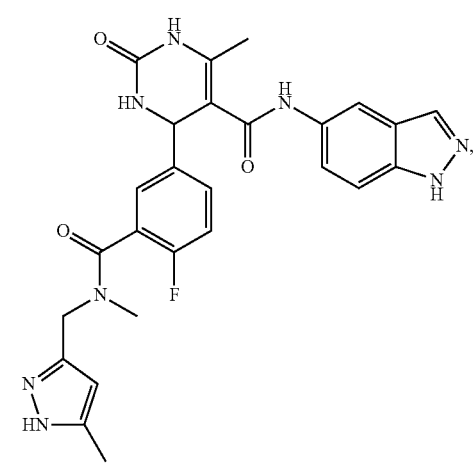
E27
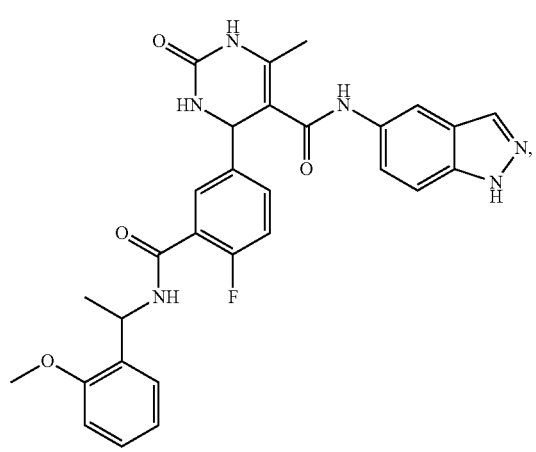
E28
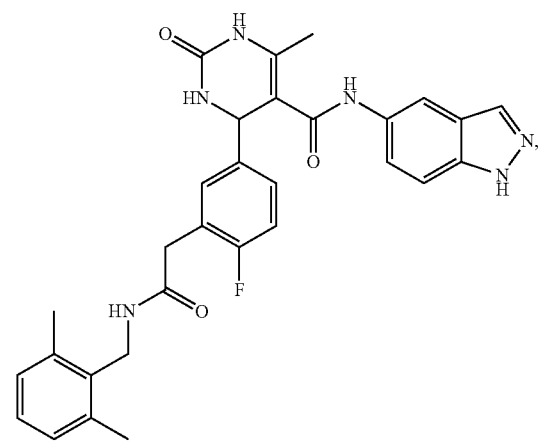
E29
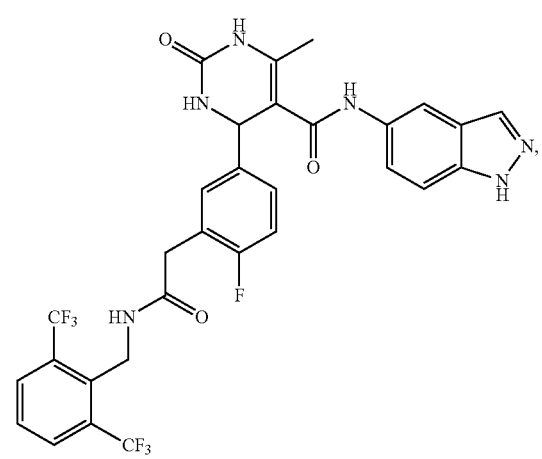
E30
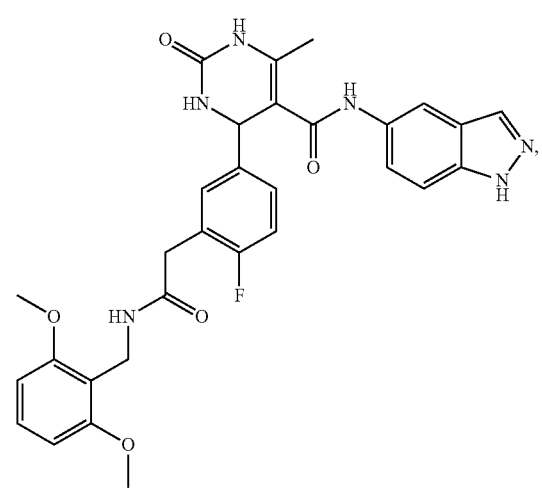

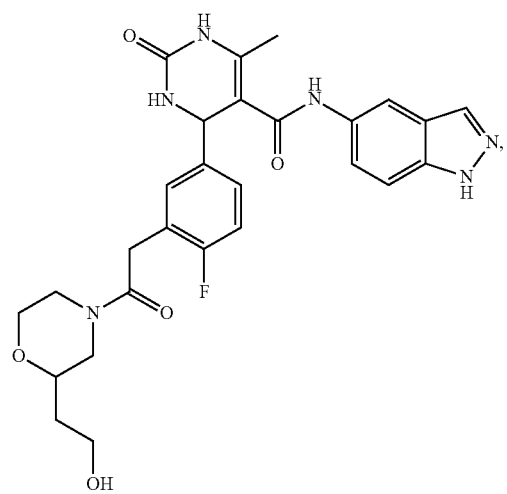
E31
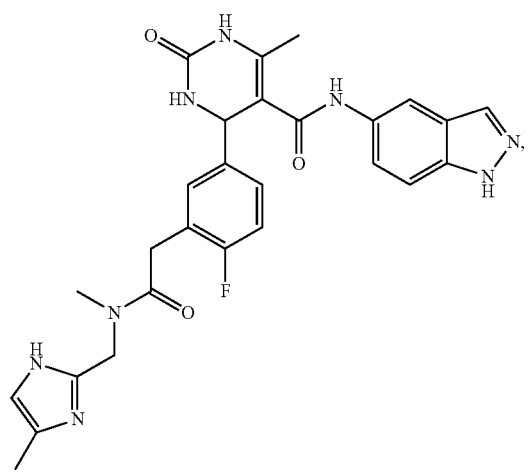
E34
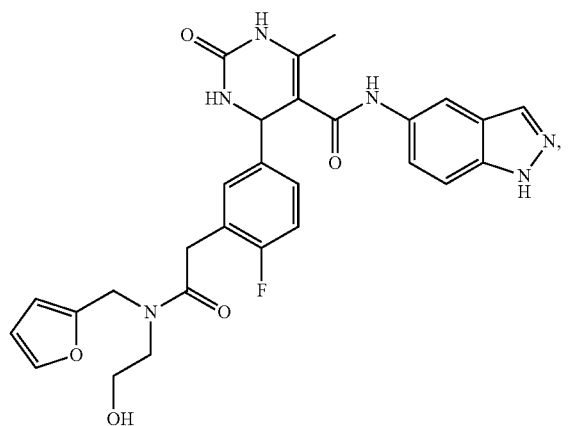
E32
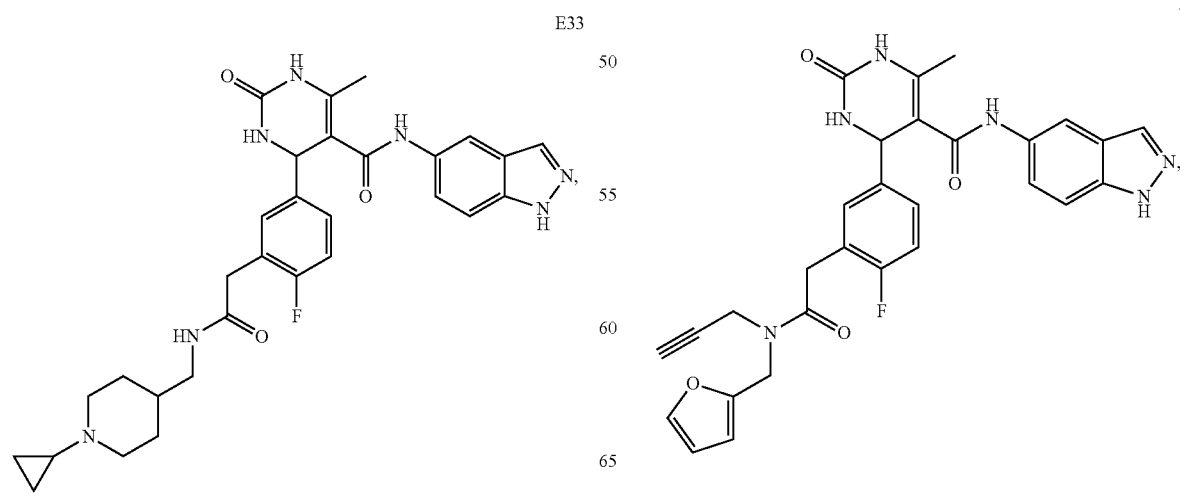

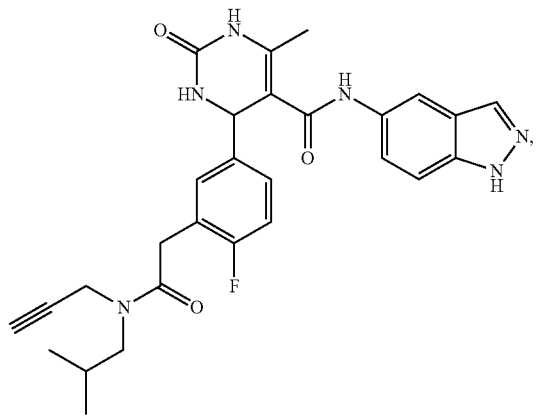

or a pharmaceutically acceptable salt thereof.

15. A pharmaceutical formulation comprising the compound of claim 1 and a pharmaceutically acceptable excipient.

16. A method of inhibiting GRK2 in a cell, comprising contacting the cell with the compound of claim 1 in an amount effective to inhibit GRK2.

17. The method of claim 16, wherein the compound is a compound of claim 14, or pharmaceutically acceptable salt thereof.

18. The method of claim 16, wherein the cell is a myocyte.

19. A method of treating heart disease in a subject comprising administering to the subject a therapeutically effective amount of the pharmaceutical formulation of claim 15.

20. The method of claim 19, wherein the heart disease is cardiac failure, cardiac hypertrophy, hypertension, or a combination thereof.

* * * * *